United States Patent
Hatakeyama et al.

(10) Patent No.: US 10,606,172 B2
(45) Date of Patent: Mar. 31, 2020

(54) RESIST COMPOSITION AND PATTERNING PROCESS

(71) Applicant: SHIN-ETSU CHEMICAL CO., LTD., Tokyo (JP)

(72) Inventors: Jun Hatakeyama, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 45 days.

(21) Appl. No.: 15/920,746

(22) Filed: Mar. 14, 2018

(65) Prior Publication Data

US 2018/0267403 A1    Sep. 20, 2018

(30) Foreign Application Priority Data

Mar. 17, 2017    (JP) .................................. 2017-052391

(51) Int. Cl.

| | | |
|---|---|---|
| *G03F 7/004* | (2006.01) | |
| *G03F 7/38* | (2006.01) | |
| *G03F 7/039* | (2006.01) | |
| *G03F 7/038* | (2006.01) | |
| *G03F 7/16* | (2006.01) | |
| *G03F 7/32* | (2006.01) | |
| *G03F 7/20* | (2006.01) | |
| *C08F 220/20* | (2006.01) | |
| *C08F 220/38* | (2006.01) | |
| *C08F 220/16* | (2006.01) | |
| *C08F 222/24* | (2006.01) | |
| *C08F 222/14* | (2006.01) | |
| *C08F 220/24* | (2006.01) | |
| *C08F 220/26* | (2006.01) | |
| *C08F 222/16* | (2006.01) | |
| *C08F 228/02* | (2006.01) | |
| *C08F 222/20* | (2006.01) | |
| *C08F 224/00* | (2006.01) | |
| *C08F 220/28* | (2006.01) | |
| *C08F 220/22* | (2006.01) | |
| *C08F 222/18* | (2006.01) | |
| *C07C 309/04* | (2006.01) | |
| *C07C 309/39* | (2006.01) | |
| *C07C 303/32* | (2006.01) | |
| *C07C 309/06* | (2006.01) | |

(Continued)

(52) U.S. Cl.
CPC .......... *G03F 7/0045* (2013.01); *C07C 69/635* (2013.01); *C07C 303/32* (2013.01); *C07C 309/04* (2013.01); *C07C 309/06* (2013.01); *C07C 309/07* (2013.01); *C07C 309/39* (2013.01); *C08F 220/16* (2013.01); *C08F 220/20* (2013.01); *C08F 220/22* (2013.01); *C08F 220/24* (2013.01); *C08F 220/26* (2013.01); *C08F 220/28* (2013.01); *C08F 220/38* (2013.01); *C08F 222/14* (2013.01); *C08F 222/16* (2013.01); *C08F 222/18* (2013.01); *C08F 222/20* (2013.01); *C08F 222/24* (2013.01); *C08F 224/00* (2013.01); *C08F 228/02* (2013.01); *G03F 7/0046* (2013.01); *G03F 7/0382* (2013.01); *G03F 7/0397* (2013.01); *G03F 7/162* (2013.01); *G03F 7/168* (2013.01); *G03F 7/2004* (2013.01); *G03F 7/2006* (2013.01); *G03F 7/2037* (2013.01); *G03F 7/2041* (2013.01); *G03F 7/322* (2013.01); *G03F 7/325* (2013.01); *G03F 7/38* (2013.01); *C08F 2220/281* (2013.01); *C08F 2220/282* (2013.01); *C08F 2220/283* (2013.01); *C08F 2220/301* (2013.01); *C08F 2220/302* (2013.01); *C08F 2220/382* (2013.01)

(58) Field of Classification Search
CPC .... G03F 7/0045; G03F 7/0382; G03F 7/0397; G03F 7/38; C08F 220/16; C08F 220/20; C08F 220/22; C08F 220/24; C08F 220/26; C08F 220/28; C08F 2220/281; C08F 2220/282; C08F 2220/283; C08F 2220/301; C08F 2220/302; C08F 220/38; C08F 2220/382; C08F 222/14; C08F 222/16; C08F 222/18; C08F 222/20; C08F 222/24; C08F 224/00; C08F 228/02; C07C 69/635; C07C 303/32; C07C 309/04; C07C 309/06; C07C 309/07; C07C 309/39
USPC ..................................... 430/270.1, 325, 326
See application file for complete search history.

(56) References Cited

U.S. PATENT DOCUMENTS 6,551,758 B2 *  4/2003  Ohsawa ................ C07C 309/42
                                                        430/270.1
6,673,511 B1    1/2004  Hatakeyama et al.
(Continued)

FOREIGN PATENT DOCUMENTS

JP    2001-194776 A    7/2001
JP    2002-226470 A    8/2002
(Continued)

OTHER PUBLICATIONS

Wang et al., "Photobase generator and photo decomposable quencher for high-resolution photoresist applications", Pro. of SPIE, (2010), vol. 7639, pp. 46390W, w/English Abstract, (Cited in Specification), (15pages).

*Primary Examiner* — John S Chu
(74) *Attorney, Agent, or Firm* — Westerman, Hattori, Daniels & Adrian, LLP

(57) ABSTRACT

A resist composition comprising a base polymer and a quencher in the form of an iodonium salt capable of generating fluorobenzoic acid bonded to iodized benzene offers a high sensitivity and minimal LWR independent of whether it is of positive or negative tone.

18 Claims, No Drawings

(51) Int. Cl.
  *C07C 309/07*   (2006.01)
  *C07C 69/635*   (2006.01)
  *C08F 220/30*   (2006.01)

(56) References Cited

U.S. PATENT DOCUMENTS

| | | | |
|---|---|---|---|
| 6,692,893 B2 * | 2/2004 | Ohsawa | G03F 7/0045 |
| | | | 430/270.1 |
| 6,749,988 B2 | 6/2004 | Hatakeyama et al. | |
| 6,916,593 B2 | 7/2005 | Hatakeyama et al. | |
| 8,092,977 B2 * | 1/2012 | Mizutani | G03F 7/0045 |
| | | | 430/270.1 |
| 9,250,518 B2 | 2/2016 | Hatakeyama et al. | |

FOREIGN PATENT DOCUMENTS

| | | | |
|---|---|---|---|
| JP | 2002-363148 A | 12/2002 | |
| JP | 2015-90382 A | 5/2015 | |

* cited by examiner

RESIST COMPOSITION AND PATTERNING PROCESS

CROSS-REFERENCE TO RELATED APPLICATION

This non-provisional application claims priority under 35 U.S.C. § 119(a) on Patent Application No. 2017-052391 filed in Japan on Mar. 17, 2017, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

As the pattern feature size is reduced, approaching to the diffraction limit of light, light contrast lowers. In the case of positive resist film, a lowering of light contrast leads to reductions of resolution and focus margin of hole and trench patterns. For mitigating the influence of reduced resolution of resist pattern due to a lowering of light contrast, an attempt is made to enhance the dissolution contrast of resist film.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein crosslinking reaction takes place under the action of acid. Quenchers are often added to these resist compositions for the purpose of controlling the diffusion of the acid to unexposed areas to improve the contrast. The addition of quenchers is fully effective to this purpose. A number of amine quenchers were proposed as disclosed in Patent Documents 1 to 3.

With respect to the acid labile group used in (meth) acrylate polymers for the ArF lithography, deprotection reaction takes place when a photoacid generator capable of generating a sulfonic acid having fluorine substituted at α-position (referred to "α-fluorinated sulfonic acid") is used, but not when an acid generator capable of generating a sulfonic acid not having fluorine substituted at α-position (referred to "α-non-fluorinated sulfonic acid") or carboxylic acid is used. If a sulfonium or iodonium salt capable of generating an α-fluorinated sulfonic acid is combined with a sulfonium or iodonium salt capable of generating an α-non-fluorinated sulfonic acid, the sulfonium or iodonium salt capable of generating an α-non-fluorinated sulfonic acid undergoes ion exchange with the α-fluorinated sulfonic acid. Through the ion exchange, the α-fluorinated sulfonic acid thus generated by light exposure is converted back to the sulfonium or iodonium salt while the sulfonium or iodonium salt of an α-non-fluorinated sulfonic acid or carboxylic acid functions as a quencher.

Further, the sulfonium or iodonium salt capable of generating an α-non-fluorinated sulfonic acid also functions as a photodegradable quencher since it loses the quencher function by photodegradation. Non-Patent Document 1 points out that the addition of a photodegradable quencher expands the margin of a trench pattern although the structural formula is not illustrated. However, it has only a little influence on performance improvement. There is a desire to have a quencher for further improving contrast.

Patent Document 4 discloses a quencher of onium salt type which reduces its basicity through a mechanism that it generates an amino-containing carboxylic acid upon light exposure, which in turn forms a lactam in the presence of acid. Due to the mechanism that basicity is reduced under the action of acid, acid diffusion is controlled by high basicity in the unexposed region where the amount of acid generated is minimal, whereas acid diffusion is promoted due to reduced basicity of the quencher in the overexposed region where the amount of acid generated is large. This expands the difference in acid amount between the exposed and unexposed regions, from which an improvement in contrast is expected. Despite the advantage of improved contrast, the acid diffusion controlling effect is rather reduced.

As the pattern feature size is reduced, the edge roughness (LWR) of line patterns and the critical dimension uniformity (CDU) of hole patterns are regarded significant. It is pointed out that these factors are affected by the segregation or agglomeration of a base polymer and acid generator and the diffusion of generated acid. There is a tendency that as the resist film becomes thinner, LWR becomes greater. A film thickness reduction to comply with the progress of size reduction causes a degradation of LWR, which becomes a serious problem.

The EUV lithography resist must meet high sensitivity, high resolution and low LWR at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR.

CITATION LIST

Patent Document 1: JP-A 2001-194776
Patent Document 2: JP-A 2002-226470
Patent Document 3: JP-A 2002-363148
Patent Document 4: JP-A 2015-090382
Non-Patent Document 1: SPIE Vol. 7639 p 76390 W (2010)

DISCLOSURE OF INVENTION

For the acid-catalyzed chemically amplified resist, it is desired to develop a quencher capable of providing a high sensitivity and reducing LWR or improving CDU of hole patterns.

An object of the invention is to provide a resist composition which exhibits a high sensitivity and a reduced LWR or improved CDU, independent of whether it is of positive tone or negative tone; and a pattern forming process using the same.

The inventors have found that using an iodonium salt capable of generating a fluorobenzoic acid bonded to iodized benzene as the quencher, a resist material having a reduced LWR, improved CDU, high contrast, improved resolution, and wide process margin is obtainable.

In one aspect, the invention provides a resist composition comprising a base polymer and a quencher containing an iodonium salt having the formula (A).

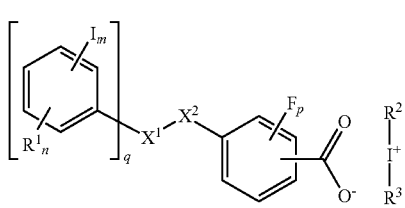

Herein $R^1$ is a hydroxyl group, $C_1$-$C_6$ straight, branched or cyclic alkyl or alkoxy group, $C_2$-$C_6$ straight, branched or cyclic acyloxy group, fluorine, chlorine, bromine, amino, —$NR^5$—C(=O)—$R^6$, or —$NR^5$—C(=O)—O—$R^6$, wherein $R^5$ is hydrogen or a $C_1$-$C_6$ straight, branched or cyclic alkyl group, $R^6$ is a $C_1$-$C_6$ straight, branched or cyclic alkyl group or $C_2$-$C_8$ straight, branched or cyclic alkenyl group. $X^1$ is a single bond or a (q+1)-valent $C_1$-$C_{20}$ linking group which may contain at least one moiety selected from ether, carbonyl, ester, amide, sultone, lactam, carbonate, halogen, hydroxyl and carboxyl. $X^2$ is an ether, ester or amide group. $R^2$ and $R^3$ are each independently trifluoromethyl or a $C_6$-$C_{10}$ aryl, $C_2$-$C_6$ alkenyl or $C_2$-$C_6$ alkynyl group in which at least one hydrogen atom may be substituted by halogen, trifluoromethyl, $C_1$-$C_{10}$ straight, branched or cyclic alkyl, $C_1$-$C_{10}$ straight, branched or cyclic alkoxy, hydroxyl, carboxyl, $C_2$-$C_{10}$ straight, branched or cyclic alkoxycarbonyl, nitro and/or cyano; m is an integer of 1 to 5, n is an integer of 0 to 3, p is an integer of 1 to 4, and q is an integer of 1 to 3.

Preferably, m is equal to 3.

The resist composition may further comprise an acid generator capable of generating a sulfonic acid, imide acid or methide acid, and an organic solvent.

In a preferred embodiment, the base polymer comprises recurring units having the formula (a1) or recurring units having the formula (a2).

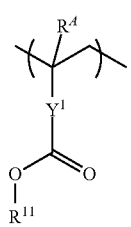

(a1)

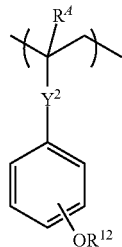

(a2)

Herein $R^A$ is each independently hydrogen or methyl, $R^{11}$ and $R^{12}$ each are an acid labile group, $Y^1$ is a single bond, phenylene group, naphthylene group, or $C_1$-$C_{12}$ linking group containing an ester moiety and/or lactone ring, and $Y^2$ is a single bond or ester group.

The resist composition may further comprise a dissolution inhibitor and/or a surfactant.

In one embodiment, the resist composition is a chemically amplified positive resist composition.

In another embodiment, the base polymer is free of an acid labile group. The resist composition may further comprise a crosslinker. The resist composition is typically a chemically amplified negative resist composition.

In a preferred embodiment, the base polymer further comprises recurring units of at least one type selected from the formulae (f1) to (f3).

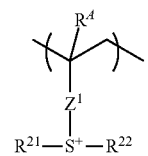

(f1)

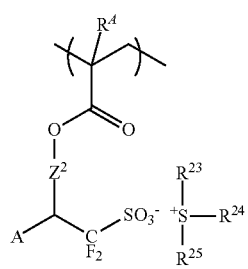

(f2)

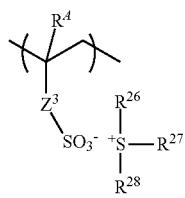

(f3)

Herein $R^A$ is each independently hydrogen or methyl; $Z^1$ is a single bond, phenylene group, —O—$Z^{12}$— or —C(=O)—$Z^{11}$—$Z^{12}$—, $Z^{11}$ is —O— or —NH—, $Z^{12}$ is a $C_1$-$C_6$ straight, branched or cyclic alkylene group, $C_2$-$C_6$ straight, branched or cyclic alkenylene group or phenylene group, which may contain a carbonyl, ester, ether or hydroxy moiety; $R^{21}$ to $R^{28}$ are each independently a $C_1$-$C_{12}$ straight, branched or cyclic alkyl group which may contain a carbonyl, ester or ether moiety, or a $C_6$-$C_{12}$ aryl group or $C_7$-$C_{20}$ aralkyl group, in which at least one hydrogen may be substituted by a $C_1$-$C_{10}$ straight, branched or cyclic alkyl moiety, halogen, trifluoromethyl, cyano, nitro, hydroxyl, mercapto, $C_1$-$C_{10}$ straight, branched or cyclic alkoxy moiety, $C_2$-$C_{10}$ straight, branched or cyclic alkoxycarbonyl moiety, or $C_2$-$C_{10}$ straight, branched or cyclic acyloxy moiety, any two of $R^{23}$, $R^{24}$ and $R^{25}$, or any two of $R^{26}$, $R^{27}$ and $R^{28}$ may bond together to form a ring with the sulfur atom to which they are attached; $Z^2$ is a single bond, —$Z^{21}$—C(=O)—O—, —$Z^{21}$—O— or —$Z^{21}$—O—C(=O)—, $Z^{21}$ is a $C_1$-$C_{12}$ straight, branched or cyclic alkylene group which may contain a carbonyl, ester or ether moiety; A is hydrogen or trifluoromethyl; $Z^3$ is a single bond, methylene group, ethylene group, phenylene group, fluorinated phenylene group, —O—$Z^{32}$—, or —C(=O)—$Z^{31}$—$Z^{32}$—, $Z^{31}$ is —O— or —NH—, $Z^{32}$ is a $C_1$-$C_6$ straight, branched or cyclic alkylene group, phenylene, fluorinated phenylene or trifluoromethyl-substituted phenylene group, or $C_2$-$C_6$ straight, branched or cyclic alkenylene group, which may contain a carbonyl, ester, ether or hydroxyl moiety, and M is a non-nucleophilic counter ion.

In another aspect, the invention provides a process for forming a pattern comprising the steps of applying the resist composition defined above onto a substrate, baking to form a resist film, exposing the resist film to high-energy radiation, and developing the exposed film in a developer.

In a preferred embodiment, the high-energy radiation is ArF excimer laser radiation of wavelength 193 nm, KrF excimer laser radiation of wavelength 248 nm, EB, or EUV of wavelength 3 to 15 nm.

Advantageous Effects of Invention

A resist film containing an iodonium salt capable of generating a fluorobenzoic acid bonded to iodized benzene has the advantage that the iodonium salt of fluorobenzenecarboxylic acid bonded to iodized benzene ring is highly effective for suppressing acid diffusion because of the large atomic weight of iodine. This contributes to low LWR and improved CDU. Since iodine is highly absorptive to EUV of wavelength 13.5 nm, it generates numerous secondary electrons during exposure, contributing to a higher sensitivity.

DESCRIPTION OF EMBODIMENTS

As used herein, the singular forms "a," "an" and "the" include plural referents unless the context clearly dictates otherwise. The notation ($C_n$-$C_m$) means a group containing from n to m carbon atoms per group. As used herein, the term "iodized" compound means an iodine-containing compound. In chemical formulae, Me stands for methyl, Ac for acetyl, and Ph for phenyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity Resist Composition The resist composition of the invention is defined as comprising a base polymer and a quencher containing an iodonium salt of a fluorobenzoic acid bonded to iodized benzene. The iodonium salt is an acid generator capable of generating a fluorobenzoic acid bonded to iodized benzene upon light exposure, but also functions as a quencher at the same time because it possesses a strongly basic iodonium. Since the fluorobenzoic acid bonded to iodized benzene does not possess a sufficient acidity to induce deprotection reaction of acid labile groups, it is recommended to separately add an acid generator capable of generating a strong acid such as α-fluorinated sulfonic acid, imide acid or methide acid, as will be described later, in order to induce deprotection reaction of acid labile groups. The acid generator capable of generating a strong acid such as α-fluorinated sulfonic acid, imide acid or methide acid may be either of separate type which is added to the base polymer or of bound type which is bound in the base polymer.

When a resist composition containing the iodonium salt capable of generating fluorobenzoic acid bonded to iodized benzene in admixture with an acid generator capable of generating a perfluoroalkylsulfonic acid or superstrong acid is exposed to radiation, fluorobenzoic acid bonded to iodized benzene and perfluoroalkylsulfonic acid generate. Since the acid generator is not entirely decomposed, the undecomposed acid generator is present nearby. When the iodonium salt capable of generating fluorobenzoic acid bonded to iodized benzene co-exists with the perfluoroalkylsulfonic acid, the perfluoroalkylsulfonic acid first undergoes ion exchange with the iodonium salt capable of generating fluorobenzoic acid bonded to iodized benzene, whereby an iodonium salt of perfluoroalkylsulfonic acid is created and a fluorobenzoic acid bonded to iodized benzene is released. This is because the salt of perfluoroalkylsulfonic acid having a high acid strength is more stable. In contrast, when an iodonium salt of perfluoroalkylsulfonic acid co-exists with a fluorobenzoic acid bonded to iodized benzene, no ion exchange takes place. The ion exchange reaction according to the acid strength series occurs not only with iodonium salts, but also similarly with sulfonium salts. Likewise, ion exchange takes place not only with the perfluoroalkylsulfonic acid, but also similarly with arylsulfonic acid, alkylsulfonic acid, imide acid and methide acid having a higher acid strength than the fluorobenzoic acid bonded to iodized benzene.

The fluorobenzoic acid bonded to iodized benzene has a high molecular weight owing to iodine and thus a high ability to suppress acid diffusion. Since iodine is highly absorptive to EUV of wavelength 13.5 nm, it generates secondary electrons upon EUV exposure. The energy of secondary electrons is transferred to the acid generator to promote its decomposition, contributing to a higher sensitivity. The effect becomes significant when the number of iodine substitution is 3 or more.

While the quencher used herein should essentially contain the iodonium salt of fluorobenzoic acid bonded to iodized benzene, another sulfonium or iodonium salt may be separately added as the quencher. Examples of the sulfonium or iodonium salt to be added as the quencher include sulfonium or iodonium salts of carboxylic acid, sulfonic acid, imide acid and saccharin. The carboxylic acid used herein may or may not be fluorinated at α-position.

For the LWR improving purpose, the dispersibility of the quencher is an important factor. Even when the dispersibility of the acid generator in a resist film is improved, the quencher can cause a lowering of LWR if it is unevenly distributed. The iodonium salt is more solvent soluble and more uniformly dispersible in a film than the sulfonium salt. Moreover, the iodonium salt has a higher molecular weight and more effective for suppressing acid diffusion than the sulfonium salt. The iodonium salt quencher having better uniform dispersibility and acid diffusion suppressing effect is more effective for providing reduced edge roughness and high sensitivity in the EUV lithography than the sulfonium salt quencher.

The iodonium salt of fluorobenzoic acid bonded to iodized benzene exerts a LWR reducing effect, which may stand good either in positive and negative tone pattern formation by alkaline development or in negative tone pattern formation by organic solvent development.

Quencher

The quencher used herein contains an iodonium salt having the formula (A).

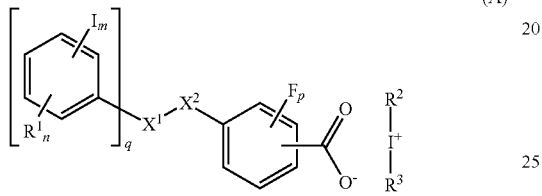
(A)

Herein $R^1$ is a hydroxyl group, $C_1$-$C_6$ straight, branched or cyclic alkyl or alkoxy group, $C_2$-$C_6$ straight, branched or cyclic acyloxy group, fluorine, chlorine, bromine, amino, —$NR^5$—C(=O)—$R^6$, or —$NR^5$—C(=O)—O—$R^6$, wherein $R^5$ is hydrogen or a $C_1$-$C_6$ straight, branched or cyclic alkyl group, $R^6$ is a $C_1$-$C_6$ straight, branched or cyclic alkyl group or $C_2$-$C_8$ straight, branched or cyclic alkenyl group. $X^1$ is a single bond or a (q+1)-valent $C_1$-$C_{20}$ linking group which may contain at least one moiety selected from ether, carbonyl, ester, amide, sultone, lactam, carbonate, halogen, hydroxyl and carboxyl. $X^2$ is an ether, ester or amide group. $R^2$ and $R^3$ are each independently trifluoromethyl or a $C_6$-$C_{10}$ aryl, $C_2$-$C_6$ alkenyl or $C_2$-$C_6$ alkynyl group in which at least one hydrogen atom (one or more or even all hydrogen) may be substituted by halogen, trifluoromethyl, $C_1$-$C_{10}$ straight, branched or cyclic alkyl, $C_1$-$C_{10}$ straight, branched or cyclic alkoxy, hydroxyl, carboxyl, $C_2$-$C_{10}$ straight, branched or cyclic alkoxycarbonyl, nitro and/or cyano; m is an integer of 1 to 5, n is an integer of 0 to 3, p is an integer of 1 to 4, and q is an integer of 1 to 3.

Examples of the cation moiety in the iodonium salt having formula (A) are given below, but not limited thereto.

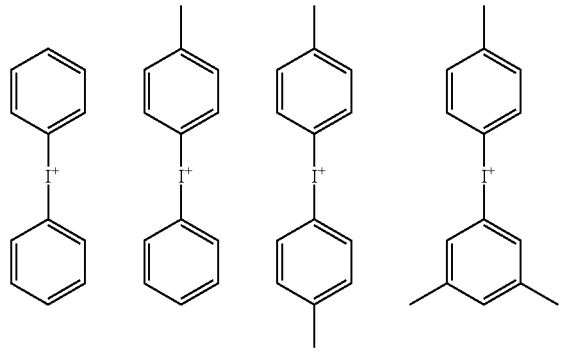

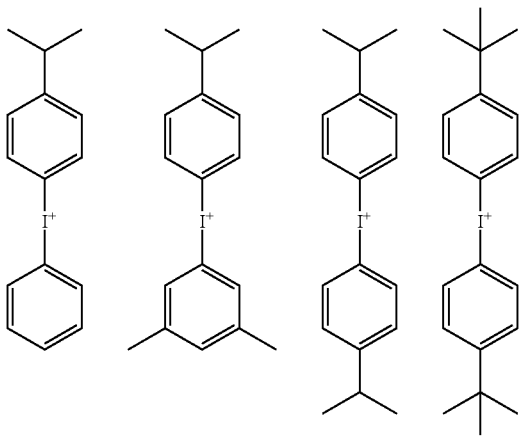

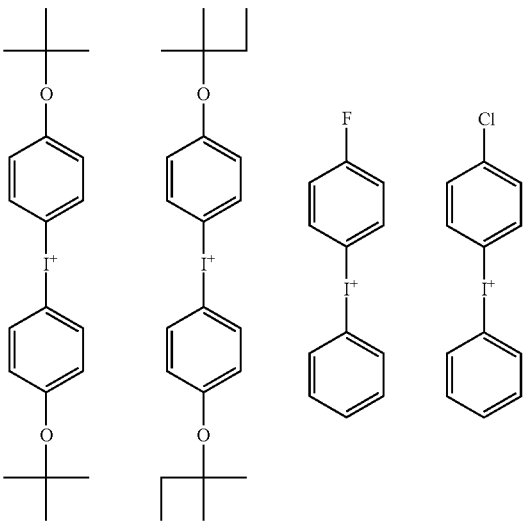

-continued
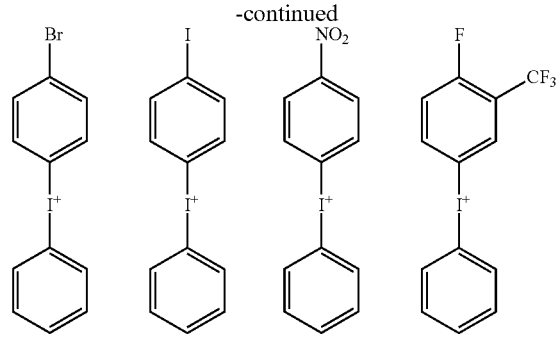
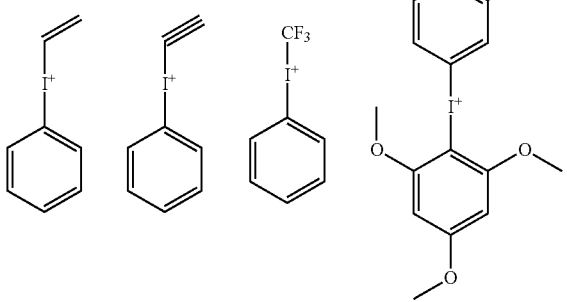
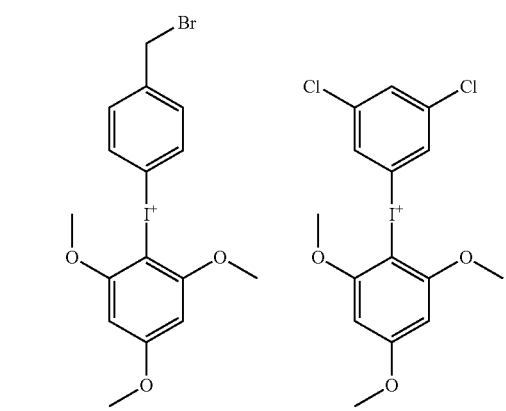
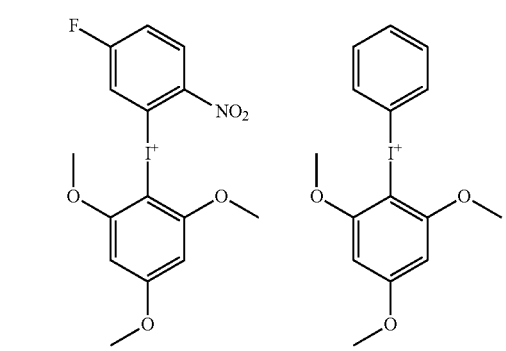
-continued
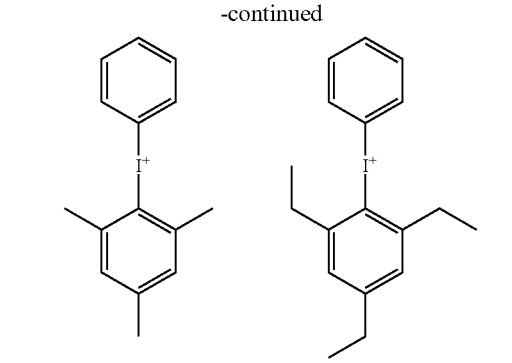
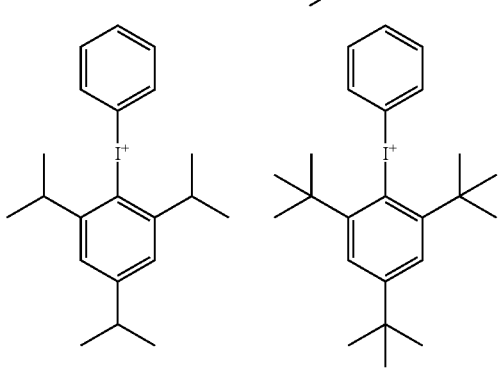
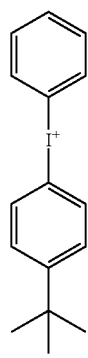
Examples of the anion moiety in the iodonium salt having formula (A) are given below, but not limited thereto.
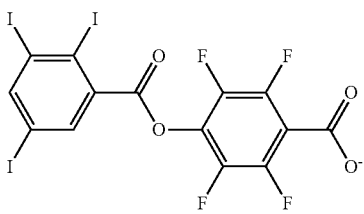
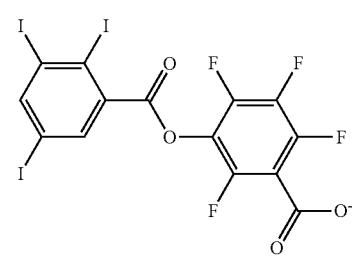

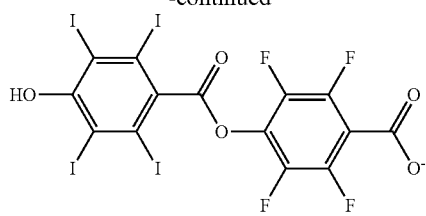
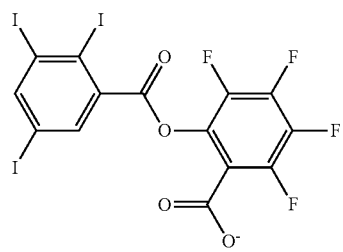
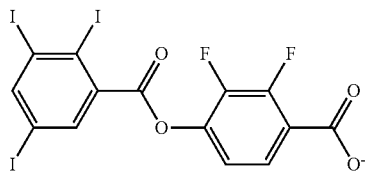
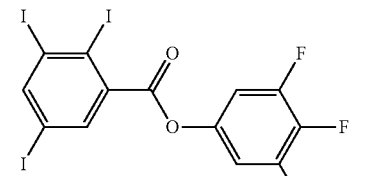
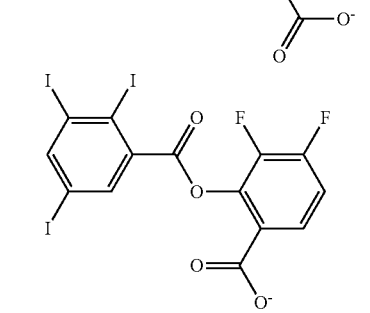
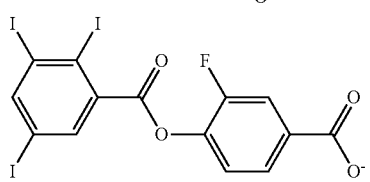
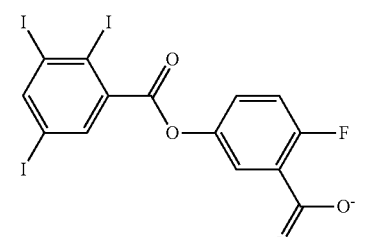
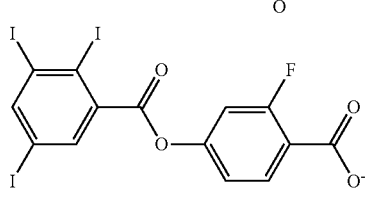
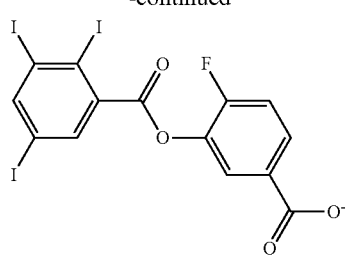
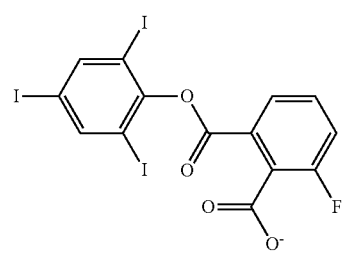
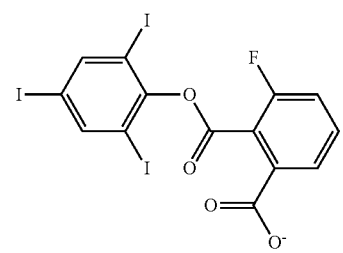
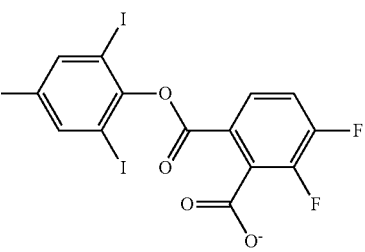
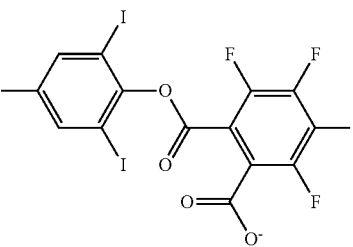
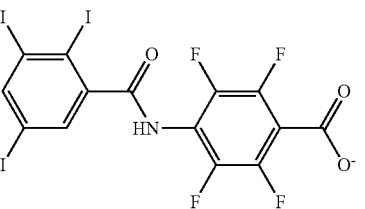
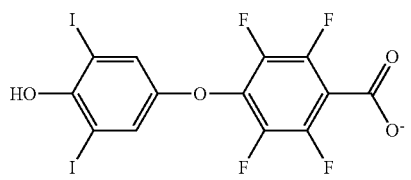

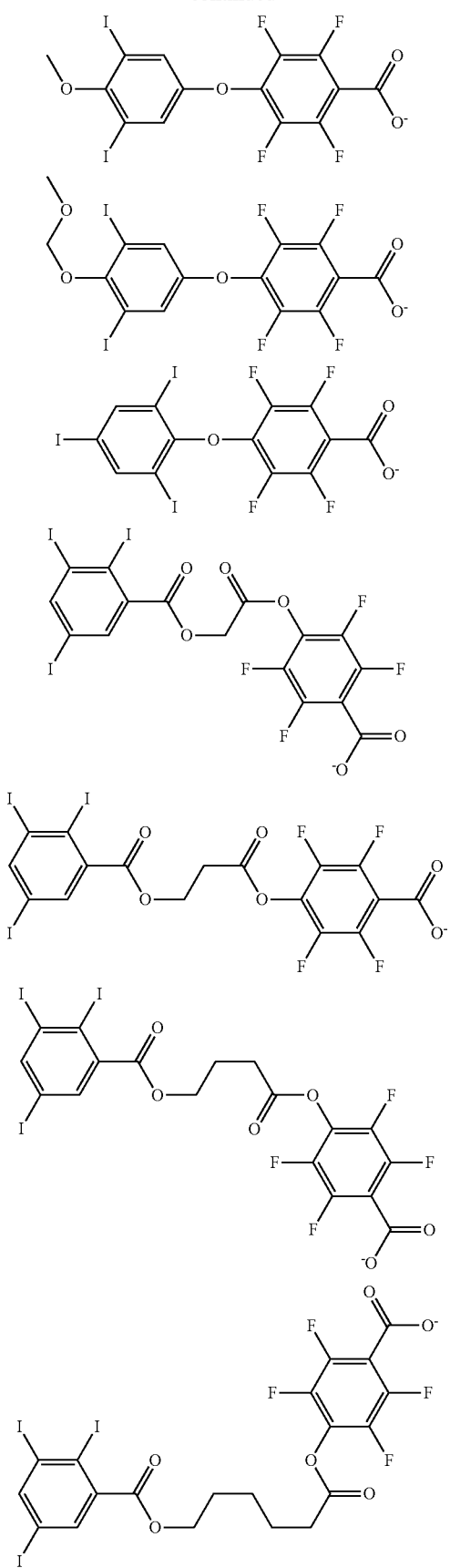
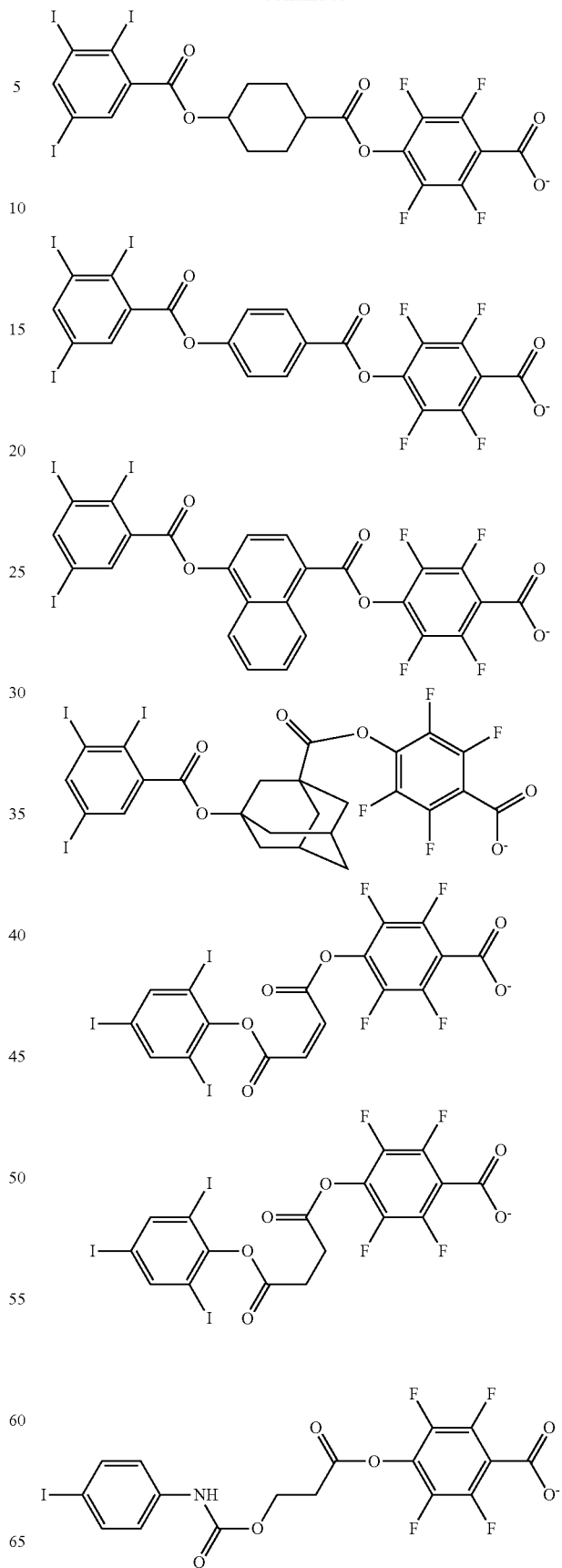

-continued

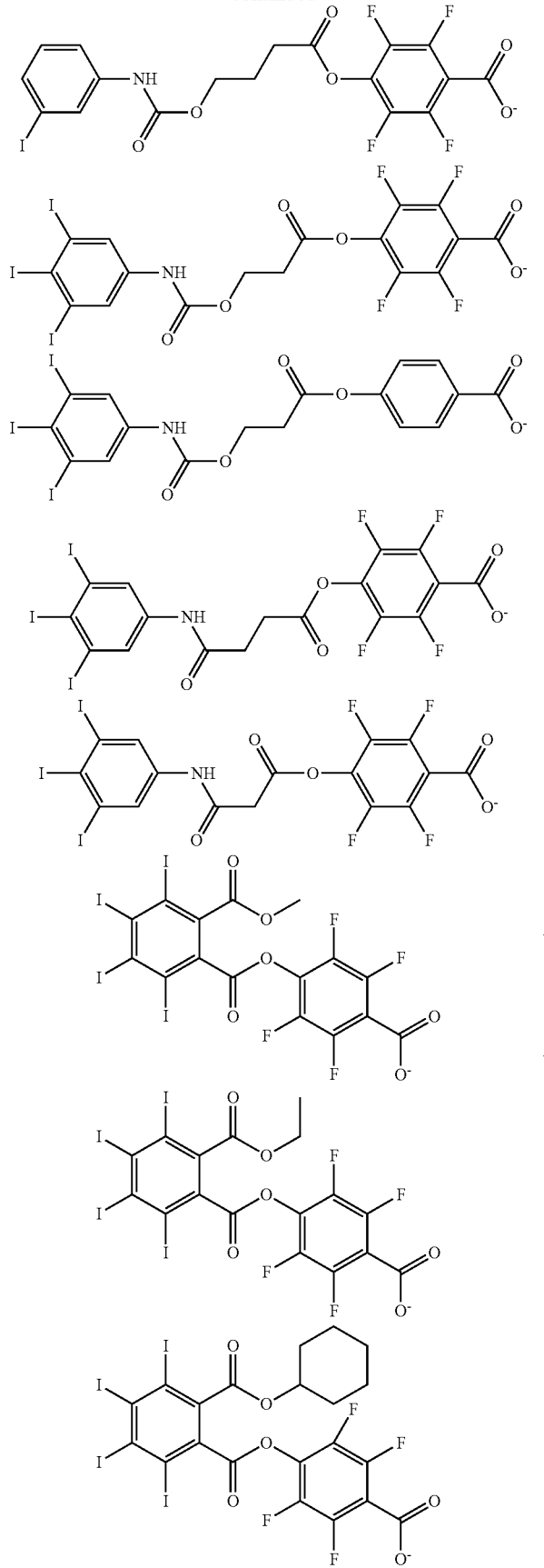

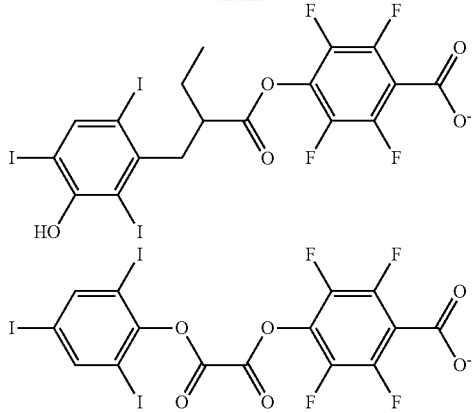

The iodonium salt of fluorobenzoic acid bonded to iodized benzene having formula (A) may be synthesized, for example, by ion exchange with an iodonium salt of weaker acid than the fluorobenzoic acid bonded to iodized benzene. Examples of the weaker acid include non-fluorinated carboxylic acids. Alternatively, the iodonium salt may be synthesized by ion exchange of a sodium salt of a fluorobenzoic acid bonded to iodized benzene with an iodonium chloride.

In the resist composition, the iodonium salt having formula (A) is preferably used in an amount of 0.001 to 50 parts, more preferably 0.01 to 20 parts by weight per 100 parts by weight of the base polymer, as viewed from sensitivity and acid diffusion suppressing effect.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

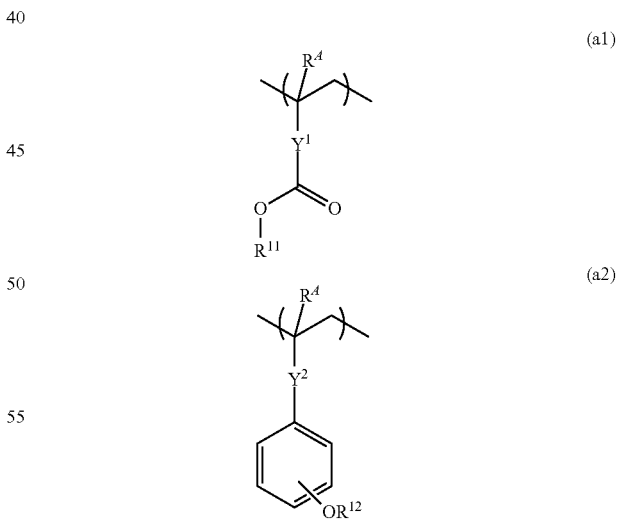

Herein $R^A$ is each independently hydrogen or methyl. $R^{11}$ and $R^{12}$ each are an acid labile group. $Y^1$ is a single bond, phenylene group, naphthylene group, or a $C_1$-$C_{12}$ linking group containing an ester moiety and/or lactone ring. $Y^2$ is a single bond or ester group. When the base polymer contains both recurring units (a1) and (a2), $R^{11}$ and $R^{12}$ may be identical or different.

Examples of the recurring units (a1) are shown below, but not limited thereto. $R^A$ and $R^{11}$ are as defined above.

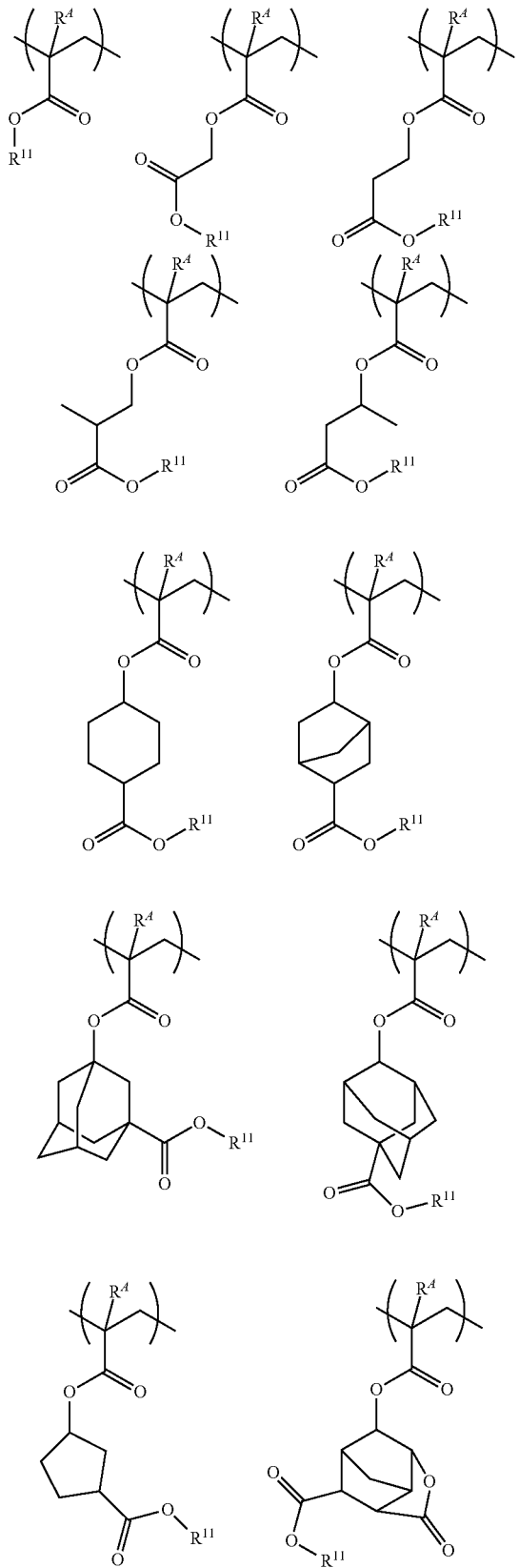

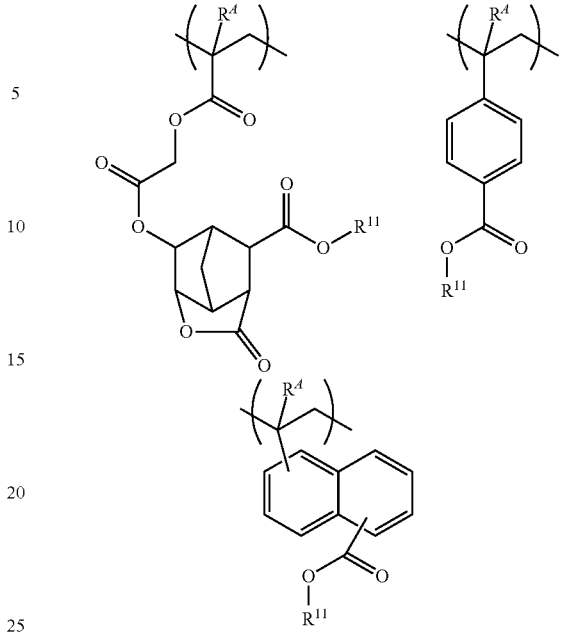

The acid labile groups represented by $R^{11}$ and $R^{12}$ in the recurring units (a1) and (a2) may be selected from a variety of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

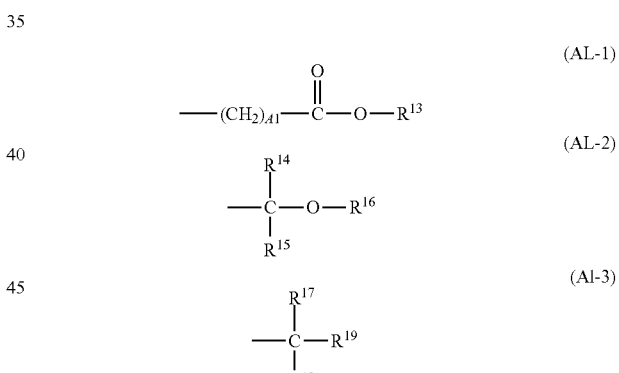

In formulae (AL-1) and (AL-2), $R^{13}$ and $R^{16}$ are each independently a monovalent hydrocarbon group of 1 to 40 carbon atoms, preferably 1 to 20 carbon atoms, typically straight, branched or cyclic alkyl, which may contain a heteroatom such as oxygen, sulfur, nitrogen or fluorine. $R^{14}$ and $R^{15}$ are each independently hydrogen or a monovalent hydrocarbon group of 1 to 20 carbon atoms, typically straight, branched or cyclic alkyl, which may contain a heteroatom such as oxygen, sulfur, nitrogen or fluorine. Any two of $R^{14}$, $R^{15}$, and $R^{16}$ may bond together to form a ring, typically alicyclic, with the carbon atom or carbon and oxygen atoms to which they are attached, the ring containing 3 to 20 carbon atoms, preferably 4 to 16 carbon atoms. A1 is an integer of 0 to 10, especially 1 to 5.

In formula (AL-3), $R^{17}$, $R^{18}$ and $R^{19}$ are each independently a monovalent hydrocarbon group of 1 to 20 carbon atoms, typically straight, branched or cyclic alkyl, which may contain a heteroatom such as oxygen, sulfur, nitrogen or fluorine. Any two of $R^{17}$, $R^{18}$, and $R^{19}$ may bond together to form a ring, typically alicyclic, with the carbon atom to which they are attached, the ring containing 3 to 20 carbon atoms, preferably 4 to 16 carbon atoms.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

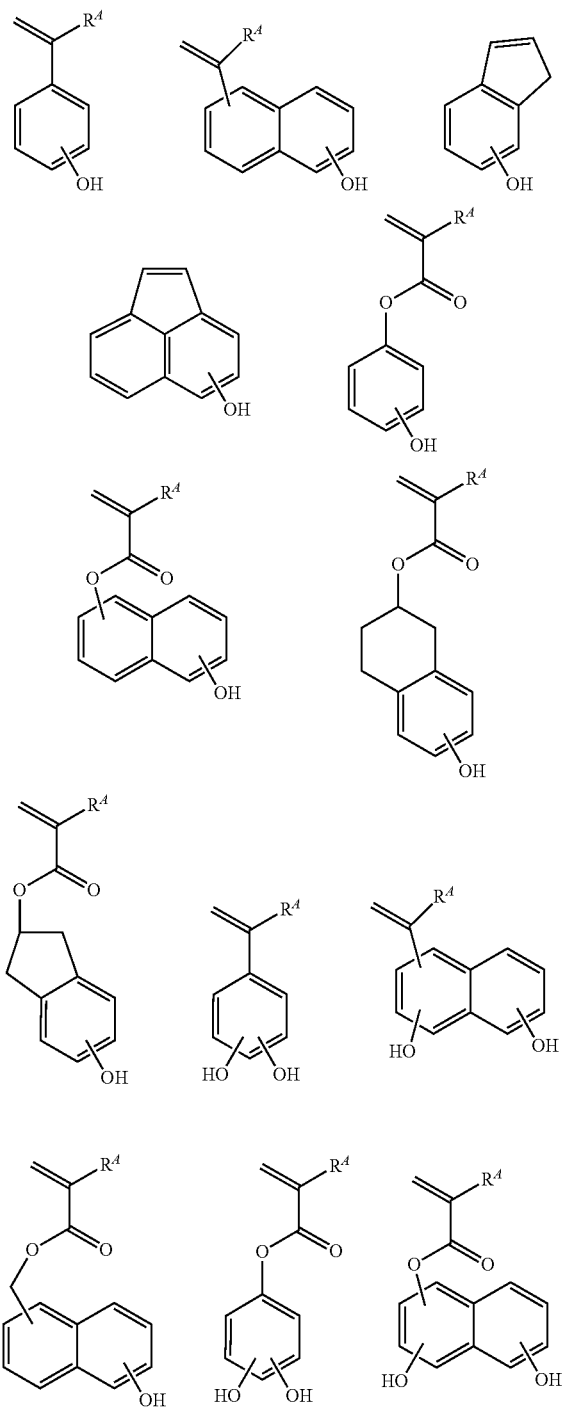

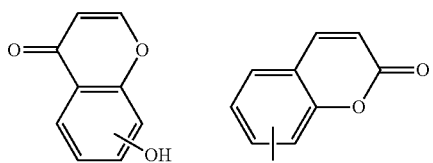

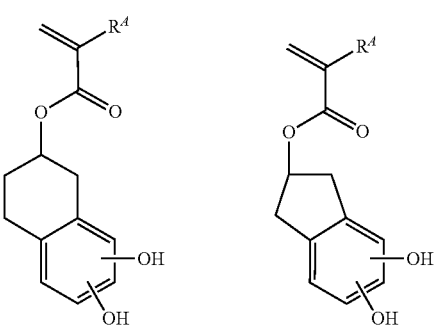

Further, recurring units (c) having another adhesive group selected from hydroxyl (other than the foregoing phenolic hydroxyl), carboxyl, lactone ring, ether, ester, carbonyl and cyano groups may also be incorporated in the base polymer. Examples of suitable monomers from which recurring units (c) are derived are given below, but not limited to thereto. Herein $R^A$ is as defined above.

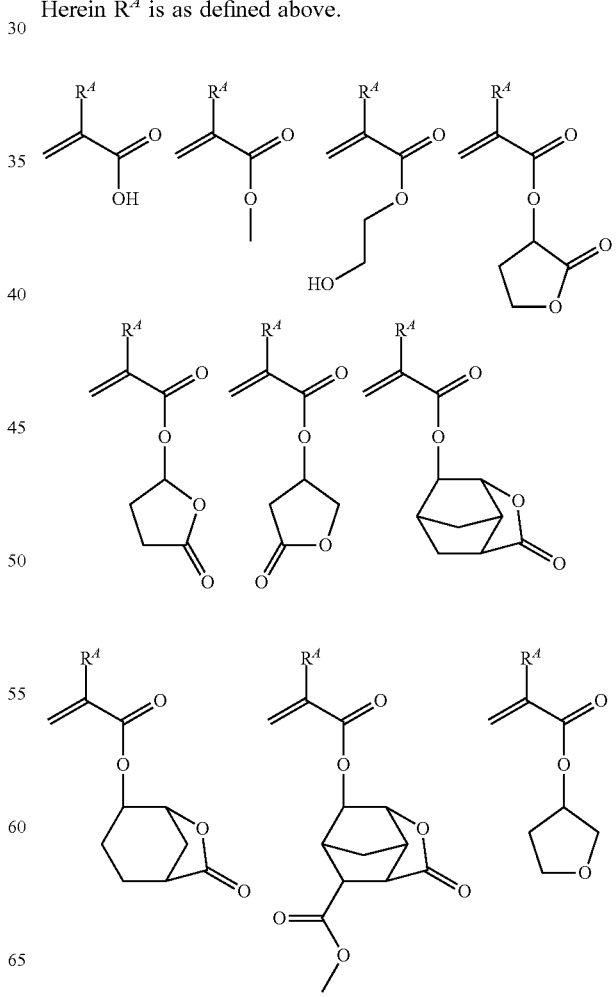

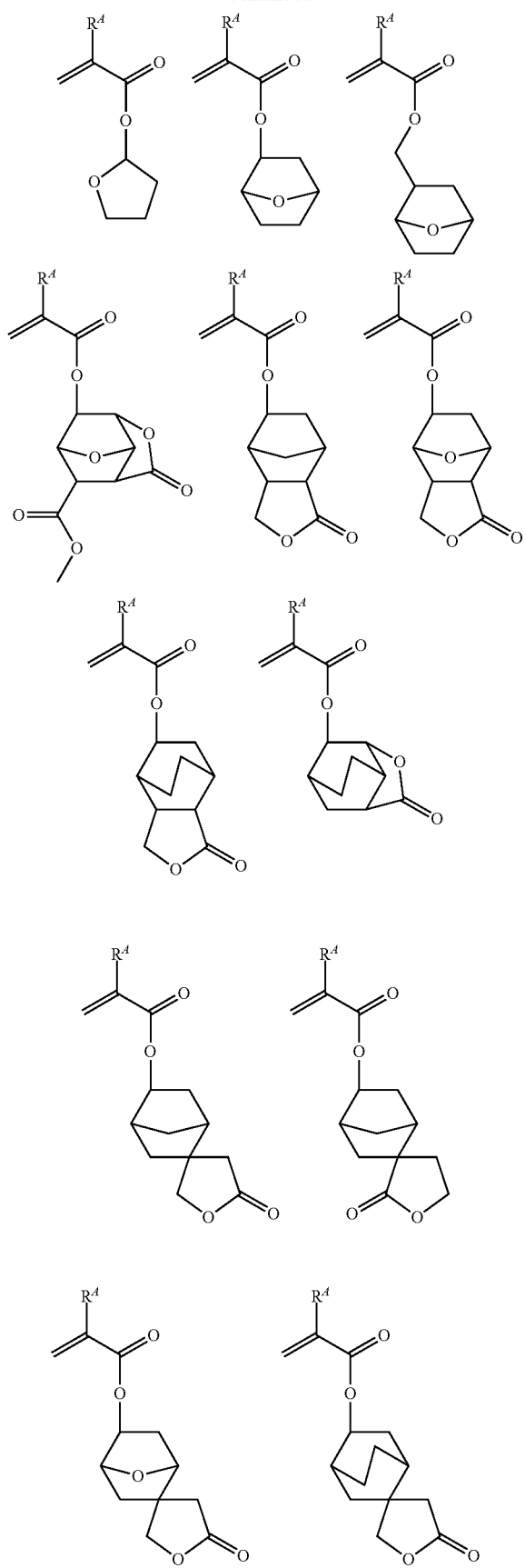
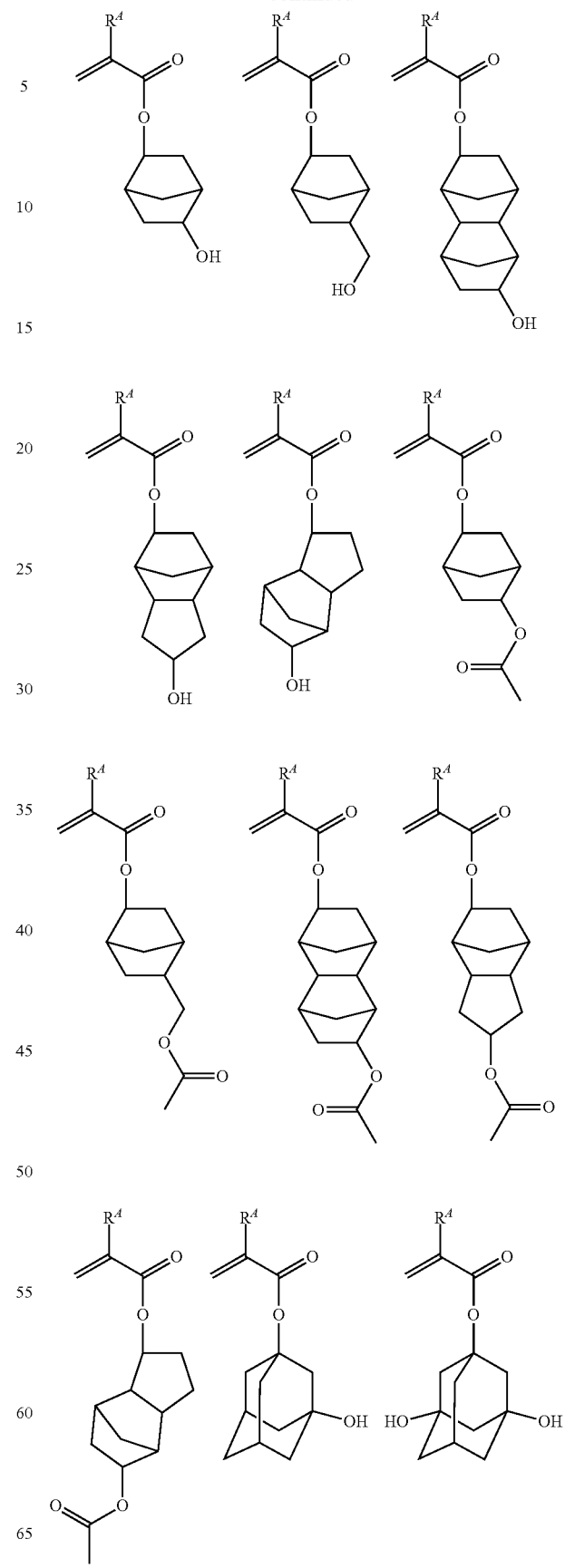

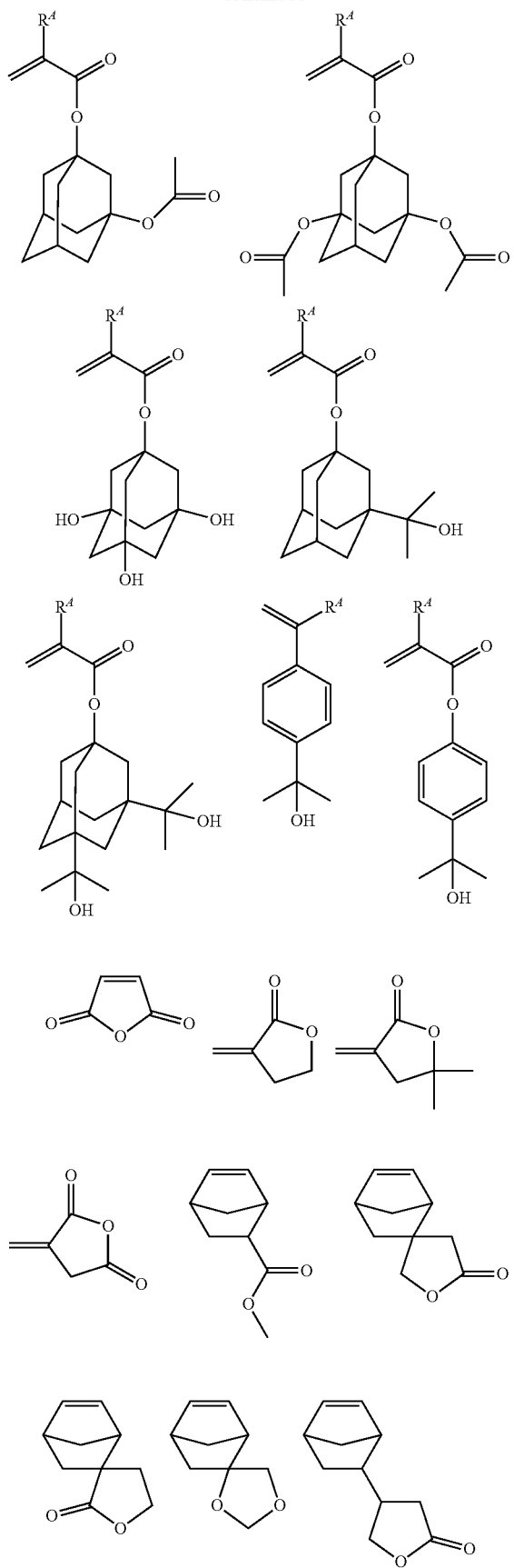
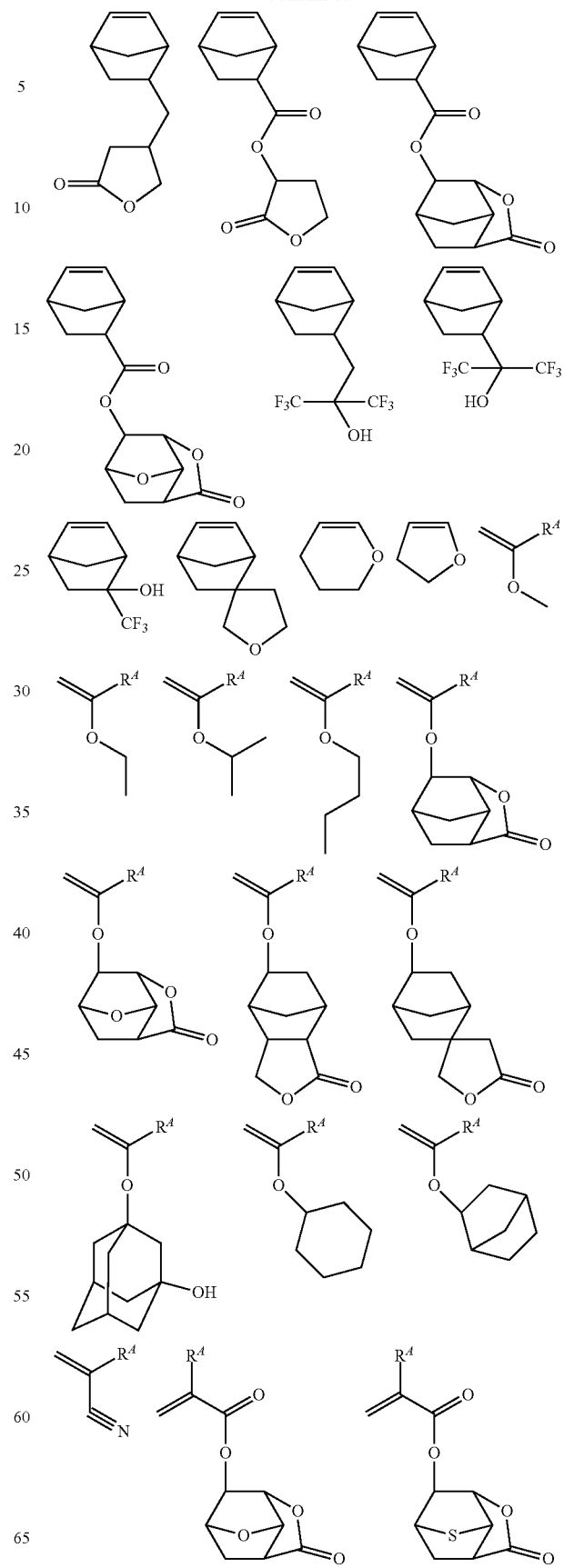

-continued
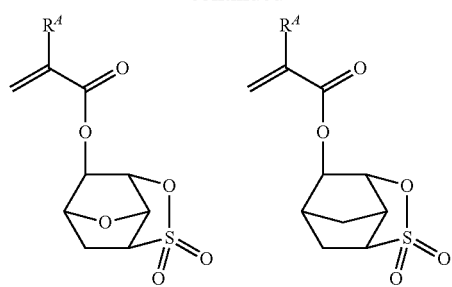
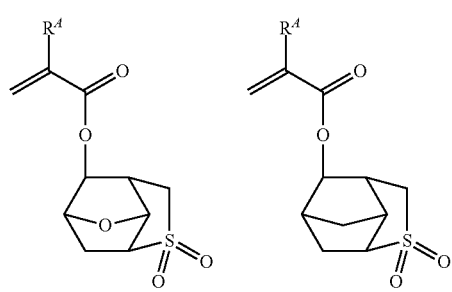
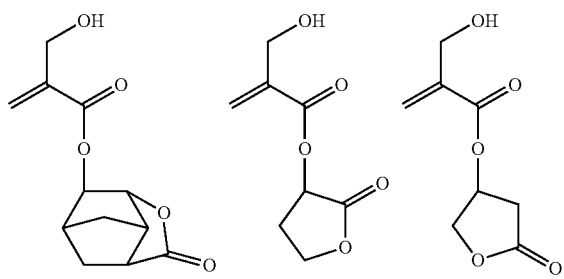
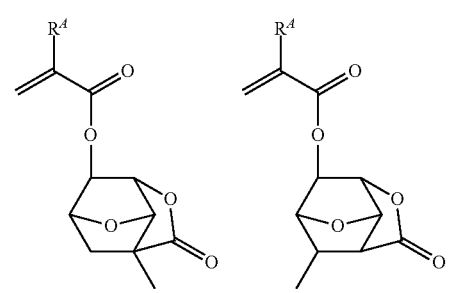
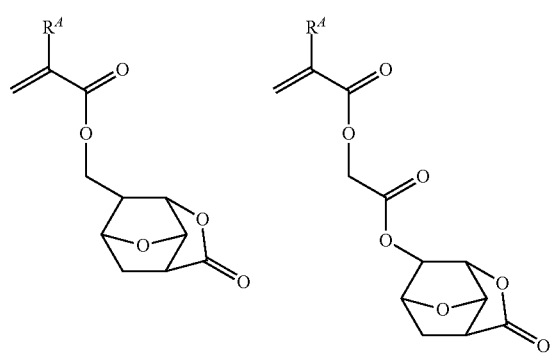
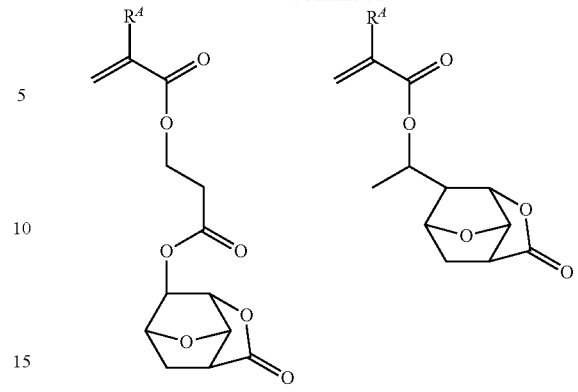
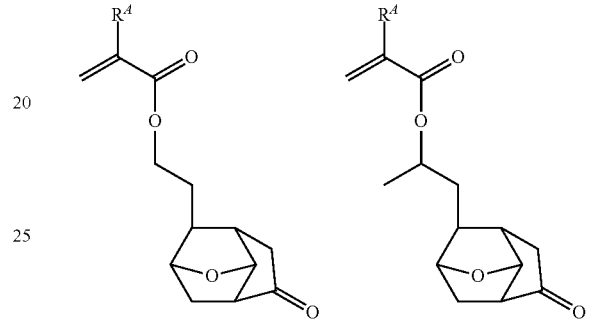
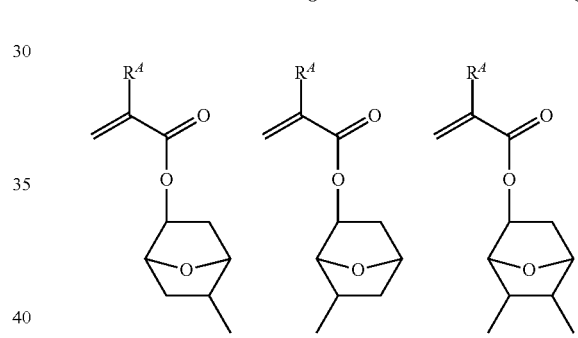
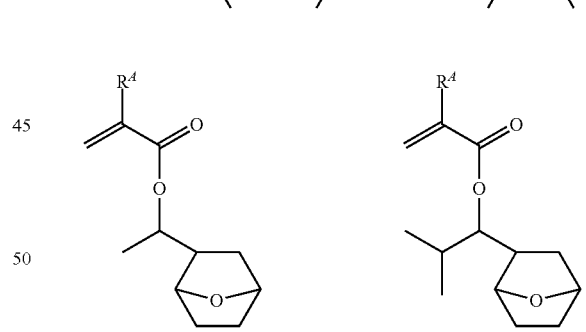
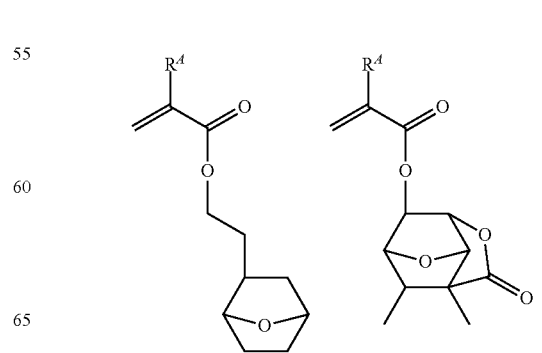

-continued
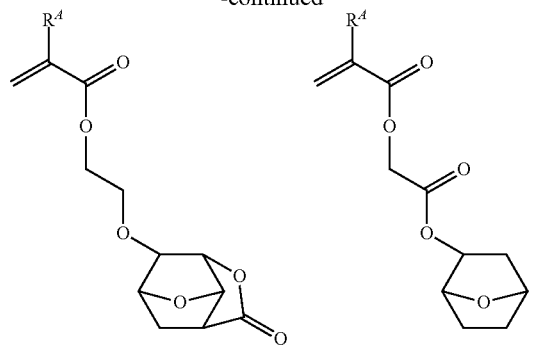
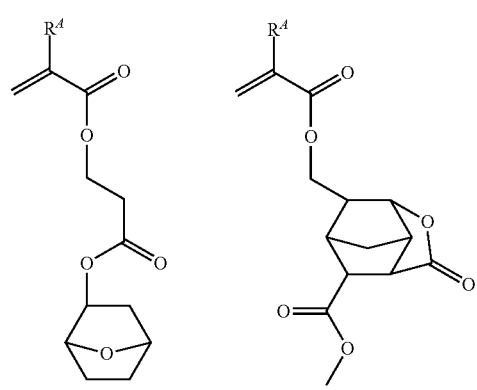
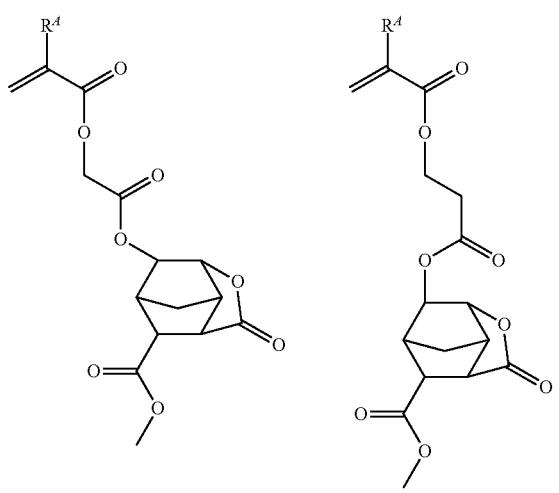
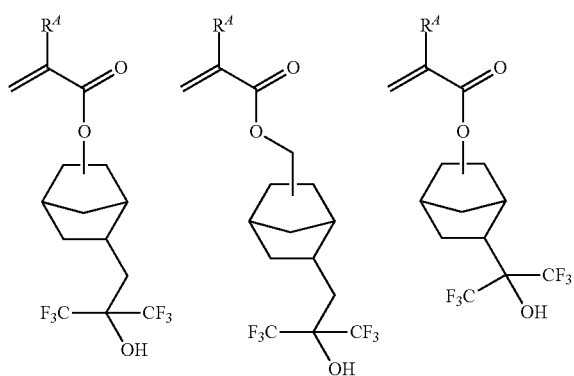
-continued
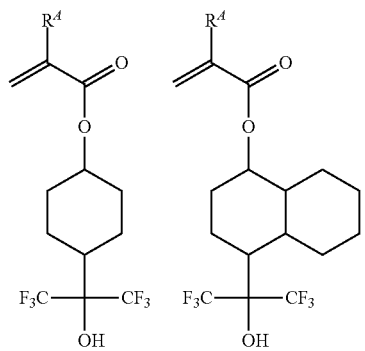
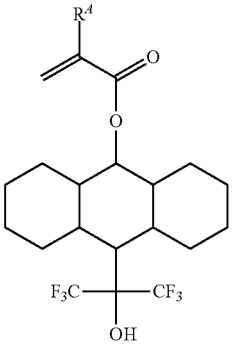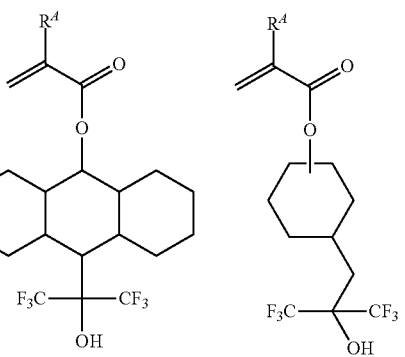
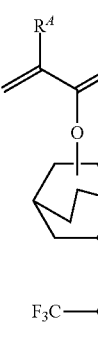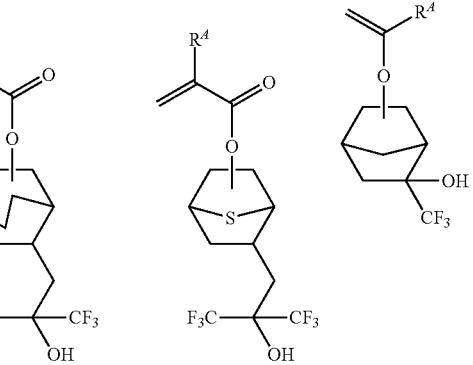
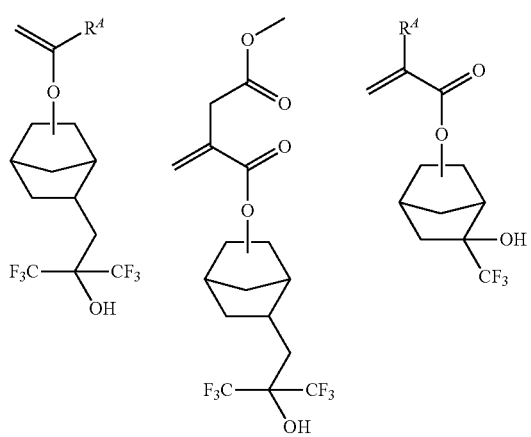

-continued
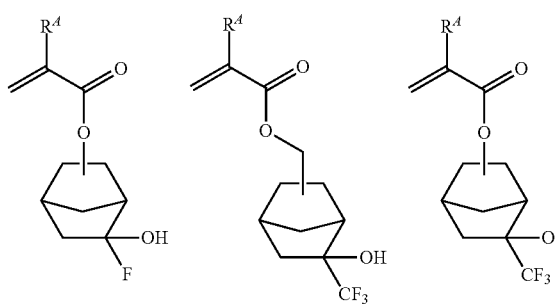
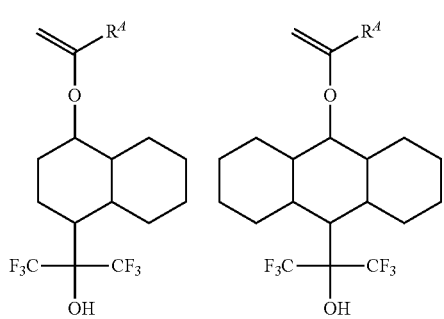
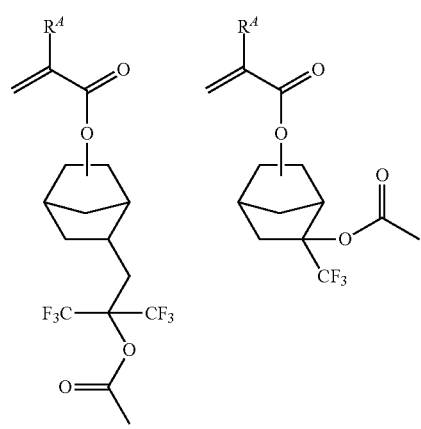
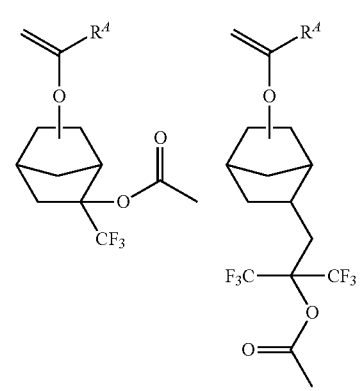
-continued
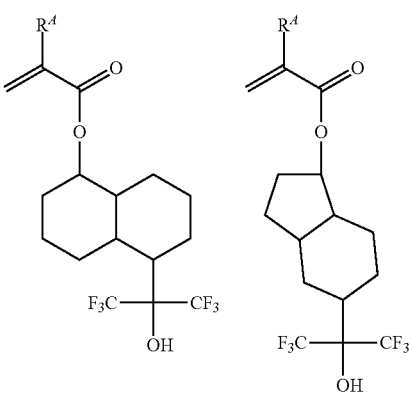
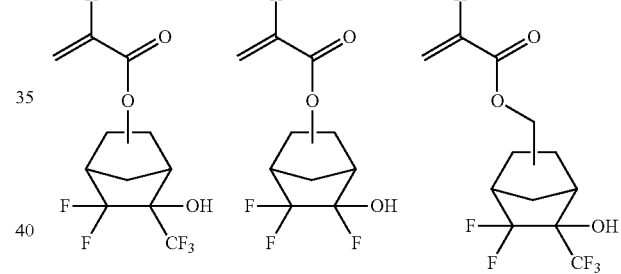
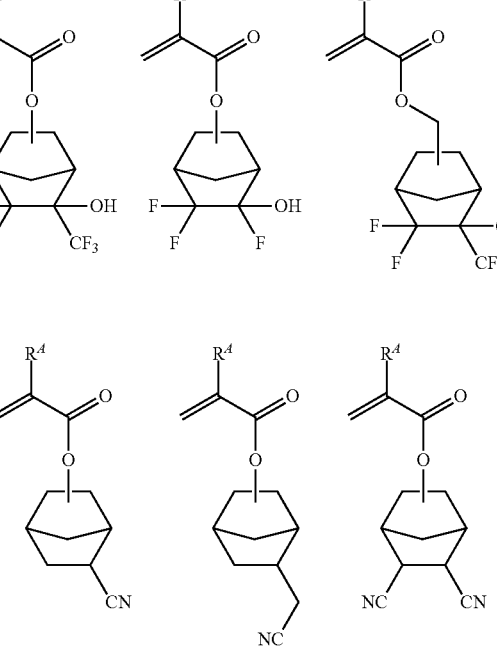
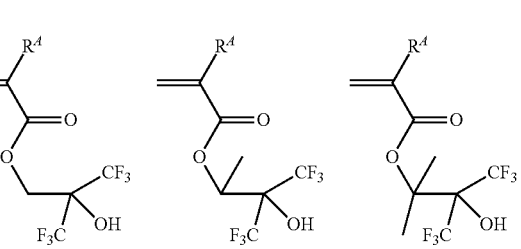

-continued
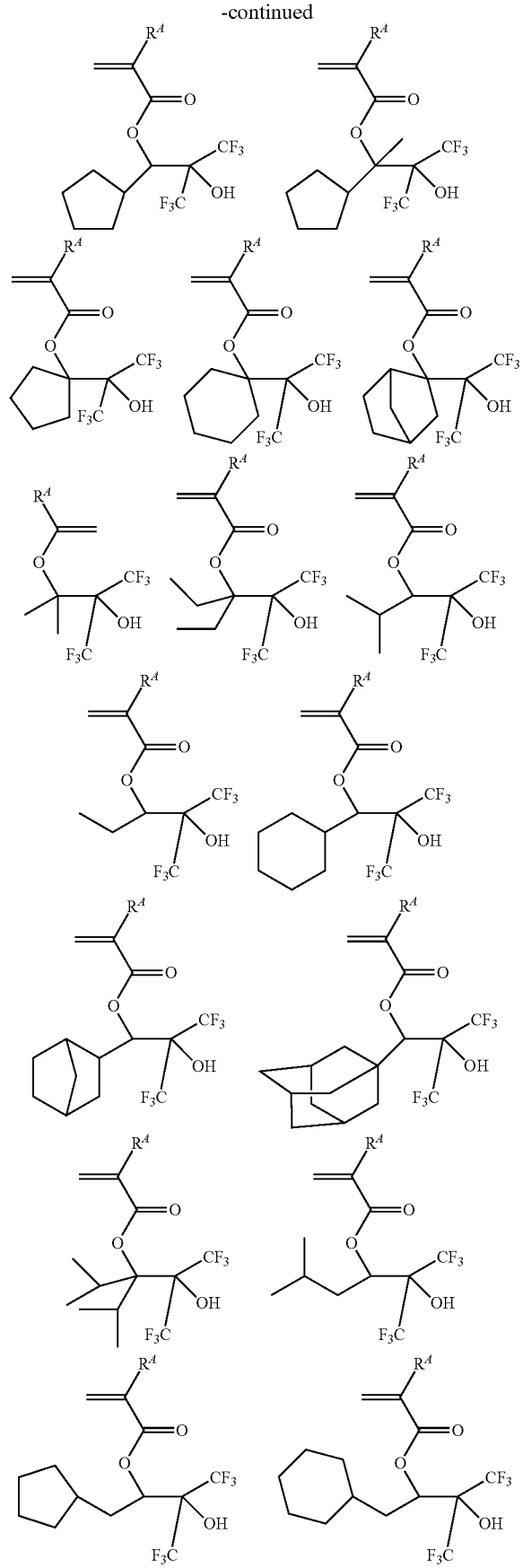
-continued
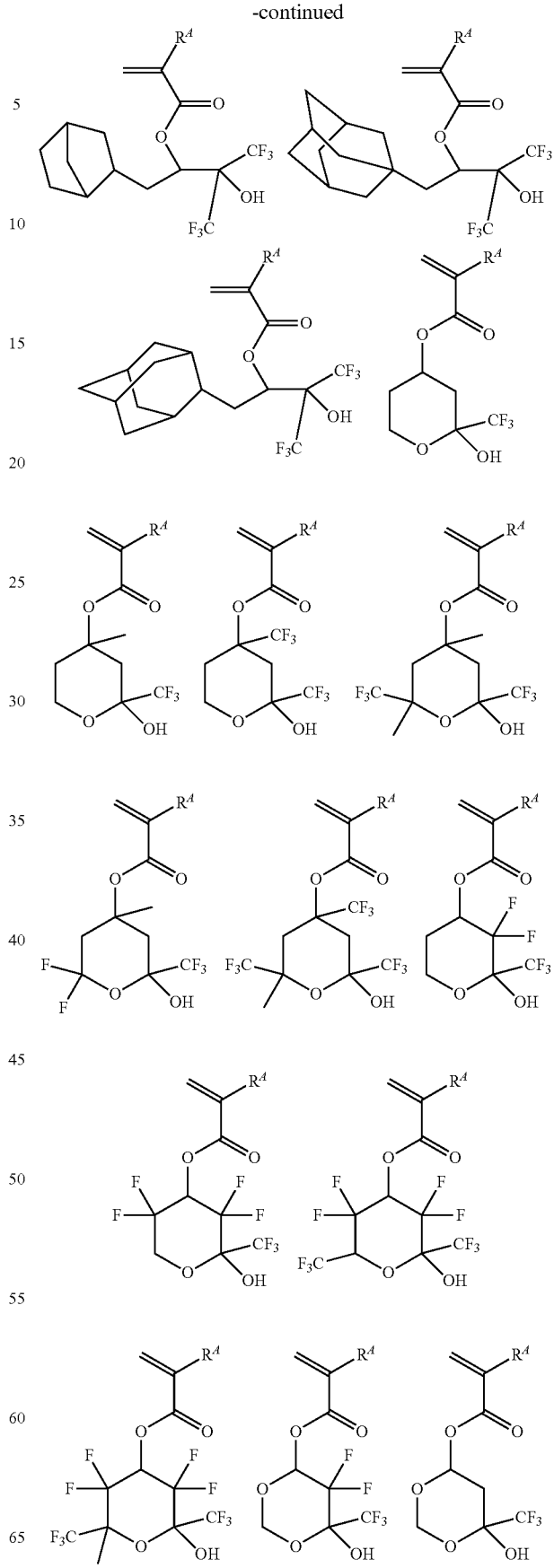

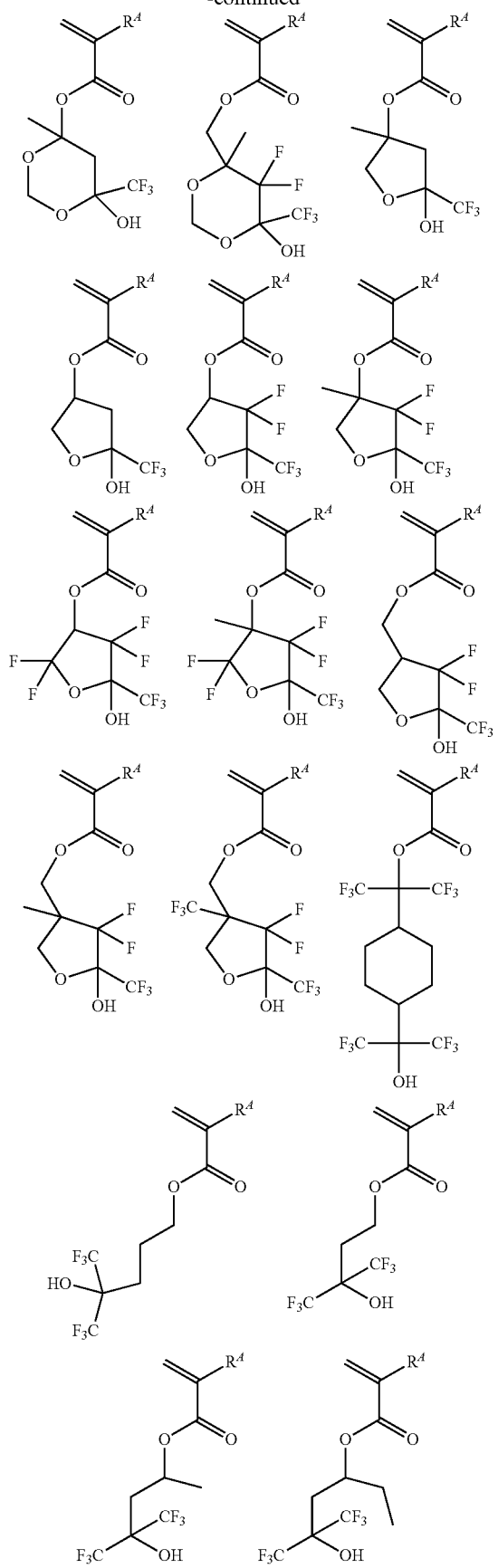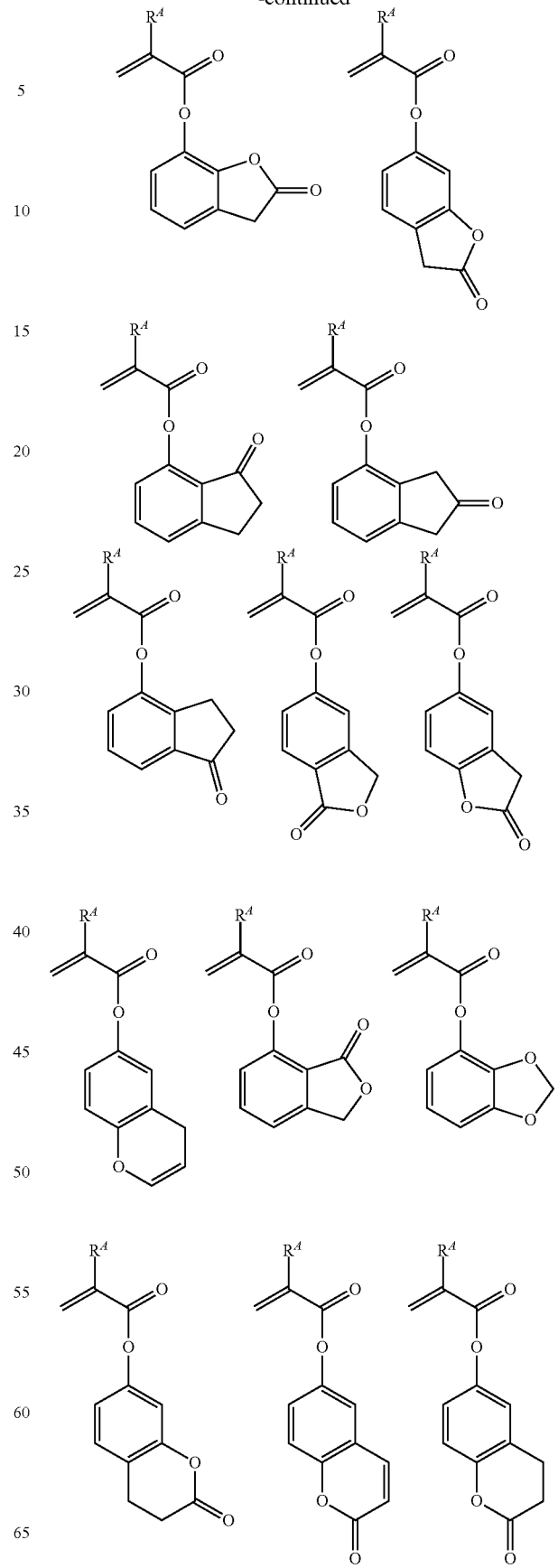

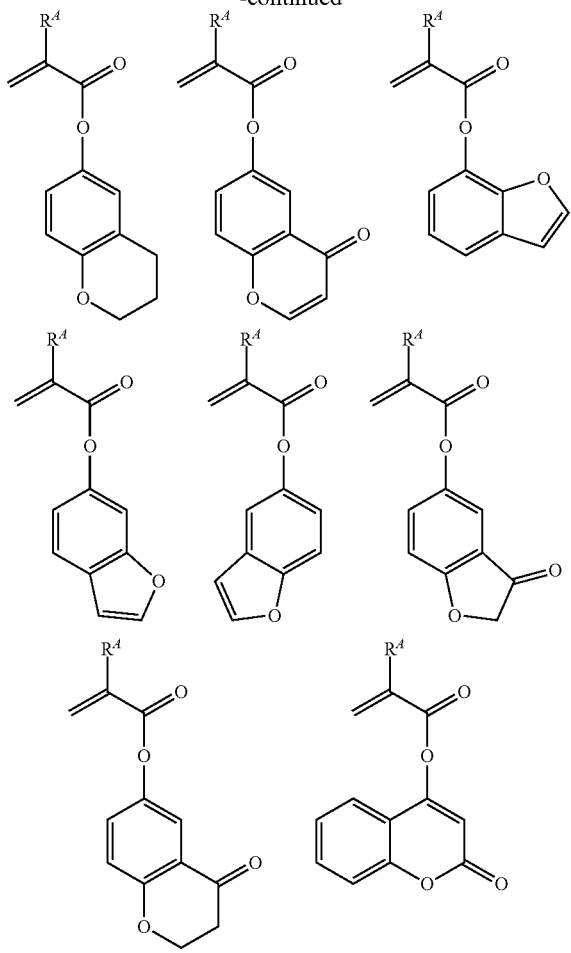
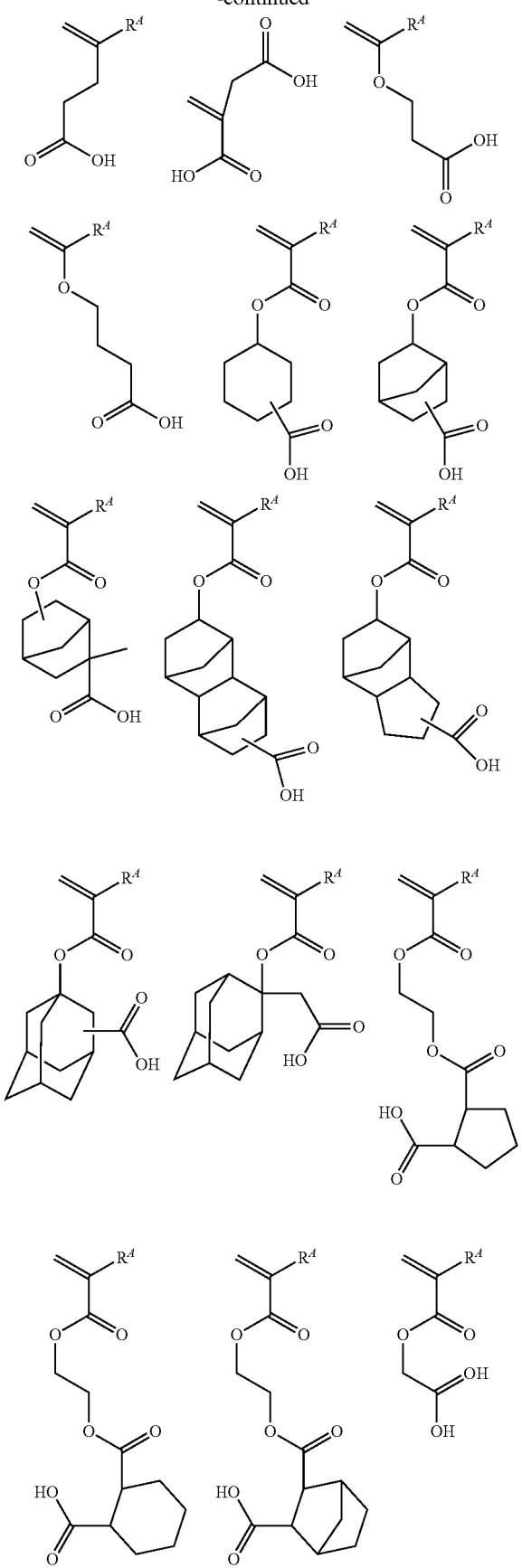

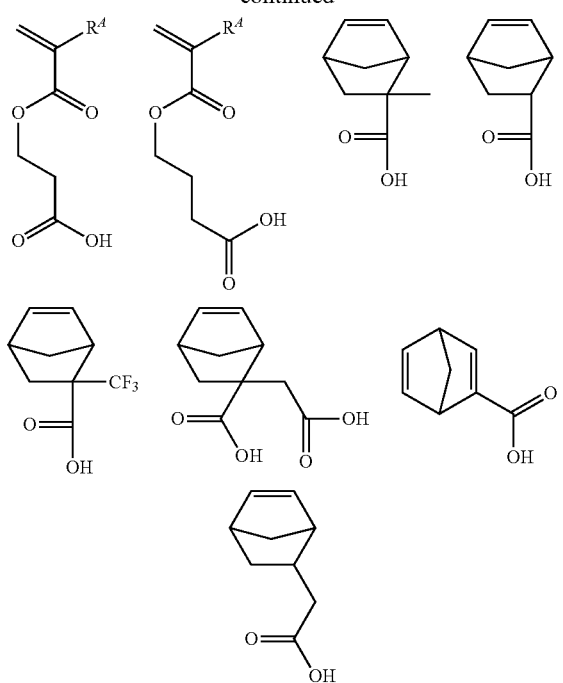

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

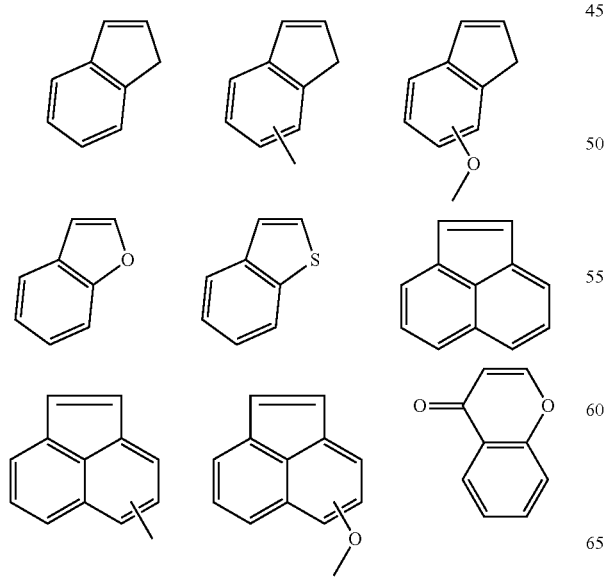

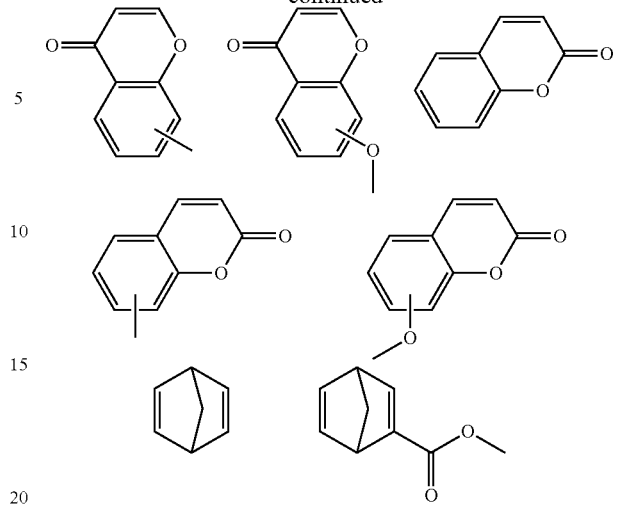

Besides the recurring units described above, further recurring units (e) may be incorporated in the base polymer, examples of which include styrene, vinylnaphthalene, vinylanthracene, vinylpyrene, methyleneindane, vinylpyridine, and vinylcarbazole.

In a further embodiment, recurring units (f) derived from an onium salt having a to polymerizable unsaturated bond may be incorporated in the base polymer. The preferred recurring units (f) include recurring units having formula (f1), recurring units having formula (f2), and recurring units having formula (f3). These units are simply referred to as recurring units (f1), (f2) and (f3), which may be used alone or in combination of two or more types.

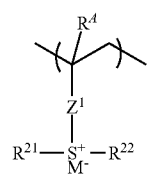
(f1)

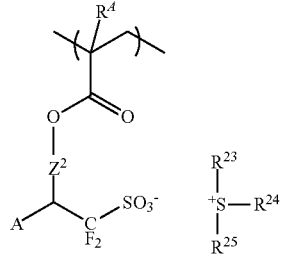
(f2)

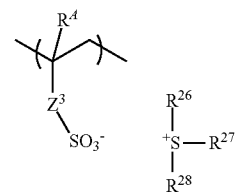
(f3)

Herein $R^A$ is each independently hydrogen or methyl. $Z^1$ is a single bond, phenylene group, —O—$Z^{12}$—, or —C(=O)—$Z^{11}$—$Z^{12}$—, wherein $Z^{11}$ is —O— or —NH— and $Z^{12}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety. $R^{21}$ to $R^{28}$ are each independently a $C_1$-$C_{12}$ straight, branched or cyclic alkyl group which may contain a carbonyl, ester or ether moiety, or a $C_6$-$C_{12}$ aryl group or $C_7$-$C_{20}$ aralkyl group, in which at least one hydrogen (i.e., one or more or even all hydrogen atoms) may be substituted by a $C_1$-$C_{10}$ straight, branched or cyclic alkyl moiety, halogen, trifluoromethyl, cyano, nitro, hydroxyl, mercapto, $C_1$-$C_{10}$ straight, branched or cyclic alkoxy moiety, $C_2$-$C_{10}$ straight, branched or cyclic alkoxycarbonyl moiety, or $C_2$-$C_{10}$ straight, branched or cyclic acyloxy moiety. Also, any two of $R^{23}$, $R^{24}$, and $R^{25}$, or any two of $R^{26}$, $R^{27}$ and $R^{28}$ may bond together to form a ring with the sulfur atom to which they are attached. $Z^2$ is a single bond, —$Z^{21}$—C(=O)—O—, —$Z^{21}$—O— or —$Z^{21}$—O—C(=O)—, wherein $Z^{21}$ is a straight, branched or cyclic $C_1$-$C_{12}$ alkylene group which may contain a carbonyl, ester or ether moiety. A is hydrogen or trifluoromethyl. $Z^3$ is a single bond, methylene group, ethylene group, phenylene group, fluorinated phenylene group, —O—$Z^{32}$—, or —C(=O)—$Z^{31}$—$Z^{32}$—, wherein $Z^{31}$ is —O— or —NH— and $Z^{32}$ is a $C_1$-$C_6$ straight, branched or cyclic alkylene group, phenylene, fluorinated phenylene, trifluoromethyl-substituted phenylene group, or $C_2$-$C_6$ straight, branched or cyclic alkenylene group, which may contain a carbonyl, ester, ether or hydroxyl moiety. $M^-$ is a non-nucleophilic counter ion.

Examples of the monomer from which recurring unit (f1) is derived are shown below, but not limited thereto. $R^A$ and $M^-$ are as defined above.

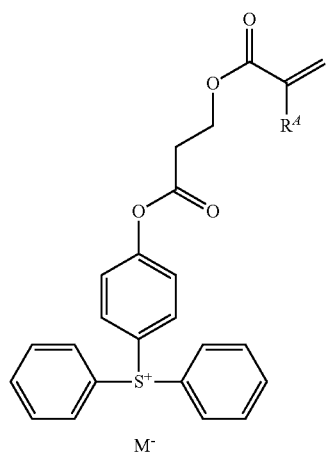

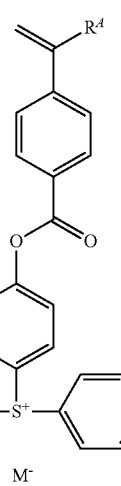

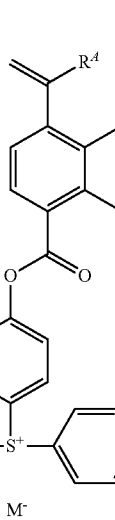

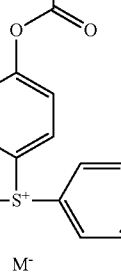

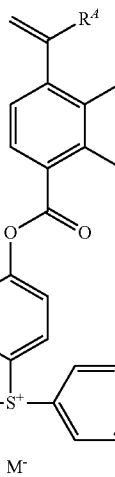

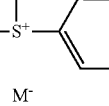

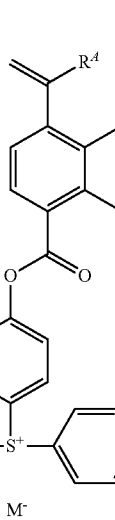

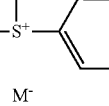

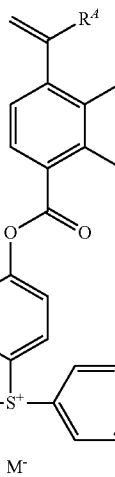

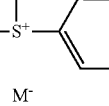

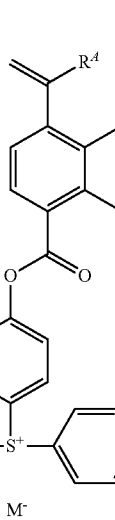

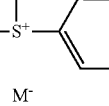

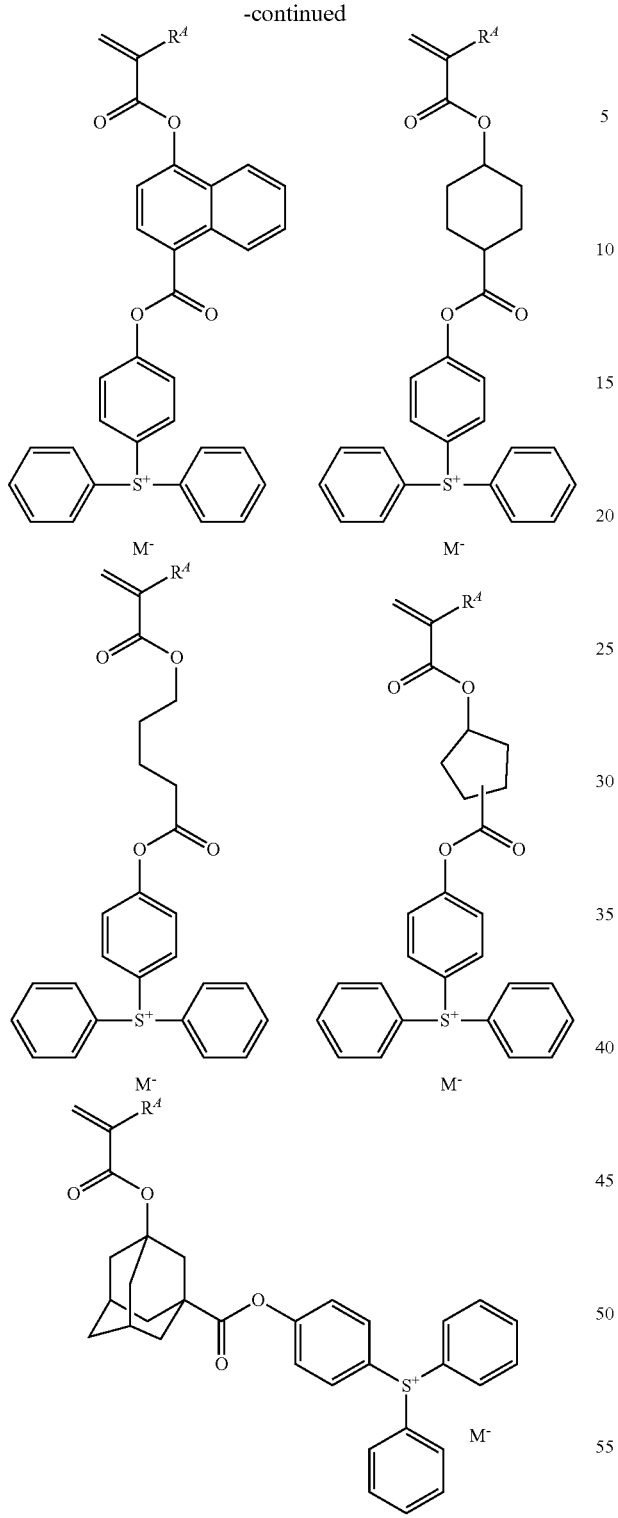

nyl)imide and bis(perfluorobutylsulfonyl)imide; methidates such as tris(trifluoromethylsulfonyl)methide and tris(perfluoroethylsulfonyl)methide.

Also included are sulfonates having fluorine substituted at α-position as represented by the formula (K-1) and sulfonates having fluorine substituted at α- and β-positions as represented by the formula (K-2).

(K-1)

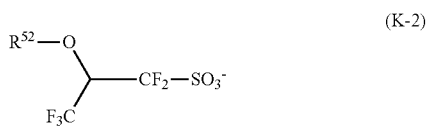

(K-2)

In formula (K-1), $R^{51}$ is hydrogen, or a $C_1$-$C_{20}$ straight, branched or cyclic alkyl group, $C_2$-$C_{20}$ straight, branched or cyclic alkenyl group, or $C_6$-$C_{20}$ aryl group, which may contain an ether, ester, carbonyl moiety, lactone ring, or fluorine atom. In formula (K-2), $R^{52}$ is hydrogen, or a $C_1$-$C_{30}$ straight, branched or cyclic alkyl group, $C_2$-$C_{20}$ straight, branched or cyclic acyl group, $C_2$-$C_{20}$ straight, branched or cyclic alkenyl group, $C_6$-$C_{20}$ aryl group or $C_6$-$C_{20}$ aryloxy group, which may contain an ether, ester, carbonyl moiety or lactone ring.

Examples of the monomer from which recurring unit (f2) is derived are shown below, but not limited thereto. $R^A$ is as defined above.

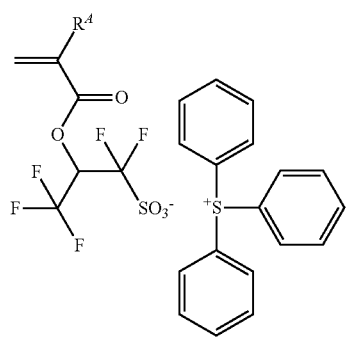

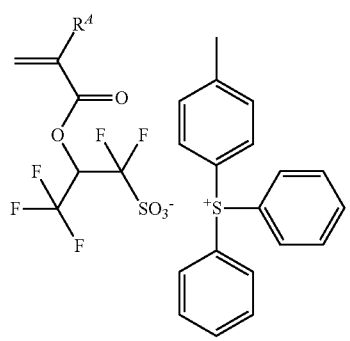

Examples of the non-nucleophilic counter ion M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfo- -continued
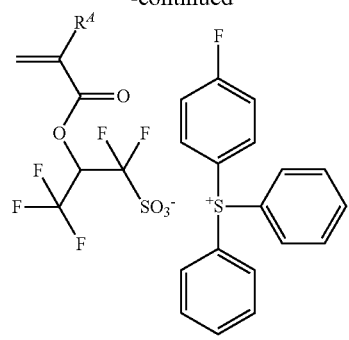
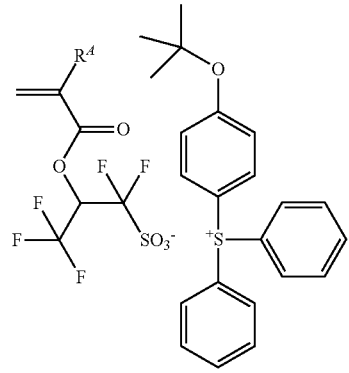
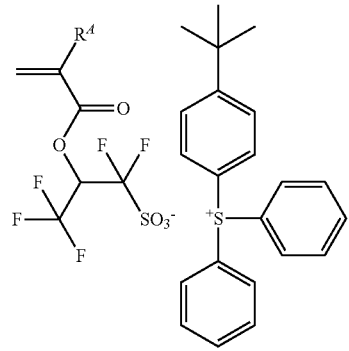
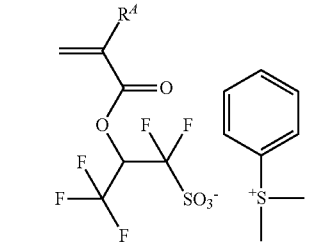
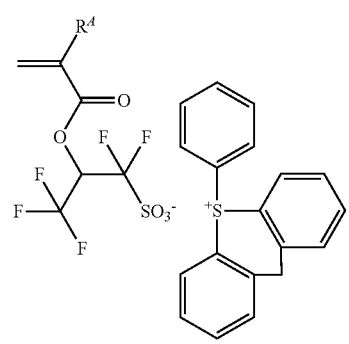
-continued
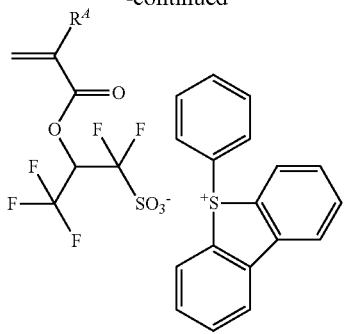
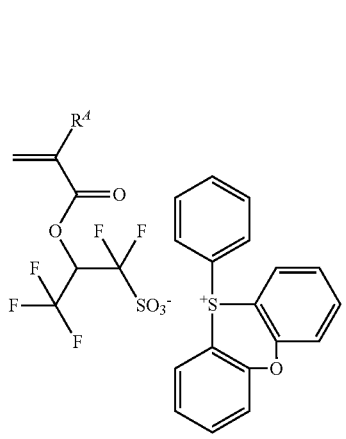
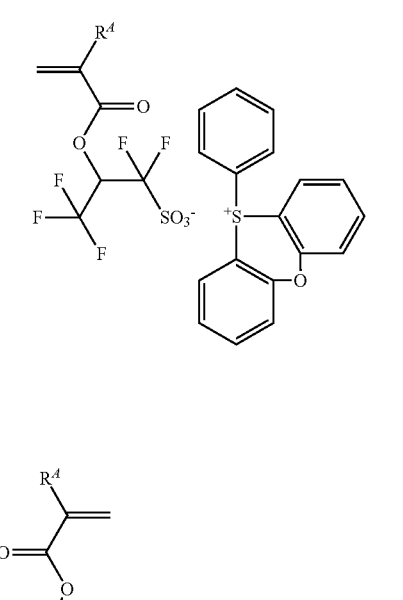
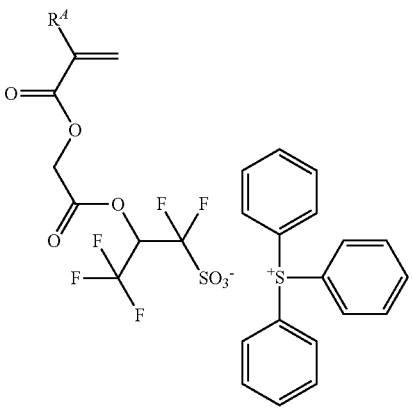
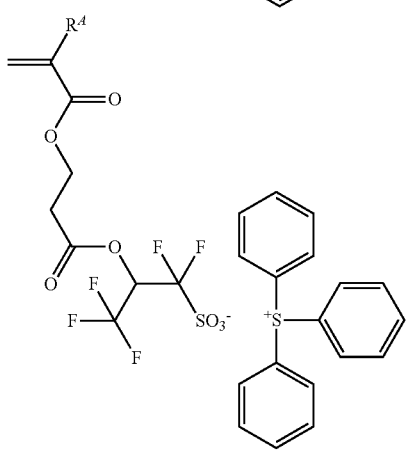

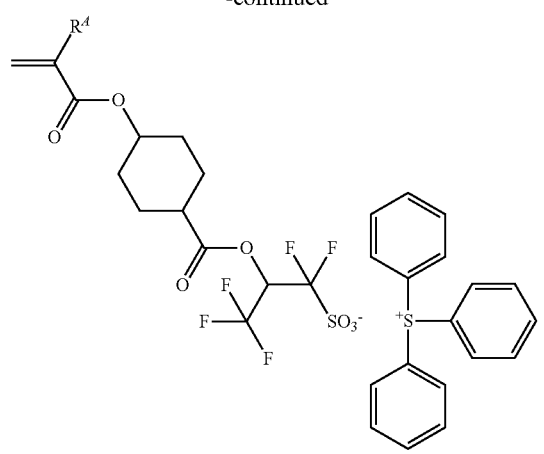
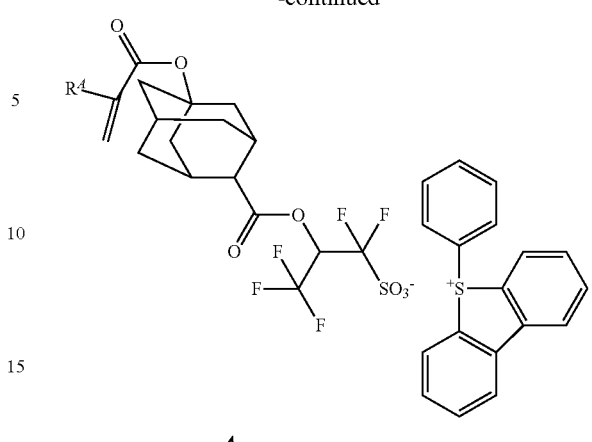
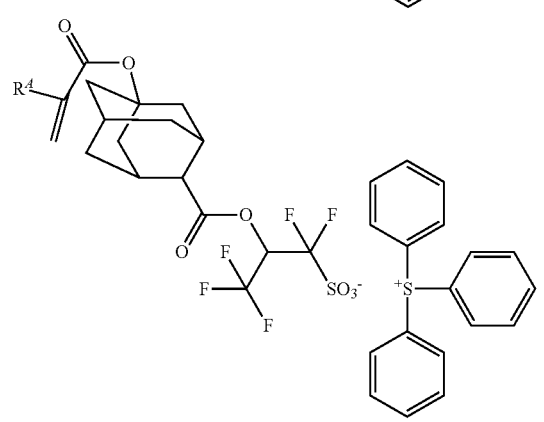
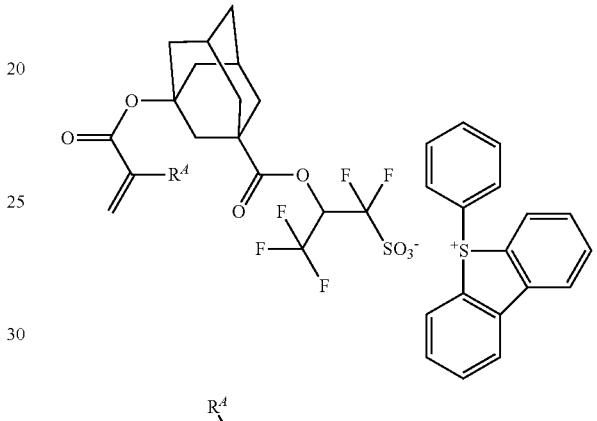
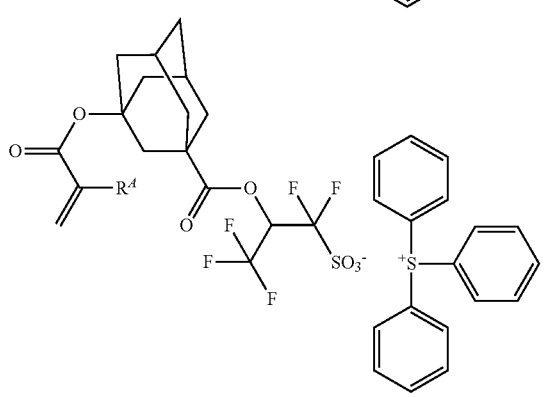
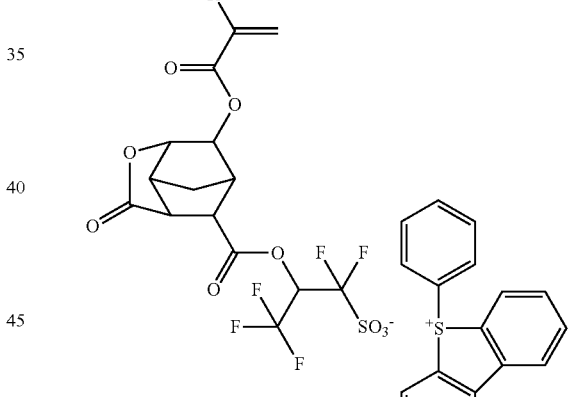
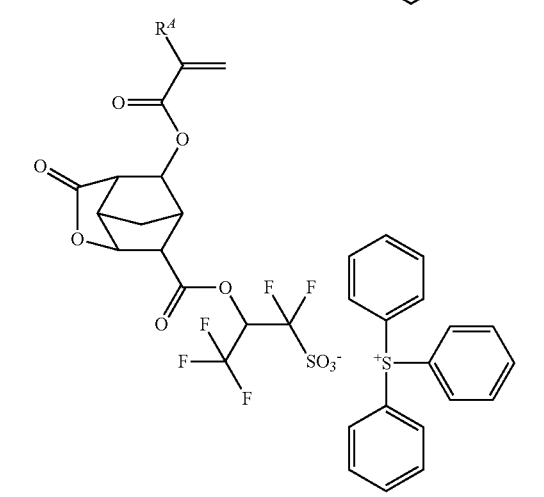
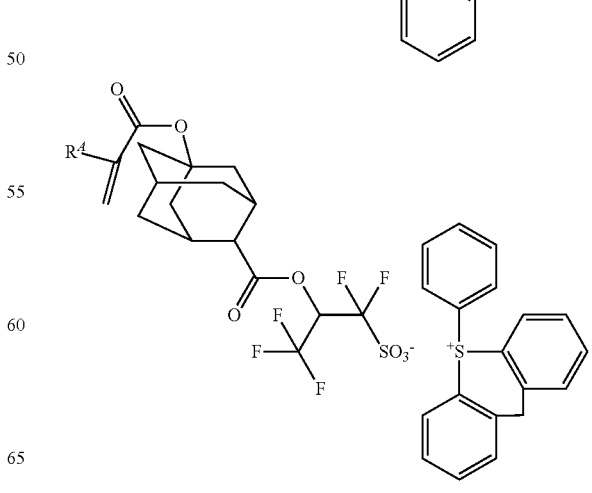

-continued
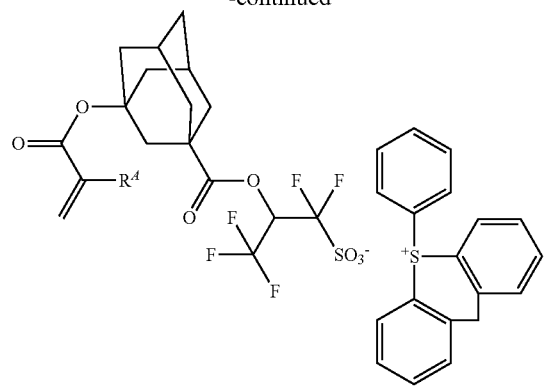
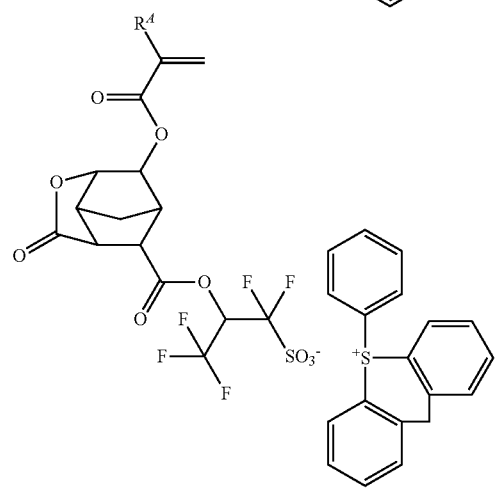
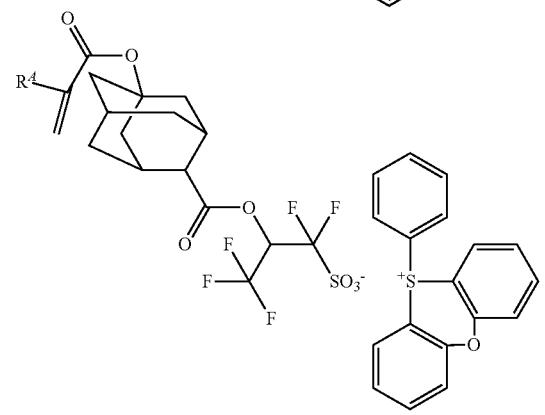
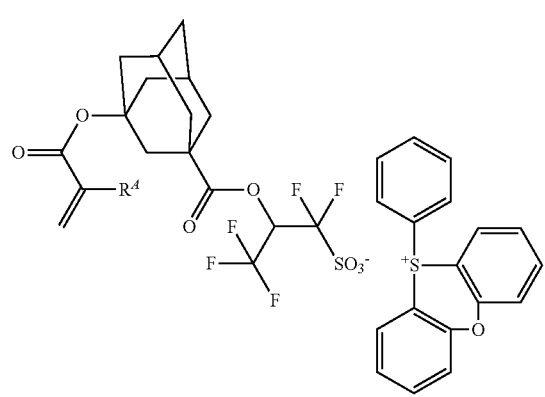
-continued
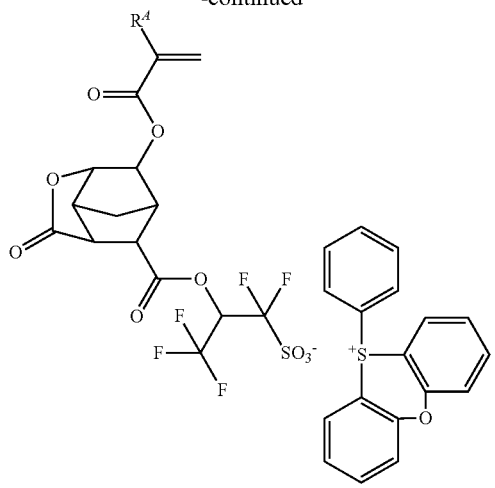
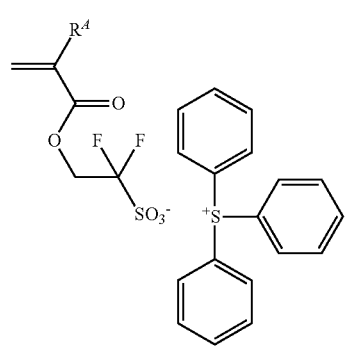
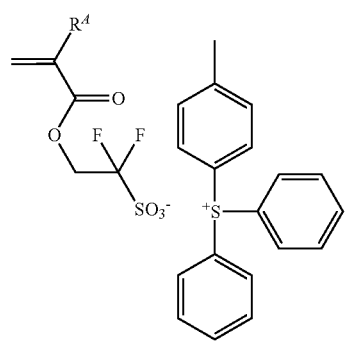
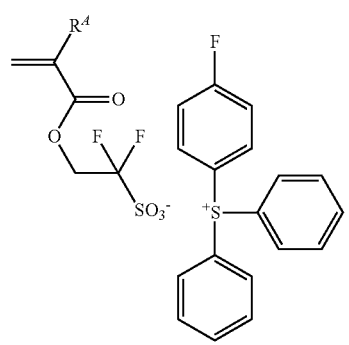

-continued
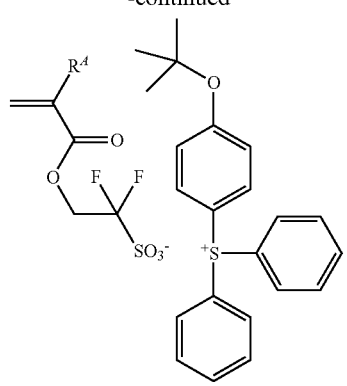
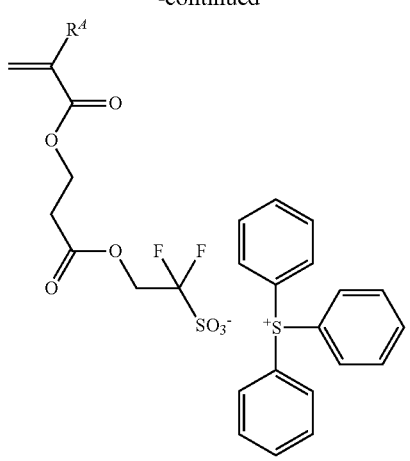
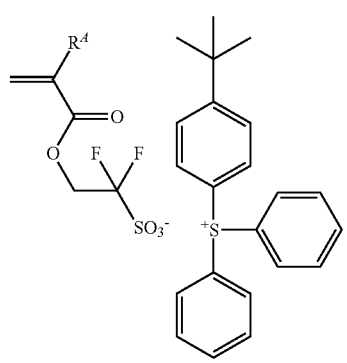
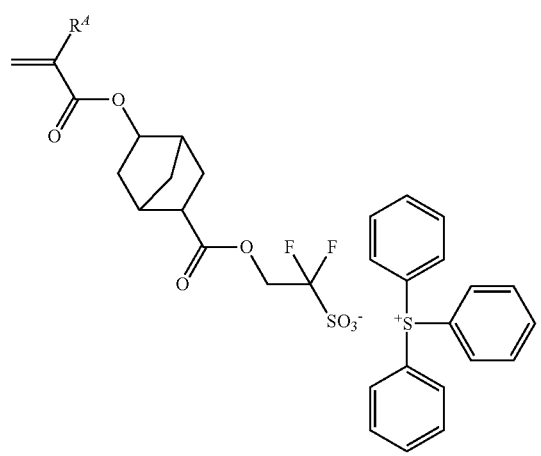
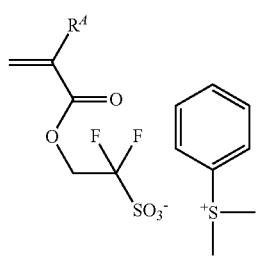
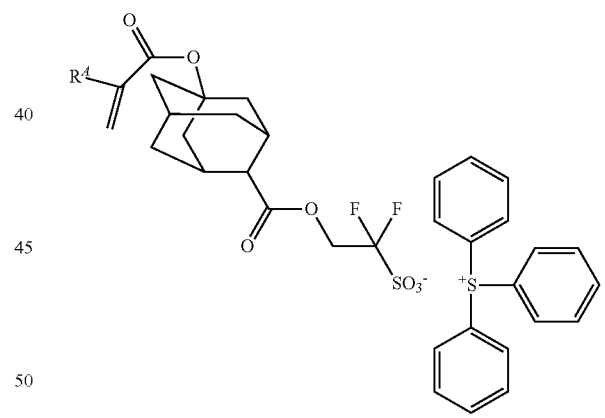
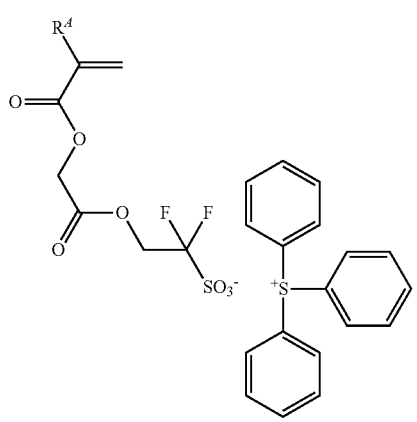
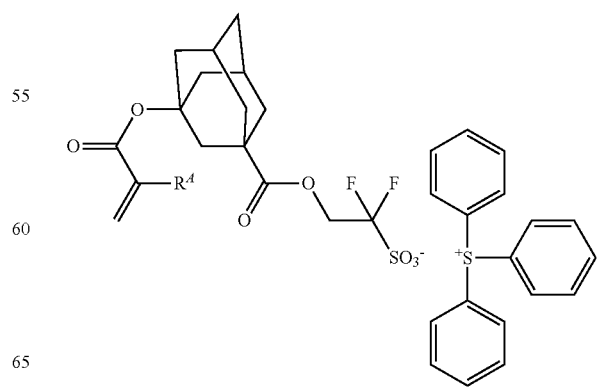

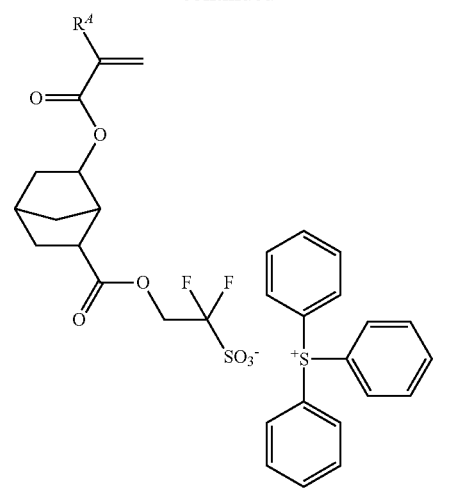
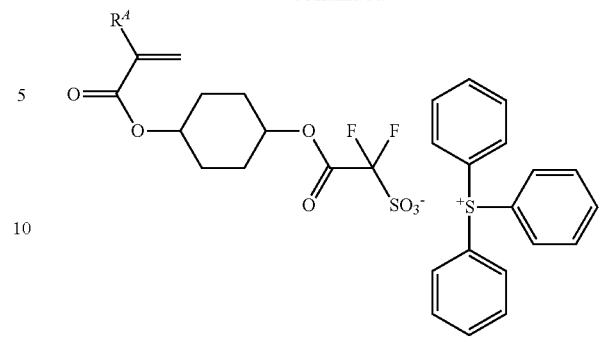
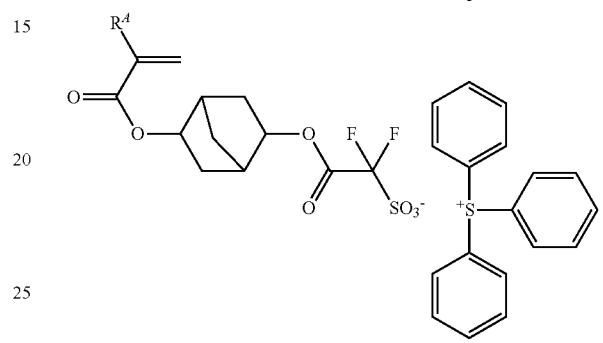
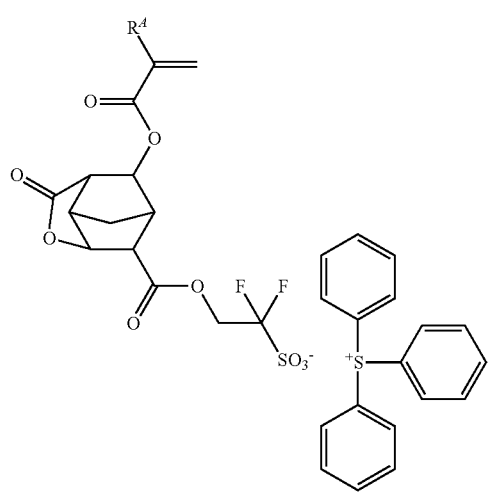
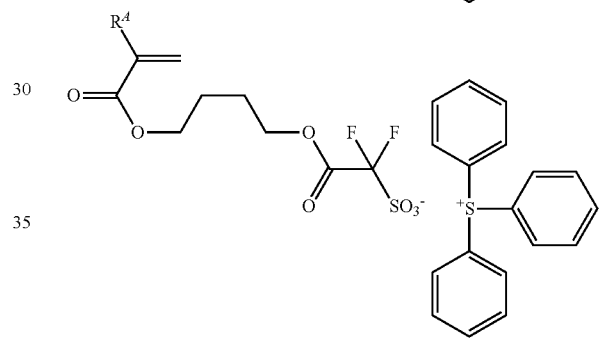
Examples of the monomer from which recurring unit (f3) is derived are shown below, but not limited thereto. $R^A$ is as defined above.
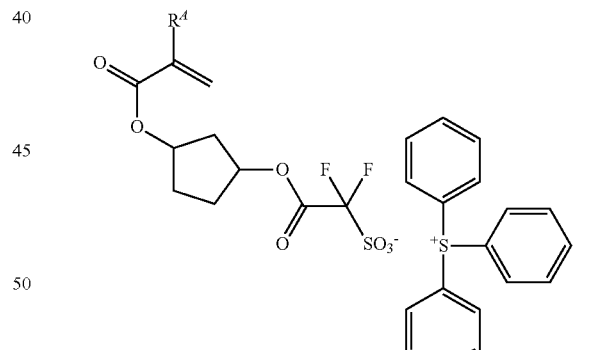
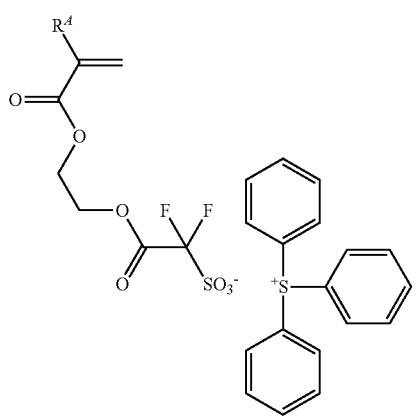
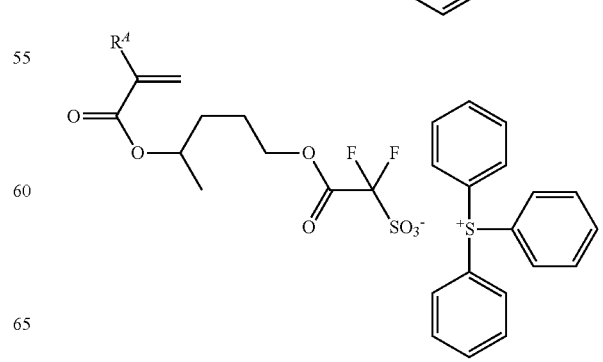

53
-continued
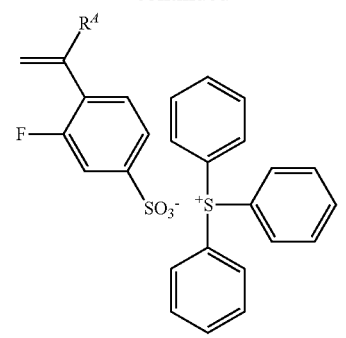
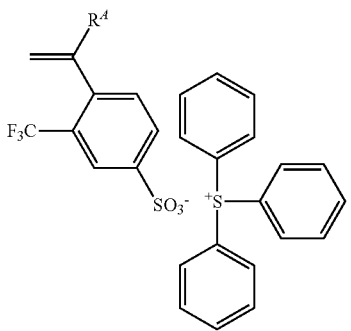
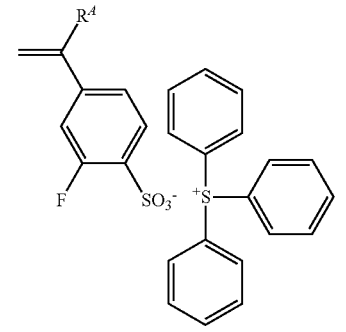
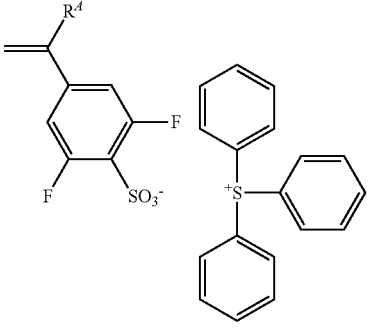
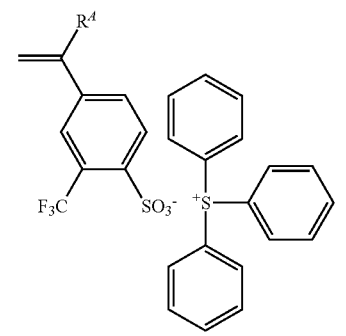
54
-continued
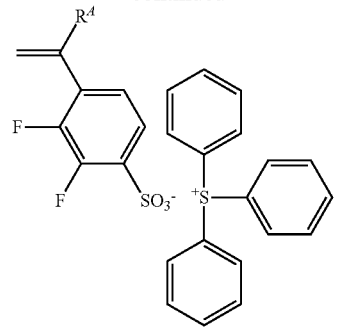
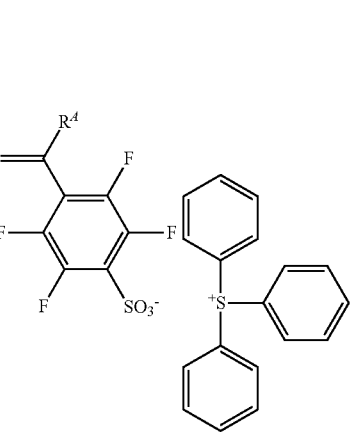
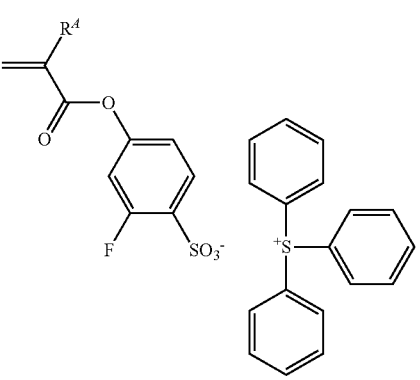
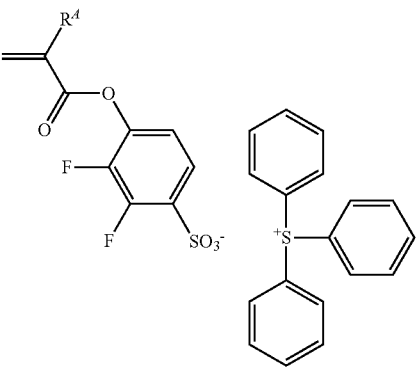

-continued

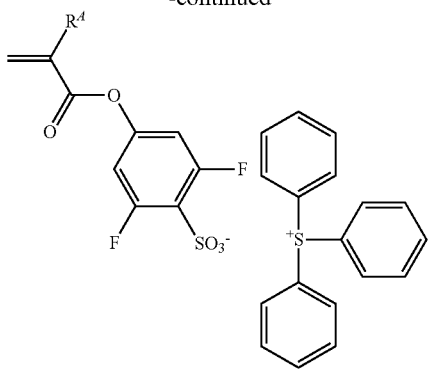

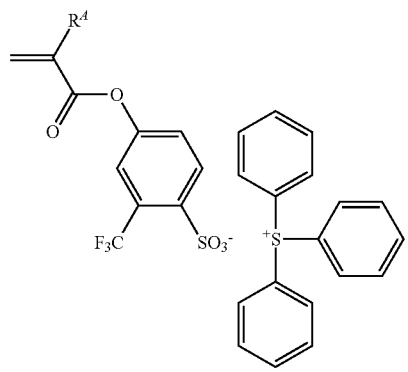

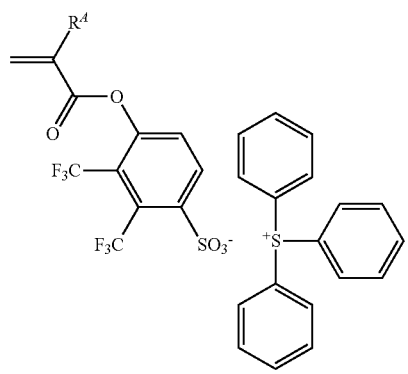

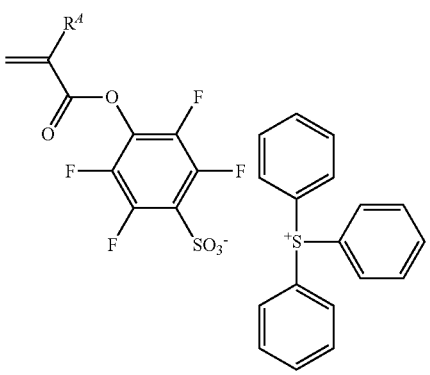

-continued

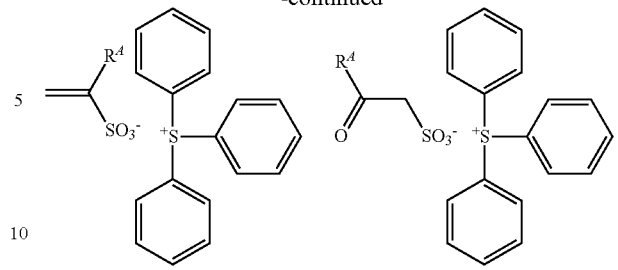

The attachment of an acid generator to the polymer main chain is effective in restraining acid diffusion, thereby preventing a reduction of resolution due to blur by acid diffusion. Also edge roughness is improved since the acid generator is uniformly distributed. Where a base polymer containing recurring units (f) is used, the addition of a separate PAG may be omitted.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \leq a1 < 1.0$, $0 \leq a2 < 1.0$, $0 < a1+a2 < 1.0$, $0 \leq b \leq 0.9$, to $0 \leq c \leq 0.9$, $0 \leq d \leq 0.8$, $0 \leq e \leq 0.8$, and $0 \leq f \leq 0.5$; more preferably $0 \leq a1 \leq 0.9$, $0 \leq a2 \leq 0.9$, $0.1 < a1+a2 \leq 0.9$, $0 \leq b \leq 0.8$, $0 \leq c \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, unit (f) is at least one of units (f1), (f2) and (f3), i.e., $f=f1+f2+f3$, and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \leq 1.0$, $0 \leq c \leq 0.9$, $0 \leq d \leq 0.8$, $0 \leq e \leq 0.8$, and $0 \leq f \leq 0.5$; more preferably $0.2 \leq b \leq 1.0$, $0 \leq c \leq 0.8$, $0 \leq d \leq 0.7$, $0 \leq e \leq 0.7$, and $0 \leq f \leq 0.4$; and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, unit (f) is at least one of units (f1), (f2) and (f3), i.e., $f=f1+f2+f3$, and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and effecting heat polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Acid Generator

To the resist composition comprising the base polymer and the iodonium salt having formula (A), an acid generator may be added so that the composition may function as a chemically amplified positive or negative resist composition. The acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880).

As the PAG used herein, those having the formula (1) are preferred.

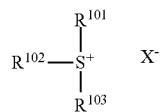

(1)

In formula (1), $R^{101}$, $R^{102}$ and $R^{103}$ are each independently a $C_1$-$C_{20}$ straight, branched or cyclic monovalent hydrocarbon group which may contain a heteroatom. Any two of $R^{101}$, $R^{102}$ and $R^{103}$ may bond together to form a ring with the sulfur atom to which they are attached.

In formula (1), $X^-$ is an anion of the following formula (1A), (1B), (1C) or (1D).

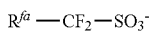

(1A)

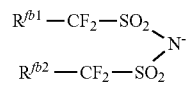

(1B)

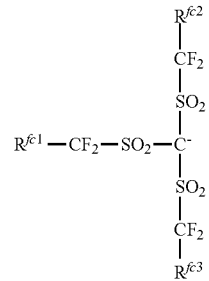

(1C)

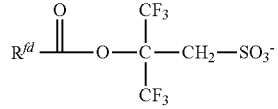

(1D)

In formula (1A), $R^{fa}$ is fluorine or a $C_1$-$C_{40}$ straight, branched or cyclic monovalent hydrocarbon group which may contain a heteroatom.

Of the anions of formula (1A), an anion having the formula (1A') is preferred.

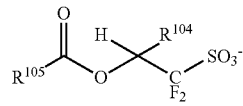

(1A')

In formula (1A'), $R^{104}$ is hydrogen or trifluoromethyl, preferably trifluoromethyl. $R^{105}$ is a $C_1$-$C_{38}$ straight, branched or cyclic monovalent hydrocarbon group which may contain a heteroatom. As the heteroatom, oxygen, nitrogen, sulfur and halogen atoms are preferred, with oxygen being most preferred. Of the monovalent hydrocarbon groups represented by $R^{105}$, those groups of 6 to 30 carbon atoms are preferred from the aspect of achieving a high resolution in forming patterns of fine feature size. Suitable monovalent hydrocarbon groups include, but are not limited to, methyl, ethyl, propyl, isopropyl, butyl, isobutyl, s-butyl, t-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, one or more hydrogen atoms may be substituted by a moiety containing a heteroatom such as oxygen, sulfur, nitrogen or halogen, or one or more carbon atoms may be substituted by a moiety containing a heteroatom such as oxygen, sulfur or nitrogen, so that the group may contain a hydroxyl, cyano, carbonyl, ether, ester, sulfonic acid ester, carbonate, lactone ring, sultone ring, carboxylic anhydride or haloalkyl moiety.

With respect to the synthesis of the sulfonium salt having an anion of formula (1A'), reference may be made to JP-A 2007-145797, JP-A 2008-106045, JP-A 2009-007327, and JP-A 2009-258695. Also useful are the sulfonium salts described in JP-A 2010-215608, JP-A 2012-041320, JP-A 2012-106986, and JP-A 2012-153644.

Examples of the sulfonium salt having an anion of formula (1A) are shown below, but not limited thereto.
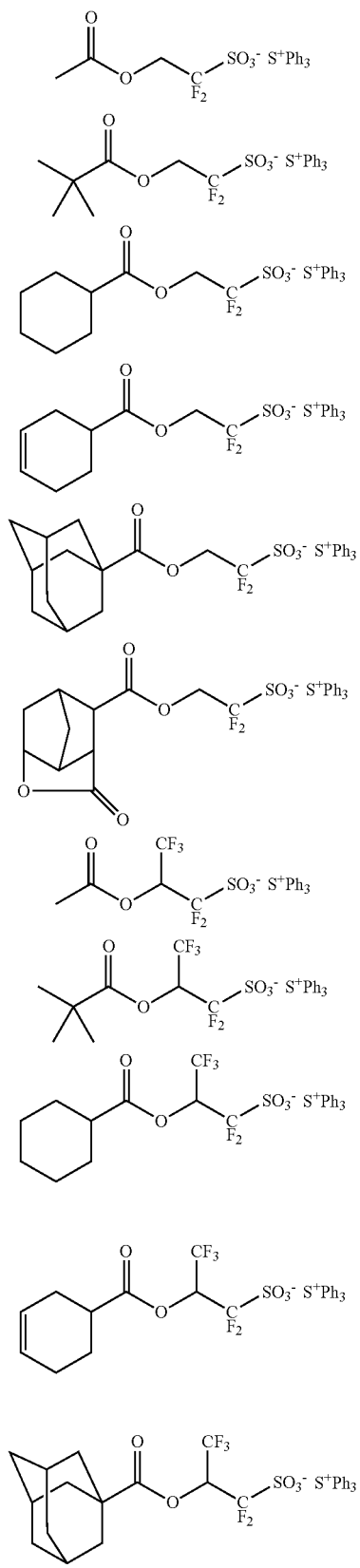
-continued
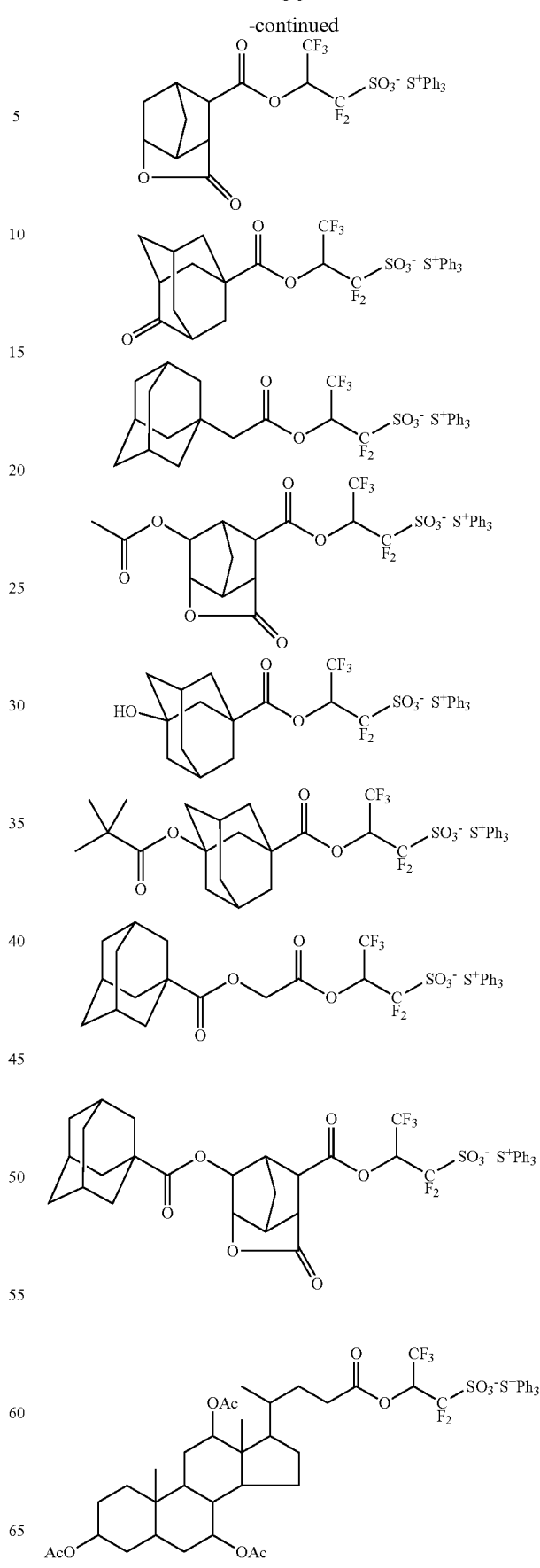

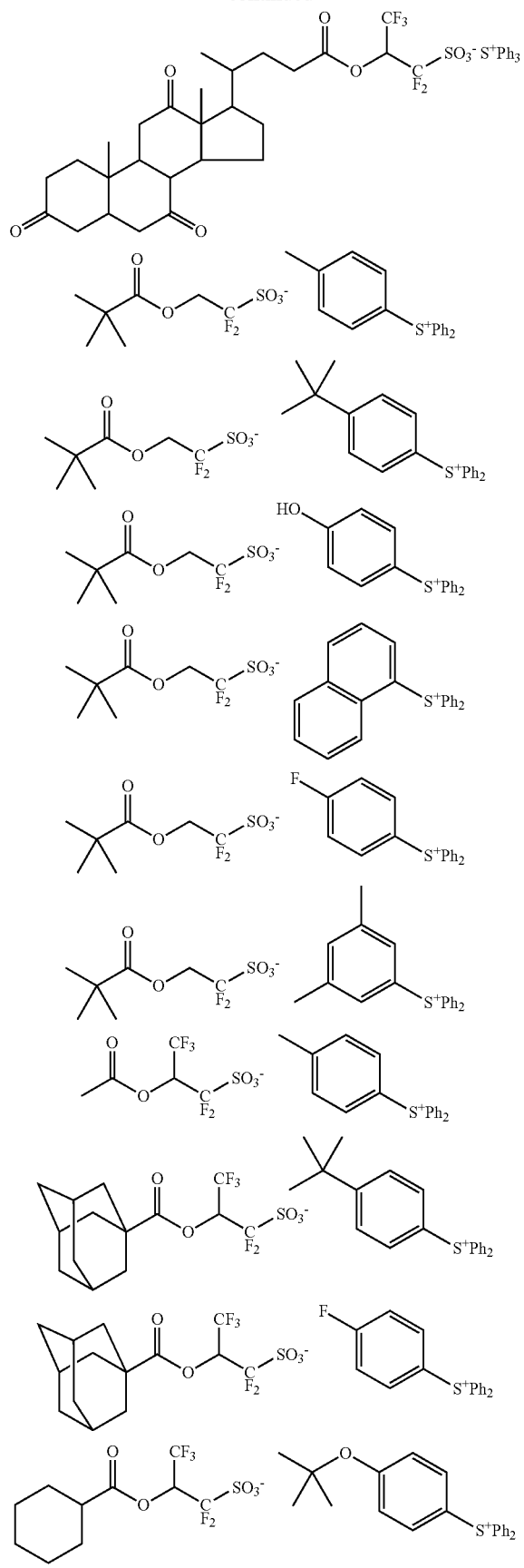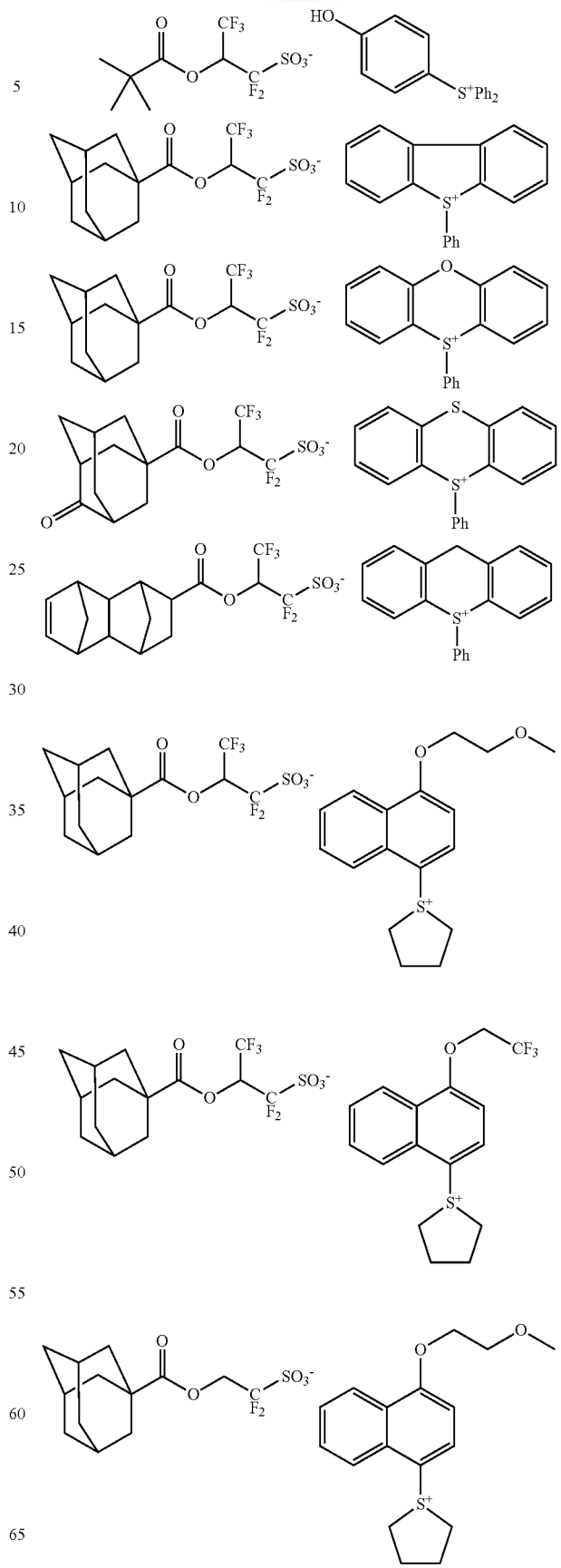

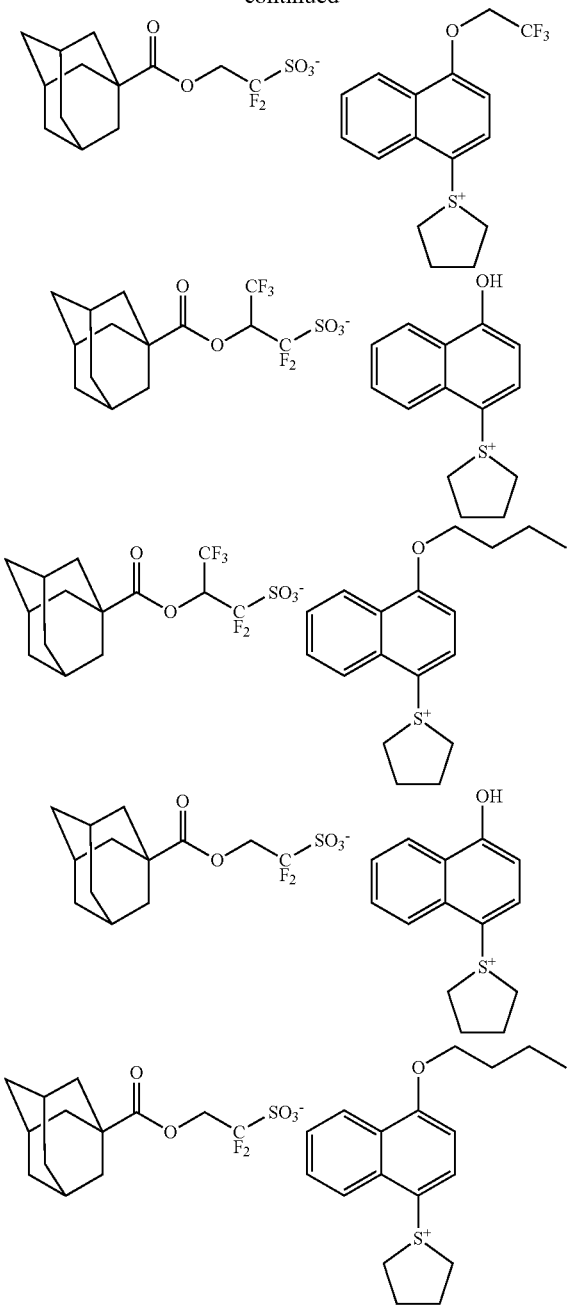

and $R^{fc3}$ are fluorine or $C_1$-$C_4$ straight fluorinated alkyl groups. Also, $R^{fc1}$ and $R^{fc2}$ may bond together to form a ring with the linkage: —$CF_2$—$SO_2$—$C^-$—$SO_2$—$CF_2$— to which they are attached. It is preferred to form a ring structure via a fluorinated ethylene or fluorinated propylene group.

In formula (1D), $R^{fd}$ is a $C_1$-$C_{40}$ straight, branched or cyclic monovalent hydrocarbon group which may contain a heteroatom. Illustrative examples of the monovalent hydrocarbon group are as exemplified for $R^{105}$.

With respect to the synthesis of the sulfonium salt having an anion of formula (1D), reference may be made to JP-A 2010-215608 and JP-A 2014-133723.

Examples of the sulfonium salt having an anion of formula (1D) are shown below, but not limited thereto.

In formula (1B), $R^{fb1}$ and $R^{fb2}$ are each independently fluorine or a $C_1$-$C_{40}$ straight, branched or cyclic monovalent hydrocarbon group which may contain a heteroatom. Illustrative examples of the monovalent hydrocarbon group are as exemplified for $R^{105}$. Preferably $R^{fb1}$ and $R^{fb2}$ are fluorine or $C_1$-$C_4$ straight fluorinated alkyl groups. Also, $R^{fb1}$ and $R^{fb2}$ may bond together to form a ring with the linkage: —$CF_2$—$SO_2$—$N^-$—$SO_2$—$CF_2$— to which they are attached. It is preferred to form a ring structure via a fluorinated ethylene or fluorinated propylene group.

In formula (1C), $R^{fc1}$, $R^{fc2}$ and $R^{fc3}$ are each independently fluorine or a $C_1$-$C_{40}$ straight, branched or cyclic monovalent hydrocarbon group which may contain a heteroatom. Illustrative examples of the monovalent hydrocarbon group are as exemplified for $R^{105}$. Preferably $R^{fc1}$, $R^{fc2}$ -continued

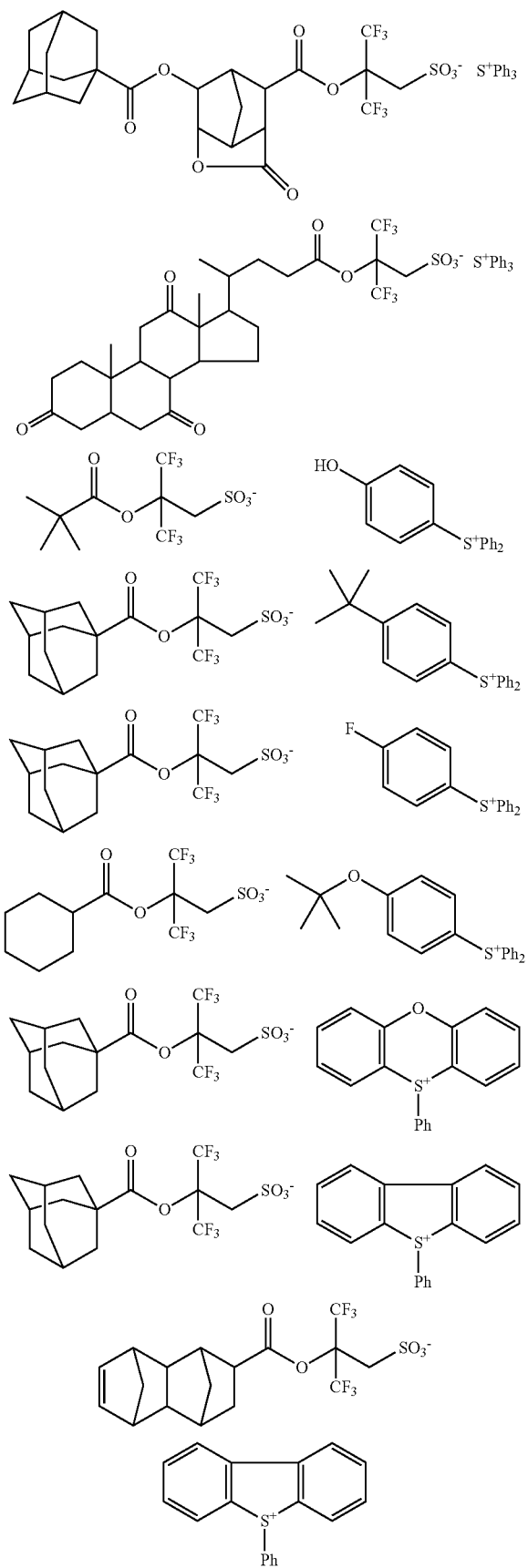

-continued

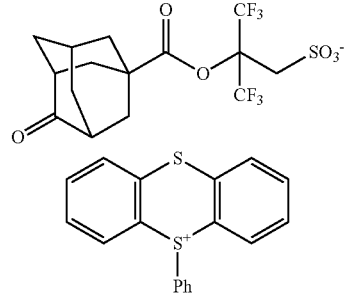

Notably, the compound having the anion of formula (1D) does not have fluorine at the α-position relative to the sulfo group, but two trifluoromethyl groups at the β-position. For this reason, it has a sufficient acidity to sever the acid labile groups in the resist polymer. Thus the compound is an effective PAG.

Another preferred PAG is a compound having the formula (2).

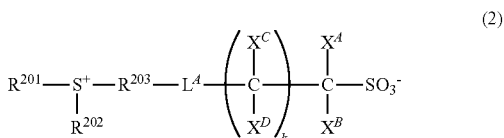
(2)

In formula (2), $R^{201}$ and $R^{202}$ are each independently a $C_1$-$C_{30}$ straight, branched or cyclic monovalent hydrocarbon group which may contain a heteroatom. $R^{203}$ is a $C_1$-$C_{30}$ straight, branched or cyclic divalent hydrocarbon group which may contain a heteroatom. Any two of $R^{201}$, $R^{202}$ and $R^{203}$ may bond together to form a ring with the sulfur atom to which they are attached. $L^A$ is a single bond, ether bond or a $C_1$-$C_{20}$ straight, branched or cyclic divalent hydrocarbon group which may contain a heteroatom. $X^A$, $X^B$, $X^C$ and $X^D$ are each independently hydrogen, fluorine or trifluoromethyl, with the proviso that at least one of $X^A$, $X^B$, $X^C$ and $X^D$ is fluorine or trifluoromethyl, and k is an integer of 0 to 3.

Examples of the monovalent hydrocarbon group include methyl, ethyl, propyl, isopropyl, n-butyl, s-butyl, t-butyl, n-pentyl, t-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2,6}$]decanyl, adamantyl, phenyl, naphthyl and anthracenyl. In these groups, one or more hydrogen atoms may be substituted by a heteroatom such as oxygen, sulfur, nitrogen or halogen, or one or more carbon atoms may be substituted by a moiety containing a heteroatom such as oxygen, sulfur or nitrogen, so that the group may contain a hydroxyl, cyano, carbonyl, ether, ester, sulfonic acid ester, carbonate, lactone ring, sultone ring, carboxylic anhydride or haloalkyl moiety.

Suitable divalent hydrocarbon groups include straight alkane-diyl groups such as methylene, ethylene, propane-1, 3-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; saturated cyclic divalent hydrocarbon groups such as cyclopentanediyl, cyclohexanediyl, norbornanediyl and adamantanediyl; and unsaturated cyclic divalent hydrocarbon groups such as phenylene and naphthylene. In these groups, one or more hydrogen atoms may be replaced by an alkyl moiety such as methyl, ethyl, propyl, n-butyl or t-butyl; one or more hydrogen atoms may be replaced by a moiety containing a heteroatom such as oxygen, sulfur, nitrogen or halogen; or one or more carbon atoms may be substituted by a moiety containing a heteroatom such as oxygen, sulfur or nitrogen, so that the group may contain a hydroxyl, cyano, carbonyl, ether, ester, sulfonic acid ester, carbonate, lactone ring, sultone ring, carboxylic anhydride or haloalkyl moiety. Of the heteroatoms, oxygen is preferred.

Of the PAGs having formula (2), those having formula (2') are preferred.

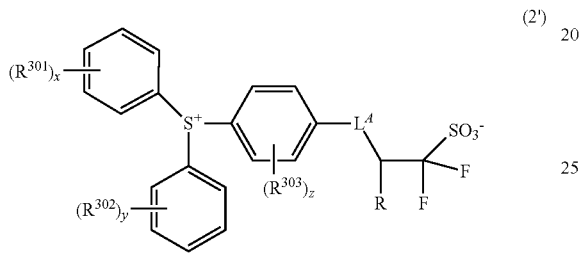

(2')

In formula (2'), $L^A$ is as defined above. R is hydrogen or trifluoromethyl, preferably trifluoromethyl. $R^{301}$, $R^{302}$ and $R^{303}$ are each independently hydrogen, hydroxyl, cyano, haloalkyl, or a $C_1$-$C_{20}$ straight, branched or cyclic monovalent hydrocarbon group which may contain a heteroatom. Suitable monovalent hydrocarbon groups are as described above for $R^{105}$. The subscripts x and y are each independently an integer of 0 to 5, and z is an integer of 0 to 4.

Examples of the PAG having formula (2) are shown below, but not limited thereto. Notably, R is as defined above.

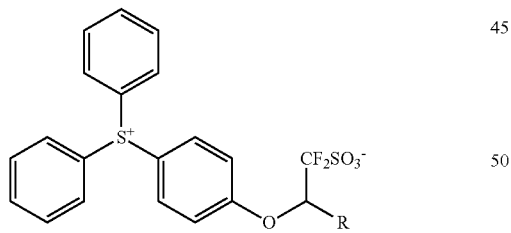

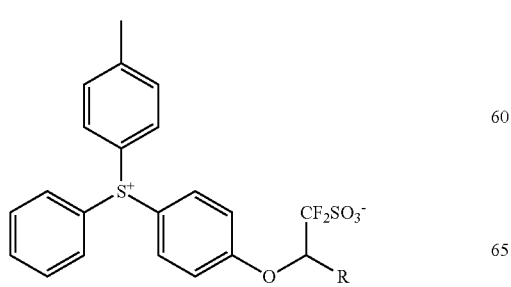

-continued

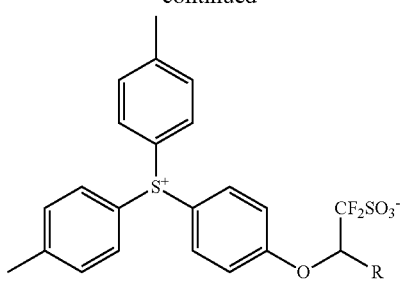

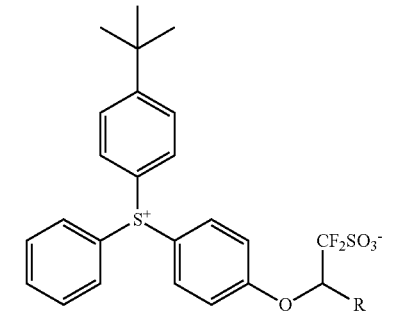

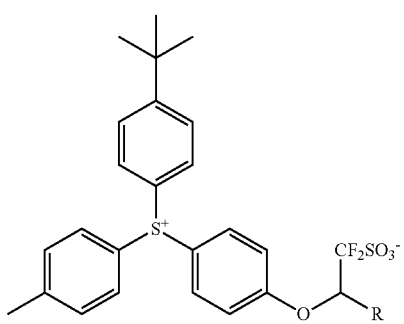

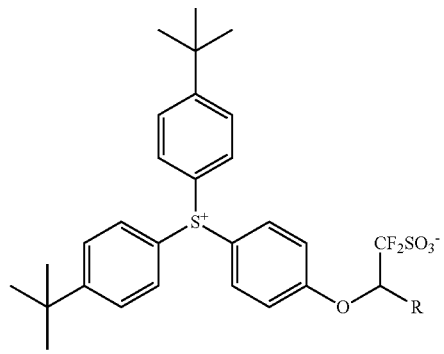

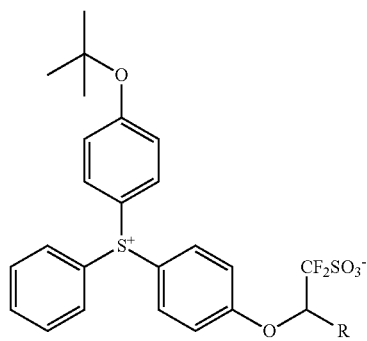

-continued
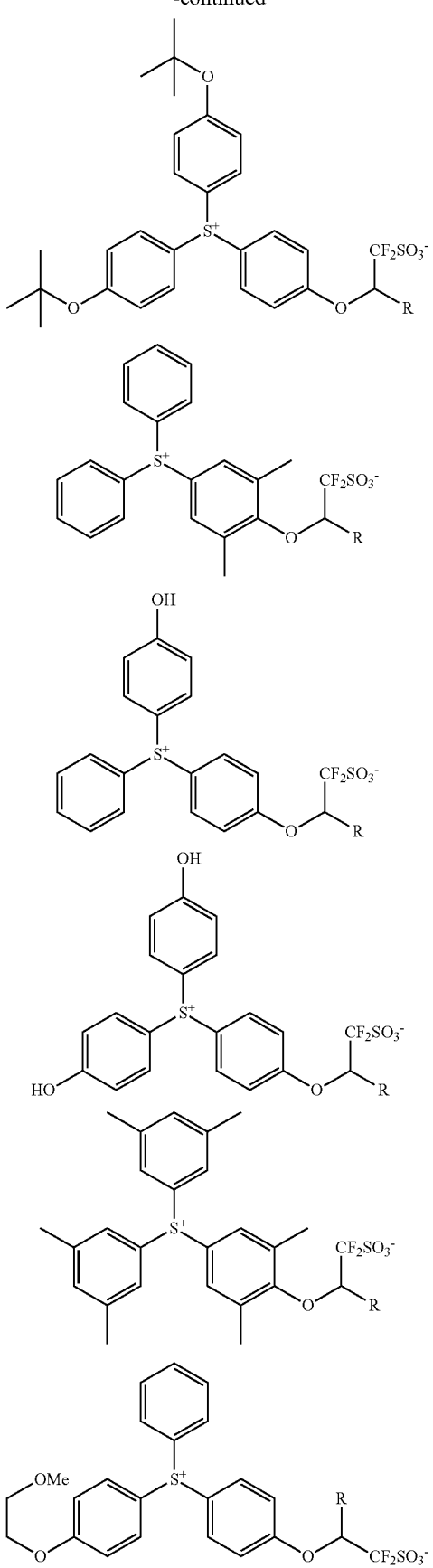
-continued
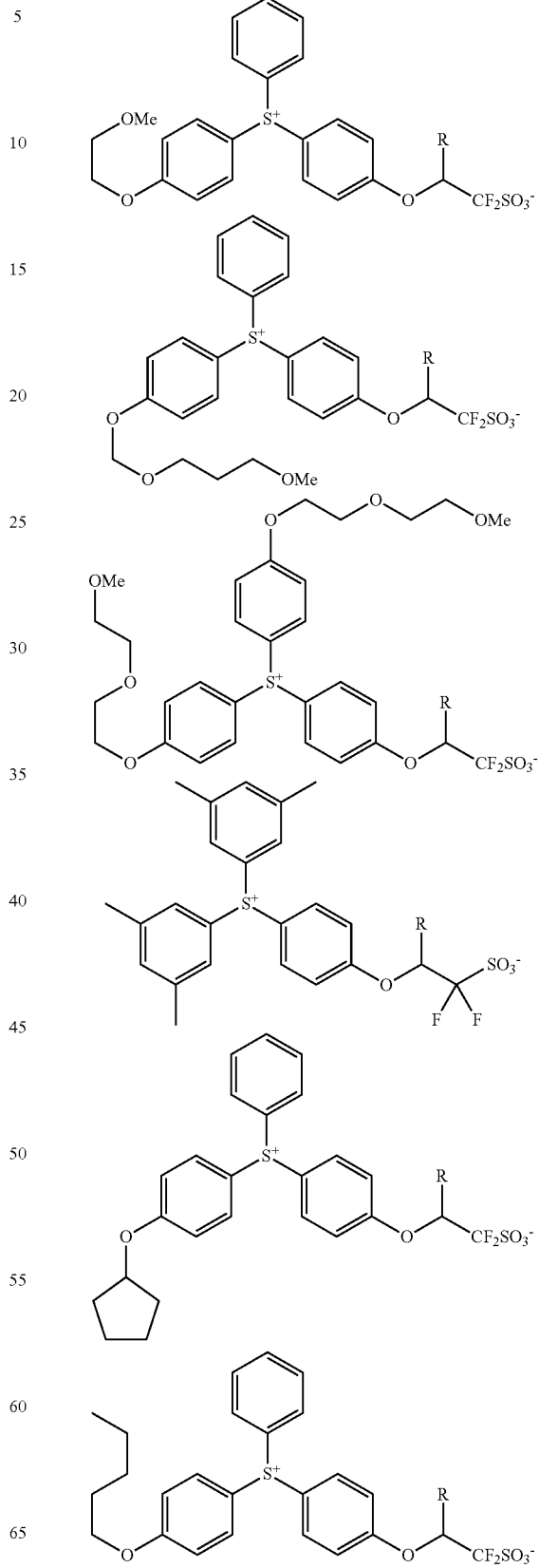

71
-continued
72
-continued
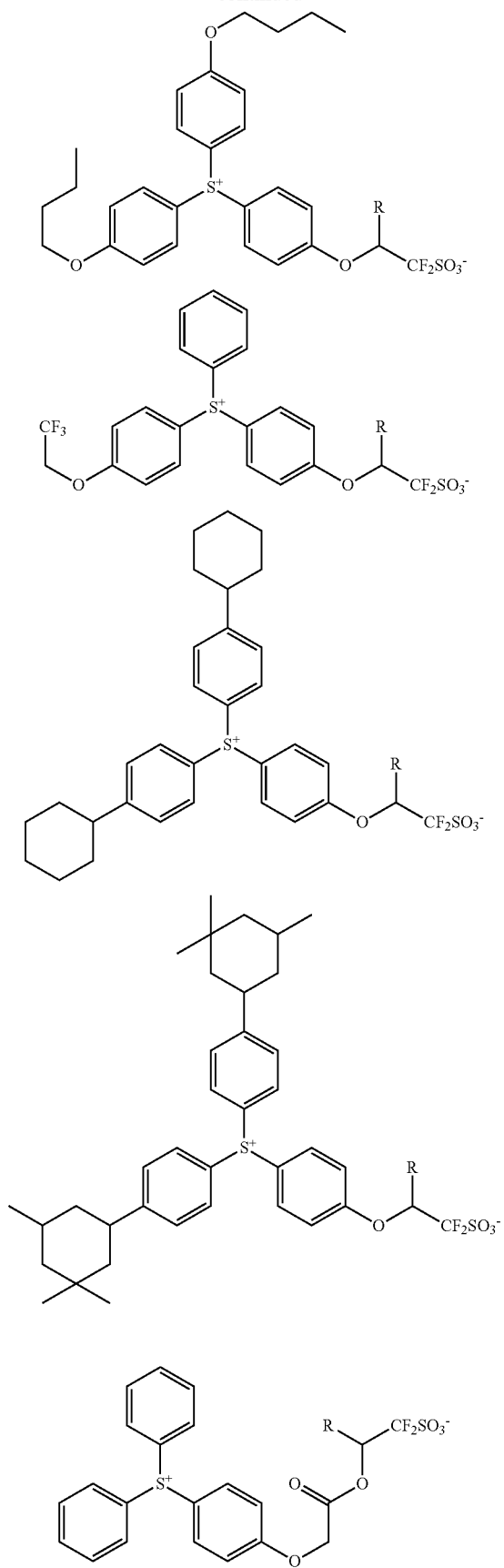
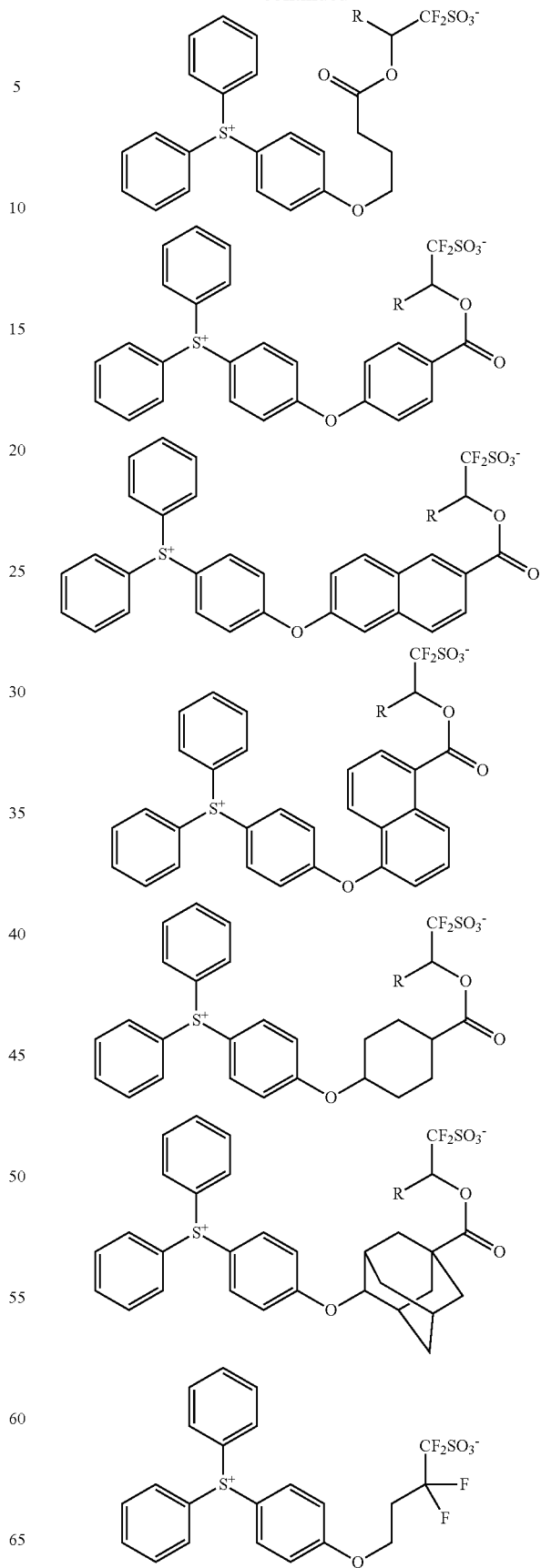

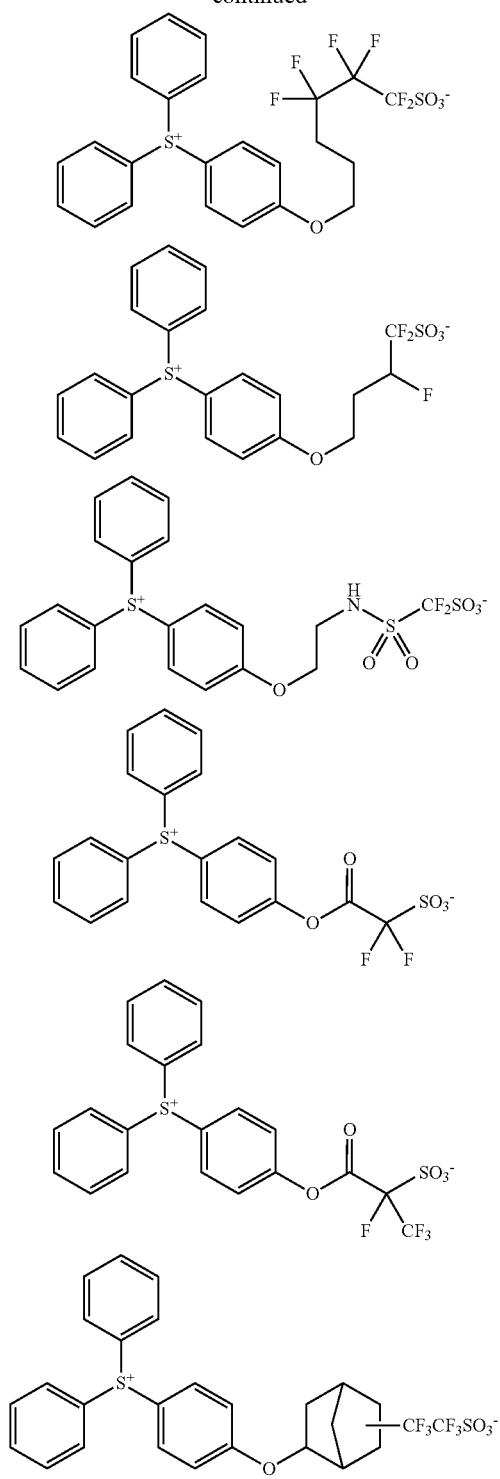

Of the foregoing PAGs, those having an anion of formula (1A') or (1D) are especially preferred because of reduced acid diffusion and high solubility in the resist solvent. Also those having an anion of formula (2') are especially preferred because of extremely reduced acid diffusion.

The PAG is preferably added in an amount of 0.1 to 50 parts, and more preferably 1 to 40 parts by weight per 100 parts by weight of the base polymer.

Other Components

With the quencher containing the iodonium salt of formula (A), the base polymer, and the acid generator, all defined above, other components such as an organic solvent, surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when an acid generator is incorporated to formulate a chemically amplified positive resist composition capable of utilizing acid catalyzed reaction, the composition has a higher sensitivity and is further improved in the properties described above.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of exposed area.

Examples of the organic solvent used herein are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Exemplary surfactants are described in JP-A 2008-111103, paragraphs [0165]-[0166]. Inclusion of a surfactant may improve or control the coating characteristics of the resist to composition. The surfactant is preferably added in an amount of 0.0001 to 10 parts by weight per 100 parts by weight of the base polymer.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

In the resist composition of the invention, a quencher other than the iodonium salt having formula (A) may be blended. The other quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) and similar onium salts of carboxylic acid may also be used as the other quencher. While an α-fluorinated sulfonic acid, imide acid, and methide acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

The other quencher is preferably added in an amount of 0 to 5 parts, more preferably 0 to 4 parts by weight per 100 parts by weight of the base polymer.

To the resist composition, a polymeric additive (or water repellency improver) may also be added for improving the water repellency on surface of a resist film as spin coated. The water repellency improver may be used in the topcoat-less immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Process

The resist composition is used in the fabrication of various integrated circuits. Pattern formation using the resist composition may be performed by well-known lithography processes. The process generally involves coating, prebaking, exposure, and development. If necessary, any additional steps may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably 80 to 120° C. for 30 seconds to 20 minutes. The resulting resist film is generally 0.01 to 2.0 µm thick.

The resist film is then exposed to a desired pattern of high-energy radiation such as UV, deep-UV, EB, EUV, x-ray, soft x-ray, excimer laser light, γ-ray or synchrotron radiation, directly or through a mask having the desired pattern. The exposure dose is preferably about 1 to 200 $mJ/cm^2$, more preferably about 10 to 100 $mJ/cm^2$, or about 0.1 to 100 $\mu C/cm^2$, more preferably about 0.5 to 50 $\mu C/cm^2$. The resist film is further baked (PEB) on a hotplate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer. It is appreciated that the resist composition of the invention is best suited for micro-patterning using such high-energy radiation as KrF and ArF excimer laser, EB, EUV, x-ray, soft x-ray, γ-ray and synchrotron radiation.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

Example

Examples of the invention are given below by way of illustration and not by way of limitation. The abbreviation "pbw" is parts by weight.

Iodonium salts of fluorobenzoic acid bonded to iodized benzene, designated Quenchers 1 to 14, used in resist compositions are identified below. Quenchers 1 to 14 were synthesized by ion exchange between a fluorobenzoic acid bonded to iodized benzene providing the anion shown below and an iodonium chloride providing the cation shown below.

Quencher 1
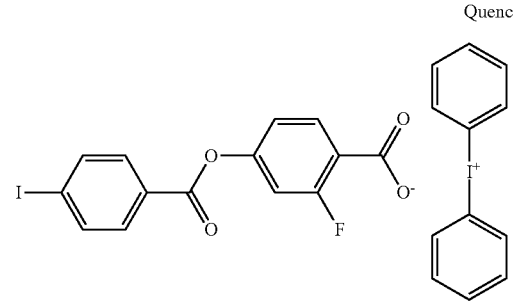
Quencher 2
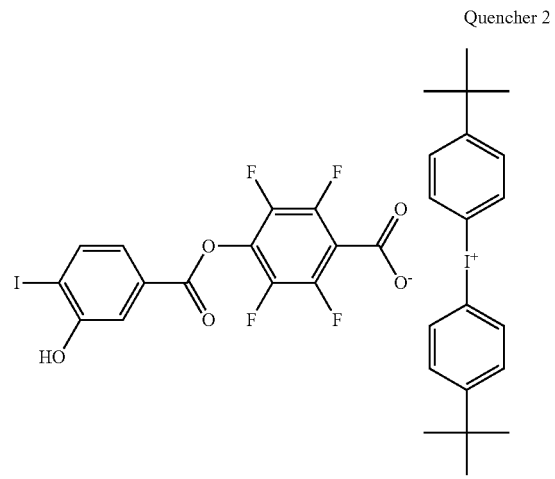
Quencher 3
Quencher 4
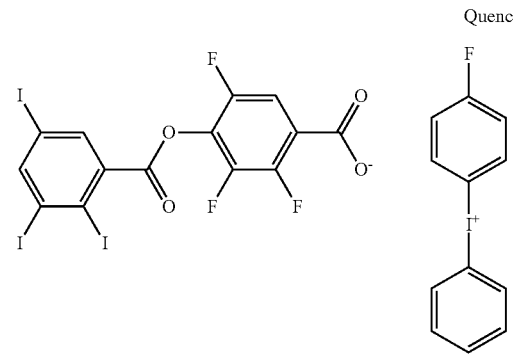
-continued
Quencher 5
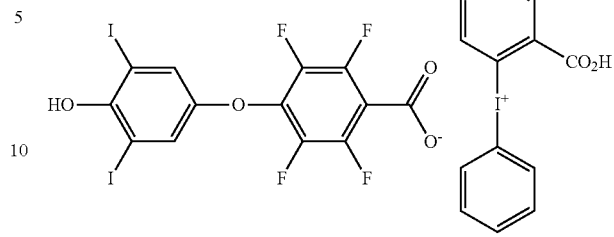
Quencher 6
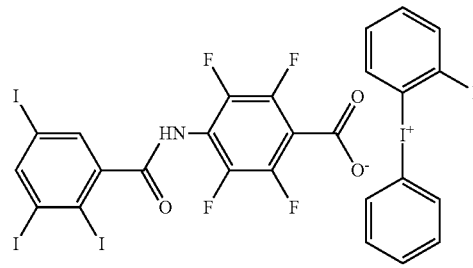
Quencher 7
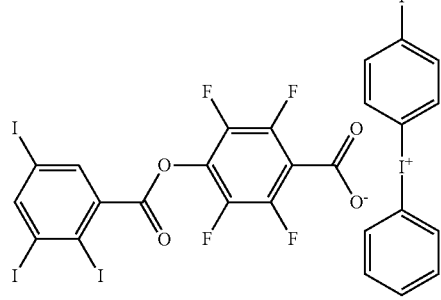
Quencher 8
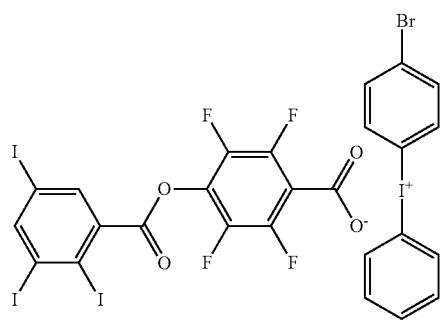
Quencher 9
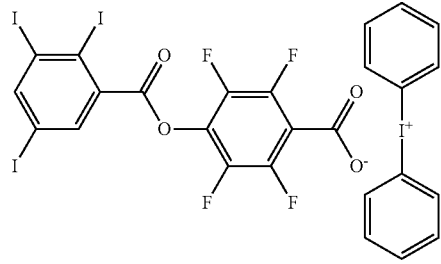
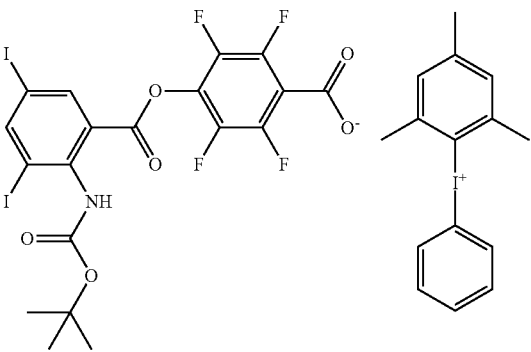

Quencher 10

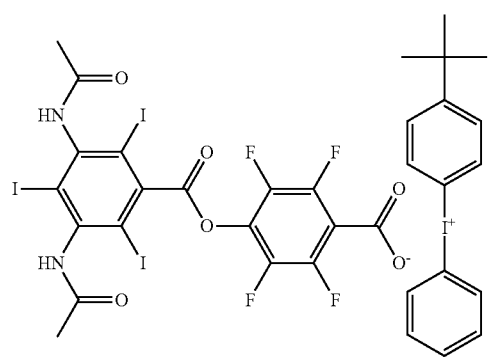

Quencher 14

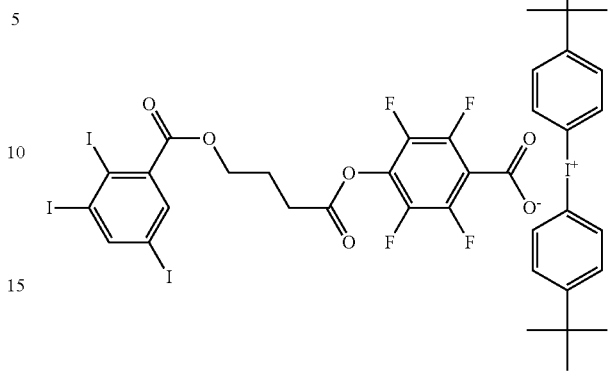

Quencher 11

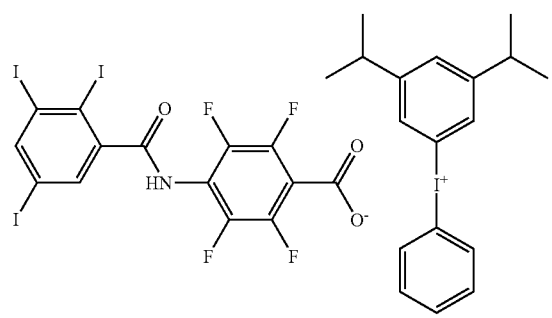

Synthesis Example

Synthesis of Base Polymers (Polymers 1 to 3)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 3, were analyzed for composition by $^1$H-NMR spectroscopy, and for Mw and Mw/Mn by GPC versus polystyrene standards using THF solvent.

Quencher 12

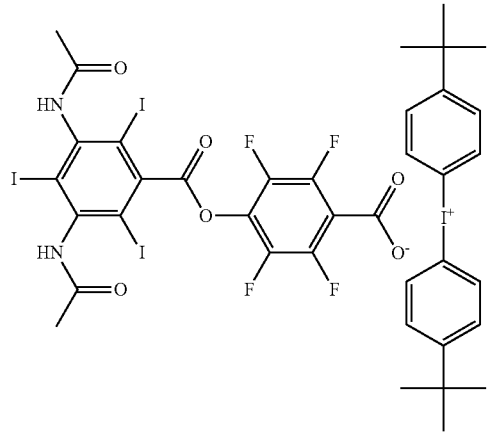

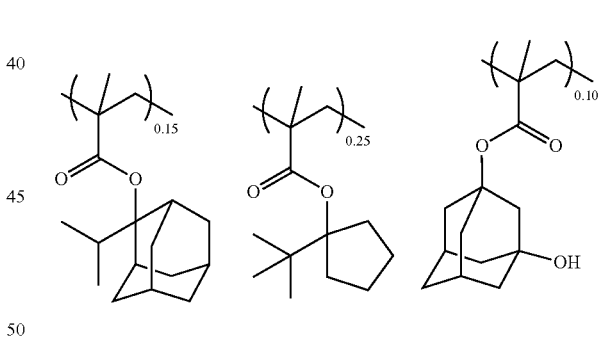

Quencher 13

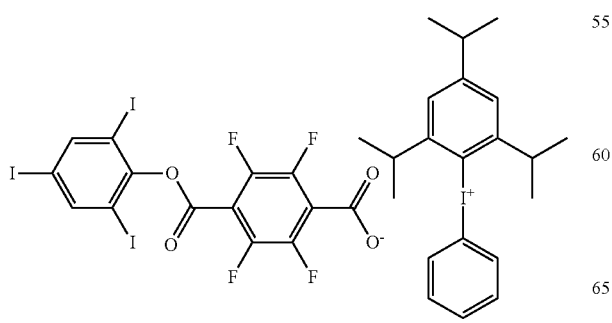

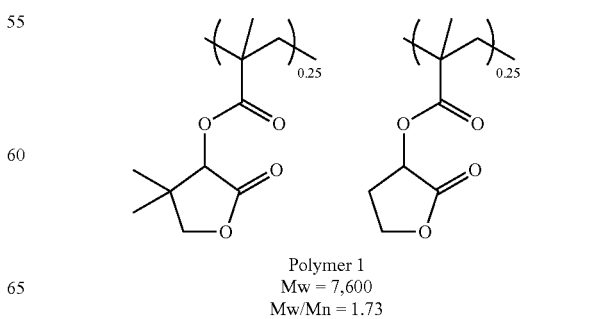

Polymer 1
Mw = 7,600
Mw/Mn = 1.73

-continued

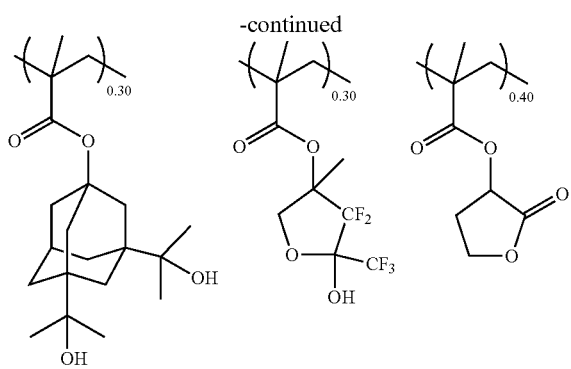

Polymer 2
Mw = 8,100
Mw/Mn = 1.65

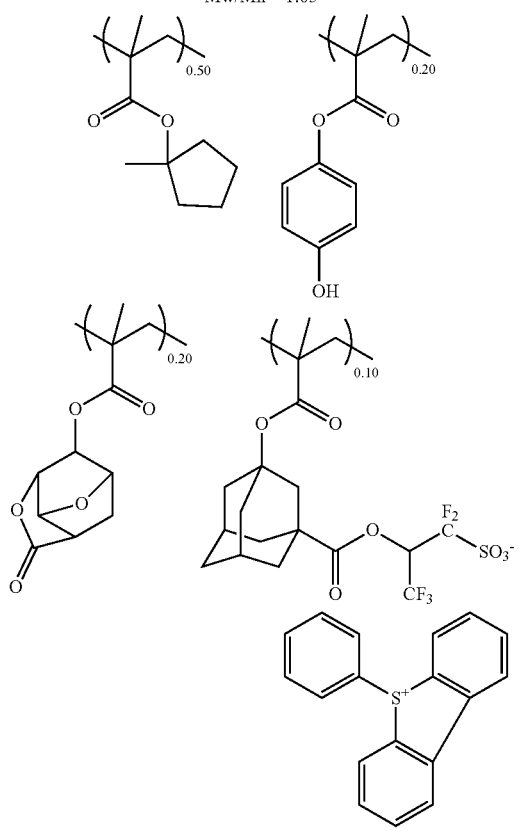

Polymer 3
Mw = 7,900
Mw/Mn = 1.83

Examples and Comparative Examples

Resist compositions were prepared by dissolving the polymer and selected components in a solvent in accordance with the recipe shown in Tables 1 and 2, and filtering through a filter having a pore size of 0.2 μm. The solvent contained 100 ppm of surfactant FC-4430 (3M). The components in Tables 1 and 2 are as identified below.

Organic Solvents:
 PGMEA (propylene glycol monomethyl ether acetate)
 GBL (γ-butyrolactone)
 CyH (cyclohexanone)
 PGME (propylene glycol monomethyl ether)

Acid Generators:
 PAG 1 to PAG 4 of the following structural formulae

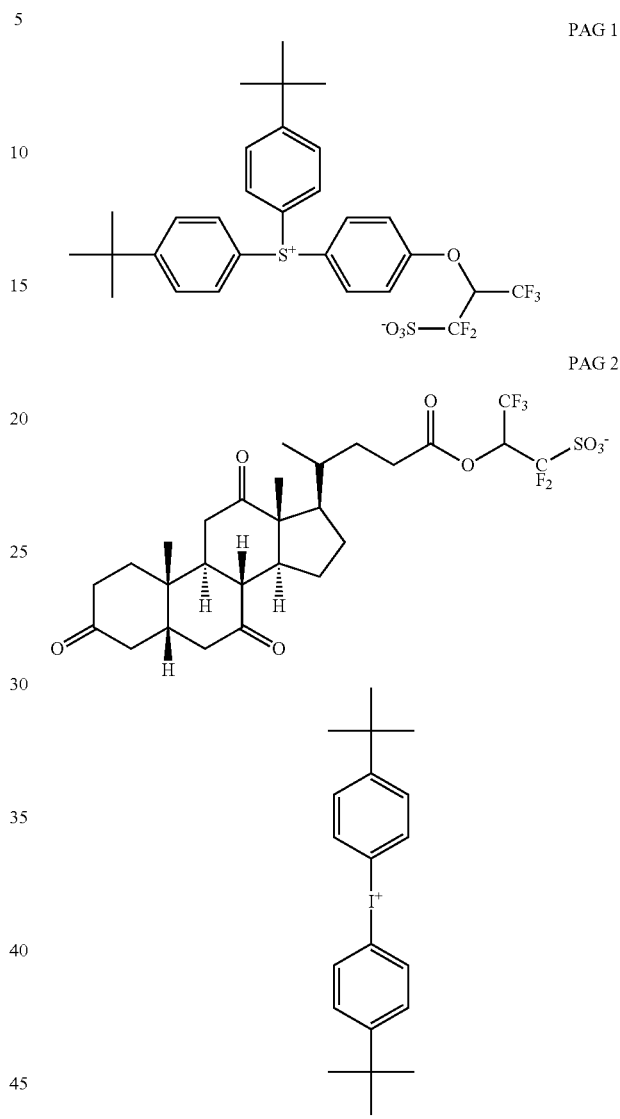

PAG 1

PAG 2

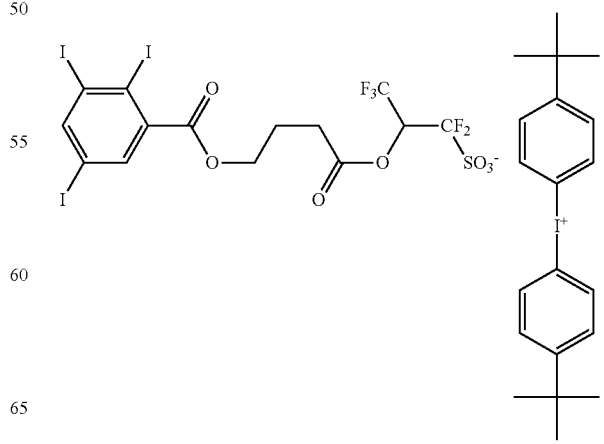

PAG 3

PAG 4

Comparative Quenchers 1 to 7 of the following structural formulae

Comparative Quencher 1

Comparative Quencher 2

Comparative Quencher 3

Comparative Quencher 4

Comparative Quencher 5

Comparative Quencher 6

Comparative Quencher 7

Water-repellent polymers 1 and 2

Water-repellent polymer 1

Mw = 8,900
Mw/Mn = 1.96

Water-repellent polymer 2

Mw = 9,300
Mw/Mn = 1.87

ArF Immersion Lithography Patterning Test

Examples 1-1 to 1-8 and Comparative Examples 1-1 to 1-7

On a substrate (silicon wafer), a spin-on carbon film ODL-102 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions in Table 1 was spin coated, then baked on a hotplate at 100° C. for 60 seconds to form a resist film of 80 nm thick.

Using an ArF excimer laser scanner NSR-S610C (Nikon Corp., NA 1.30, 0.98/0.78, 35° cross-pole illumination, azimuthally polarized illumination), the resist film was exposed through a 6% halftone phase shift mask bearing a pattern having a line of 50 nm and a pitch of 100 nm (on-wafer size) by immersion lithography. Water was used as the immersion liquid. The resist film was baked (PEB) at the temperature shown in Table 1 for 60 seconds. Thereafter, the resist film was developed in n-butyl acetate for 30 seconds in Examples 1-1 to 1-7 and Comparative Examples 1-1 to 1-6 or in 2.38 wt % tetramethylammonium hydroxide (TMAH) aqueous solution in Example 1-8 and Comparative Example 1-7, yielding a negative line-and-space (L/S) pattern having a space of 50 nm and a pitch of 100 nm.

The pattern was observed under a CD-SEM (CG-4000, Hitachi High-Technologies Corp.). The exposure dose capable of resolving a L/S pattern at 1:1 was determined as sensitivity, and edge roughness (LWR) at that dose was measured. The results are shown in Table 1.

TABLE 1

| | | Polymer (pbw) | Acid generator (pbw) | Quencher (pbw) | Water-repellent polymer (pbw) | Organic solvent (pbw) | PEB temp. (° C.) | Sensitivity (mJ/cm$^2$) | LWR (nm) |
|---|---|---|---|---|---|---|---|---|---|
| Example | 1-1 | Polymer 1 (100) | PAG 1 (6.0) | Quencher 1 (4.50) | Water-repellent polymer 1 (4.0) | PGMEA (2,200) GBL (300) | 95 | 32 | 3.5 |
| | 1-2 | Polymer 1 (100) | PAG 1 (6.0) | Quencher 2 (4.50) | Water-repellent polymer 1 (4.0) | PGMEA (2,200) GBL (300) | 95 | 34 | 3.2 |
| | 1-3 | Polymer 1 (100) | PAG 1 (6.0) | Quencher 3 (3.00) | Water-repellent polymer 1 (4.0) | PGMEA (2,200) GBL (300) | 95 | 35 | 3.9 |
| | 1-4 | Polymer 1 (100) | PAG 1 (6.0) | Quencher 4 (4.50) | Water-repellent polymer 1 (4.0) | PGMEA (2,200) GBL (300) | 95 | 39 | 2.8 |
| | 1-5 | Polymer 1 (100) | PAG 1 (6.0) | Quencher 6 (4.50) | Water-repellent polymer 1 (4.0) | PGMEA (2,200) GBL (300) | 95 | 31 | 3.1 |
| | 1-6 | Polymer 1 (100) | PAG 1 (6.0) | Quencher 11 (4.50) | Water-repellent polymer 1 (4.0) | PGMEA (2,200) GBL (300) | 95 | 40 | 2.8 |
| | 1-7 | Polymer 1 (100) | PAG 1 (6.0) | Quencher 13 (4.50) | Water-repellent polymer 1 (4.0) | PGMEA (2,200) GBL (300) | 95 | 42 | 2.7 |
| | 1-8 | Polymer 2 (100) | PAG 1 (6.0) | Quencher 5 (4.50) | Water-repellent polymer 2 (4.0) | PGMEA (2,200) GBL (300) | 95 | 44 | 2.1 |
| Comparative Example | 1-1 | Polymer 1 (100) | PAG 1 (6.0) | Comparative Quencher 1 (2.13) | Water-repellent polymer 1 (4.0) | PGMEA (2,200) GBL (300) | 95 | 37 | 5.0 |
| | 1-2 | Polymer 1 (100) | PAG 1 (6.0) | Comparative Quencher 2 (2.13) | Water-repellent polymer 1 (4.0) | PGMEA (2,200) GBL (300) | 95 | 46 | 4.4 |
| | 1-3 | Polymer 1 (100) | PAG 1 (6.0) | Comparative Quencher 3 (4.50) | Water-repellent polymer 1 (4.0) | PGMEA (2,200) GBL (300) | 95 | 38 | 4.3 |
| | 1-4 | Polymer 1 (100) | PAG 1 (6.0) | Comparative Quencher 4 (4.50) | Water-repellent polymer 1 (4.0) | PGMEA (2,200) GBL (300) | 95 | 42 | 4.5 |
| | 1-5 | Polymer 1 (100) | PAG 1 (6.0) | Comparative Quencher 5 (4.50) | Water-repellent polymer 1 (4.0) | PGMEA (2,200) GBL (300) | 95 | 56 | 4.9 |
| | 1-6 | Polymer 1 (100) | PAG 1 (6.0) | Comparative Quencher 6 (4.50) | Water-repellent polymer 1 (4.0) | PGMEA (2,200) GBL (300) | 95 | 39 | 4.6 |
| | 1-7 | Polymer 2 (100) | PAG 1 (6.0) | Comparative Quencher 7 (4.50) | Water-repellent polymer 2 (4.0) | PGMEA (2,200) GBL (300) | 100 | 58 | 6.0 |

EUV Lithography Test

Examples 2-1 to 2-11 and Comparative Example 2-1

The resist composition in Table 2 was spin coated on a silicon substrate having a 13-nm coating of spin-on-hard-mask material SHB-A940 (Shin-Etsu Chemical Co., Ltd.) having a silicon content of 43 wt % and prebaked on a hotplate at 105° C. for 60 seconds to form a resist film of 60 nm thick. Using an EUV scanner NXE3300 (ASML, NA 0.33, σ 0.9/0.6, quadrupole illumination), the resist film was exposed to EUV through a patterned mask. The resist film was baked (PEB) on a hotplate at the temperature shown in Table 2 for 60 seconds and developed in a 2.38 wt % TMAH aqueous solution for 30 seconds to form a hole pattern having a size of 23 nm and a pitch of 46 nm.

The resist pattern was evaluated under CD-SEM (CG-5000, Hitachi High-Technologies Corp.). The exposure dose that provides a hole pattern having a size of 23 nm is reported as sensitivity. The size of 50 holes at that dose was measured, from which a size variation (3σ) was computed and reported as CDU.

The resist composition is shown in Table 2 together with the sensitivity and CDU of EUV lithography.

TABLE 2

|  |  | Polymer (pbw) | Acid generator (pbw) | Quencher (pbw) | Organic solvent (pbw) | PEB temp. (° C.) | Sensitivity (mJ/cm$^2$) | CDU (nm) |
| --- | --- | --- | --- | --- | --- | --- | --- | --- |
| Example | 2-1 | Polymer 3 (100) | — | Quencher 7 (4.00) | PGMEA (400) CyH (2,000) PGME (100) | 100 | 26 | 2.4 |
|  | 2-2 | Polymer 3 (100) | — | Quencher 8 (4.00) | PGMEA (400) CyH (2,000) PGME (100) | 100 | 28 | 2.3 |
|  | 2-3 | Polymer 3 (100) | — | Quencher 9 (4.50) | PGMEA (400) CyH (2,000) PGME (100) | 100 | 24 | 2.3 |
|  | 2-4 | Polymer 3 (100) | — | Quencher 10 (4.50) | PGMEA (400) CyH (2,000) PGME (100) | 100 | 25 | 2.3 |
|  | 2-5 | Polymer 3 (100) | — | Quencher 11 (4.50) | PGMEA (400) CyH (2,000) PGME (100) | 100 | 26 | 2.1 |
|  | 2-6 | Polymer 3 (100) | — | Quencher 12 (4.50) | PGMEA (400) CyH (2,000) PGME (100) | 100 | 28 | 2.0 |
|  | 2-7 | Polymer 3 (100) | — | Quencher 13 (4.50) | PGMEA (400) CyH (2,000) PGME (100) | 100 | 24 | 2.1 |
|  | 2-8 | Polymer 3 (100) | — | Quencher 14 (5.00) | PGMEA (400) CyH (2,000) PGME (100) | 100 | 20 | 2.2 |
|  | 2-9 | Polymer 3 (100) | PAG 2 (15) | Quencher 13 (4.50) | PGMEA (400) CyH (2,000) PGME (100) | 100 | 21 | 2.9 |
|  | 2-10 | Polymer 3 (100) | PAG 3 (15) | Quencher 13 (4.50) | PGMEA (400) CyH (2,000) PGME (100) | 100 | 16 | 2.6 |
|  | 2-11 | Polymer 3 (100) | PAG 4 (15) | Quencher 13 (4.50) | PGMEA (400) CyH (2,000) PGME (100) | 100 | 14 | 2.9 |
| Comparative Example | 2-1 | Polymer 3 (100) | — | Comparative Quencher 6 (2.50) | PGMEA (400) CyH (2,000) PGME (100) | 100 | 35 | 4.0 |

It is demonstrated in Tables 1 and 2 that resist compositions comprising an iodonium salt having formula (A) within the scope of the invention offer a satisfactory resolution and improved LWR and CDU.

Japanese Patent Application No. 2017-052391 is incorporated herein by reference. Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer, an acid generator and a quencher containing an iodonium salt having the formula (A):

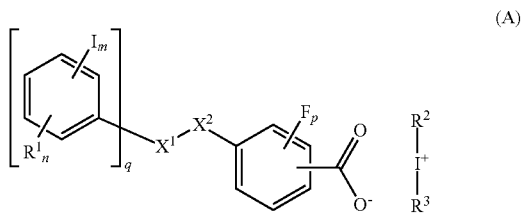

(A)

wherein $R^1$ is a hydroxyl group, $C_1$-$C_6$ straight, branched or cyclic alkyl or alkoxy group, $C_2$-$C_6$ straight, branched or cyclic acyloxy group, fluorine, chlorine, bromine, amino, —NR$^5$—C(=O)—R$^6$, or —NR$^5$—C(=O)—O—R$^6$, $R^5$ is hydrogen or a $C_1$-$C_6$ straight, branched or cyclic alkyl group, $R^6$ is a $C_1$-$C_6$ straight, branched or cyclic alkyl group or $C_2$-$C_8$ straight, branched or cyclic alkenyl group; $X^1$ is a single bond or a (q+1)-valent $C_1$-$C_{20}$ linking group which may contain at least one moiety selected from ether, carbonyl, ester, amide, sultone, lactam, carbonate, halogen, hydroxyl and carboxyl; $X^2$ is an ether, ester or amide group; $R^2$ and $R^3$ are each independently trifluoromethyl or a $C_6$-$C_{10}$ aryl, $C_2$-$C_6$ alkenyl or $C_2$-$C_6$ alkynyl group in which at least one hydrogen atom may be substituted by halogen, trifluoromethyl, $C_1$-$C_{10}$ straight, branched or cyclic alkyl, $C_1$-$C_{10}$ straight, branched or cyclic alkoxy, hydroxyl, carboxyl, $C_2$-$C_{10}$ straight, branched or cyclic alkoxycarbonyl, nitro and/or cyano; m is an integer of 1 to 5, n is an integer of 0 to 3, p is an integer of 1 to 4, and q is an integer of 1 to 3.

2. The resist composition of claim 1 wherein m is equal to 3.

3. The resist composition of claim 1 wherein the acid generator is capable of generating a sulfonic acid, imide acid or methide acid.

4. The resist composition of claim 1, further comprising an organic solvent.

5. The resist composition of claim 1 wherein the base polymer comprises recurring units having the formula (a1) or recurring units having the formula (a2):

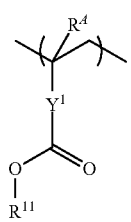

(a1)

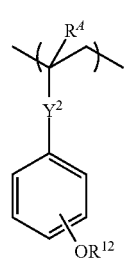

(a2)

wherein $R^A$ is each independently hydrogen or methyl, $R^{11}$ and $R^{12}$ each are an acid labile group, $Y^1$ is a single bond, phenylene group, naphthylene group, or $C_1$-$C_{12}$ linking group containing an ester moiety and/or lactone ring, and $Y^2$ is a single bond or ester group.

6. The resist composition of claim 5, further comprising a dissolution inhibitor.

7. The resist composition of claim 5 which is a chemically amplified positive resist composition.

8. The resist composition of claim 1 wherein the base polymer is free of an acid labile group.

9. The resist composition of claim 8, further comprising a crosslinker.

10. The resist composition of claim 8 which is a chemically amplified negative resist composition.

11. The resist composition of claim 1, further comprising a surfactant.

12. A resist composition comprising a base polymer and a quencher containing an iodonium salt having the formula (A):

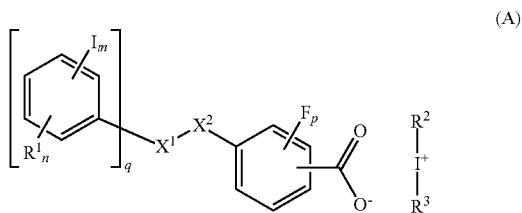

(A)

wherein $R^1$ is a hydroxyl group, $C_1$-$C_6$ straight, branched or cyclic alkyl or alkoxy group, $C_2$-$C_6$ straight, branched or cyclic acyloxy group, fluorine, chlorine, bromine, amino, —NR$^5$—C(=O)—R$^6$, or —NR$^5$—C(=O)—O—R$^6$, $R^5$ is hydrogen or a $C_1$-$C_6$ straight, branched or cyclic alkyl group, $R^6$ is a $C_1$-$C_6$ straight, branched or cyclic alkyl group or $C_2$-$C_8$ straight, branched or cyclic alkenyl group, $X^1$ is a single bond or a (q+1)-valent $C_1$-$C_{20}$ linking group which may contain at least one moiety selected from ether, carbonyl, ester, amide, sultone, lactam, carbonate, halogen, hydroxyl and carboxyl; $X^2$ is an ether, ester or amide group; $R^2$ and $R^3$ are each independently trifluoromethyl or a $C_6$-$C_{10}$ aryl, $C_2$-$C_6$ alkenyl or $C_2$-$C_6$ alkynyl group in which at least one hydrogen atom may be substituted by halogen, trifluoromethyl, $C_1$-$C_{10}$ straight, branched or cyclic alkyl, $C_1$-$C_{10}$ straight, branched or cyclic alkoxy, hydroxyl, carboxyl, $C_2$-$C_{10}$ straight, branched or cyclic alkoxycarbonyl, nitro and/or cyano; m is an integer of 1 to 5, n is an integer of 0 to 3, p is an integer of 1 to 4, and q is an integer of 1 to 3, wherein the base polymer further comprises recurring units of at least one type selected from the formulae (f1) to (f3):

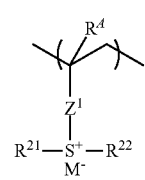

(f1)

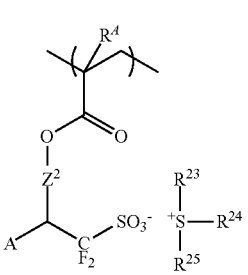

(f2)

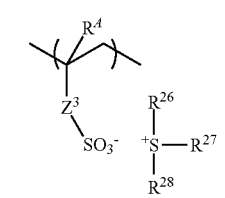

(f3)

wherein $R^4$ is each independently hydrogen or methyl, $Z^1$ is a single bond, phenylene group, —O—$Z^{12}$— or —C(=O)—$Z^{11}$-$Z^{12}$—, $Z^{11}$ is —O— or —NH—, $Z^{12}$ is a $C_1$-$C_6$ straight, branched or cyclic alkylene group, $C_2$-$C_6$ straight, branched or cyclic alkenylene group or phenylene group, which may contain a carbonyl, ester, ether or hydroxy moiety, $R^{21}$ to $R^{28}$ are each independently a $C_1$-$C_{12}$ straight, branched or cyclic alkyl group which may contain a carbonyl, ester or ether moiety, or a $C_6$-$C_{12}$ aryl group or $C_7$-$C_{20}$ aralkyl group, in which at least one hydrogen may be substituted by a $C_1$-$C_{10}$ straight, branched or cyclic alkyl moiety, halogen, trifluoromethyl, cyano, nitro, hydroxyl, mercapto, $C_1$-$C_{10}$ straight, branched or cyclic alkoxy moiety, $C_2$-$C_{10}$ straight, branched or cyclic alkoxycarbonyl moiety, or $C_2$-$C_{10}$ straight, branched or cyclic acyloxy moiety, any two of $R^{23}$, $R^{24}$ and $R^{25}$, or any two of $R^{26}$, $R^{27}$ and $R^{28}$ may bond together to form a ring with the sulfur atom to which they are attached, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ straight, branched or cyclic alkylene group which may contain a carbonyl, ester or ether moiety, A is hydrogen or trifluoromethyl, $Z^3$ is a single bond, methylene group, ethylene group, phenylene group, fluorinated phenylene group, —O—$Z^{32}$—, or —C(=O)—$Z^{31}$-$Z^{32}$—, $Z^{31}$ is —O— or —NH—, $Z^{32}$ is a $C_1$-$C_6$ straight, branched or cyclic alkylene group, phenylene, fluorinated phenylene or trifluoromethyl-substituted phenylene group, or $C_2$-$C_6$ straight, branched or cyclic alkenylene group, which may contain a carbonyl, ester, ether or hydroxyl moiety, and $M^-$ is a non-nucleophilic counter ion.

13. A process for forming a pattern comprising the steps of applying the resist composition of claim 1 onto a substrate, baking to form a resist film, exposing the resist film to high-energy radiation, and developing the exposed film in a developer.

14. The process of claim 13 wherein the high-energy radiation is ArF excimer laser radiation of wavelength 193 nm or KrF excimer laser radiation of wavelength 248 nm.

15. The process of claim 13 wherein the high-energy radiation is electron beam or extreme ultraviolet radiation of wavelength 3 to 15 nm.

16. A process for forming a pattern comprising the steps of applying the resist composition of claim 12 onto a substrate, baking to form a resist film, exposing the resist film to high-energy radiation, and developing the exposed film in a developer.

17. The process of claim 16 wherein the high-energy radiation is ArF excimer laser radiation of wavelength 193 nm or KrF excimer laser radiation of wavelength 248 nm.

18. The process of claim 16 wherein the high-energy radiation is electron beam or extreme ultraviolet radiation of wavelength 3 to 15 nm.

\* \* \* \* \*